(12) United States Patent
Solomon et al.

(10) Patent No.: US 8,039,594 B2
(45) Date of Patent: Oct. 18, 2011

(54) HUMAN SYNTHETIC SINGLE-CHAIN ANTIBODIES DIRECTED AGAINST THE COMMON EPITOPE OF MUTANT P53 AND THEIR USES

(75) Inventors: Beka Solomon, Herzlia Pituach (IL); Sara Orgad, Gedera (IL); Itai Benhar, Rechovot (IL); Ronit Rosenfeld, Nes Ziona (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 430 days.

(21) Appl. No.: 11/887,123

(22) PCT Filed: Mar. 23, 2006

(86) PCT No.: PCT/IL2006/000372
§ 371 (c)(1),
(2), (4) Date: May 8, 2009

(87) PCT Pub. No.: WO2006/100681
PCT Pub. Date: Sep. 28, 2006

(65) Prior Publication Data
US 2010/0074908 A1     Mar. 25, 2010

Related U.S. Application Data

(60) Provisional application No. 60/664,967, filed on Mar. 25, 2005, provisional application No. 60/698,919, filed on Jul. 14, 2005.

(51) Int. Cl.
*C12P 21/08* (2006.01)
(52) U.S. Cl. ............... 530/387.3; 530/387.7; 530/391.1
(58) Field of Classification Search ............... 530/387.3, 530/387.7, 391.1
See application file for complete search history.

(56) References Cited

FOREIGN PATENT DOCUMENTS
WO   WO 98/18825   5/1998
WO   WO 01/68801   9/2001

OTHER PUBLICATIONS

Cellular and Molecular Immunology (Eds. Abass et al.; 1991; W.B. Saunders: Philadelphia; p. 54).*
Azriel-Rosenfeld et al. "A Human Synthetic Combinatorial Library of Arrayable Single-Chain Antibodies Based on Shuffling In Vivo Formed CDRs Into General Framework Regions", Journal of Molecular Biology, 335(1): 177-192, 2004.
Gannon et al. "Activating Mutations in P53 Produce A Common Conformational Effect. A Monoclonal Antibody Specific for the Mutant Form", The EMBO Journal, 9(5): 1595-1602, 1990.
Govorko et al. "Single-Chain Antibody Against the Common Epitope of Mutant P53: Isolation and Intracytosolic Expression in Mammalian Cells", Journal of Immunological Methods, 258: 169-181, 2001.
Orgad et al. "Single Chain Antibody Against the Common Epitope of Mutant P53 Restores Wild-Type Activity to Mutant P53 Protein", FEBS Letters, 579(25): 5609-5615, 2005.
Communication Relating to the Results of the Partial International Search Dated Aug. 4, 2006 From the International Searching Authority Re.: Application No. PCT/IL2006/000372.
International Preliminary Report on Patentability Dated Oct. 4, 2007 From the International Bureau of WIPO Re.: Application No. PCT/IL2006/000372.

* cited by examiner

*Primary Examiner* — Misook Yu
*Assistant Examiner* — Brad Duffy

(57) ABSTRACT

Isolated polypeptides, isolated polynucleotides or expression vectors encoding same, viral display vehicles which can be specifically bind an exposed epitope shared by mutant, but not wild type, p53 protein are provided. Also provided are methods of inducing apoptosis and treating cancer as well as diagnosing a p53-related cancer using the isolated polypeptides uncovered by the present invention.

3 Claims, 24 Drawing Sheets
(15 of 24 Drawing Sheet(s) Filed in Color)

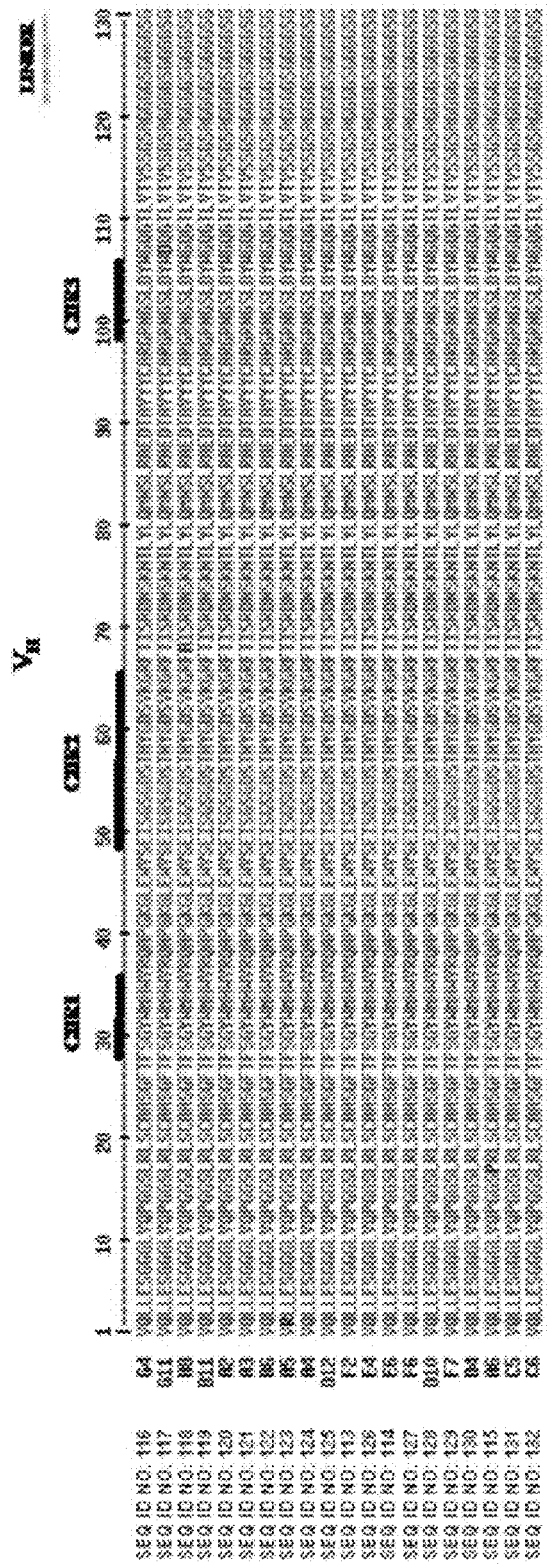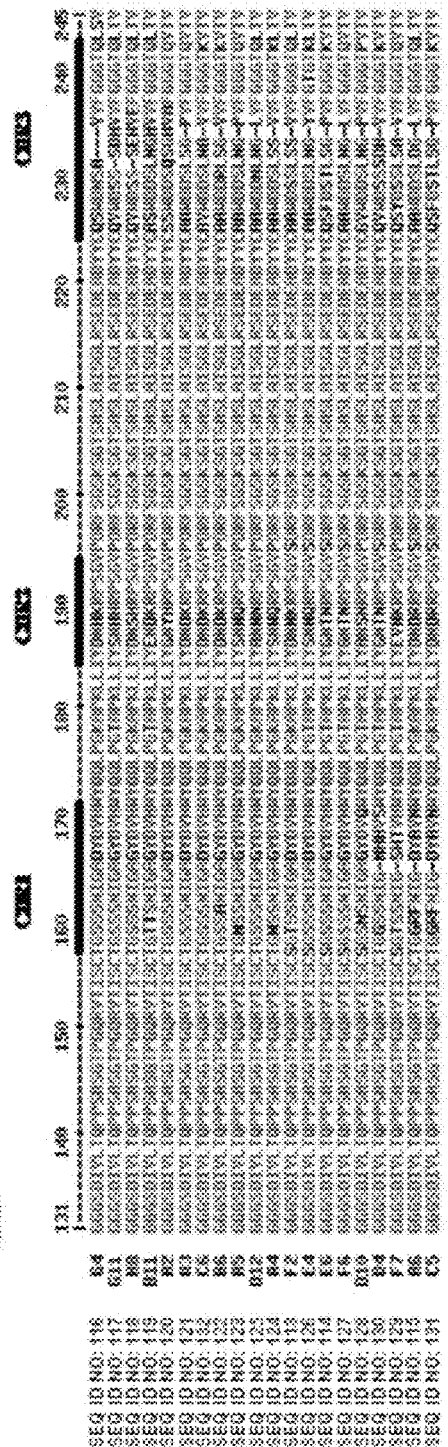

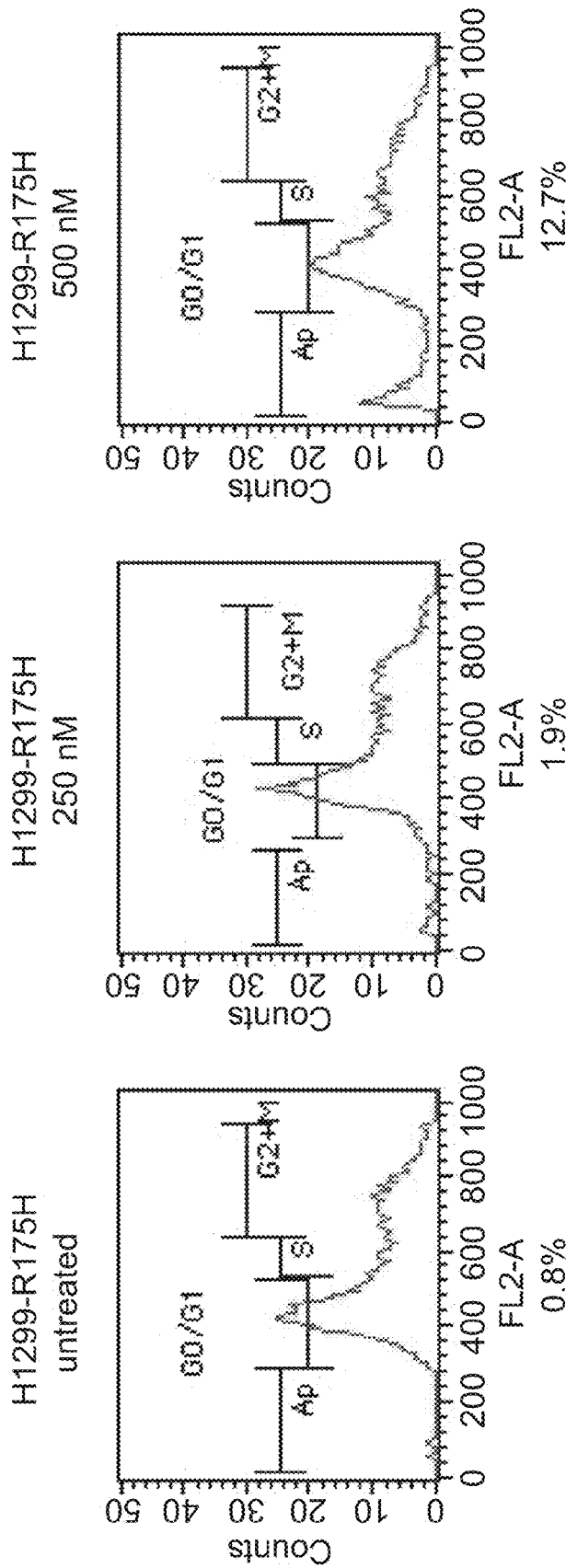

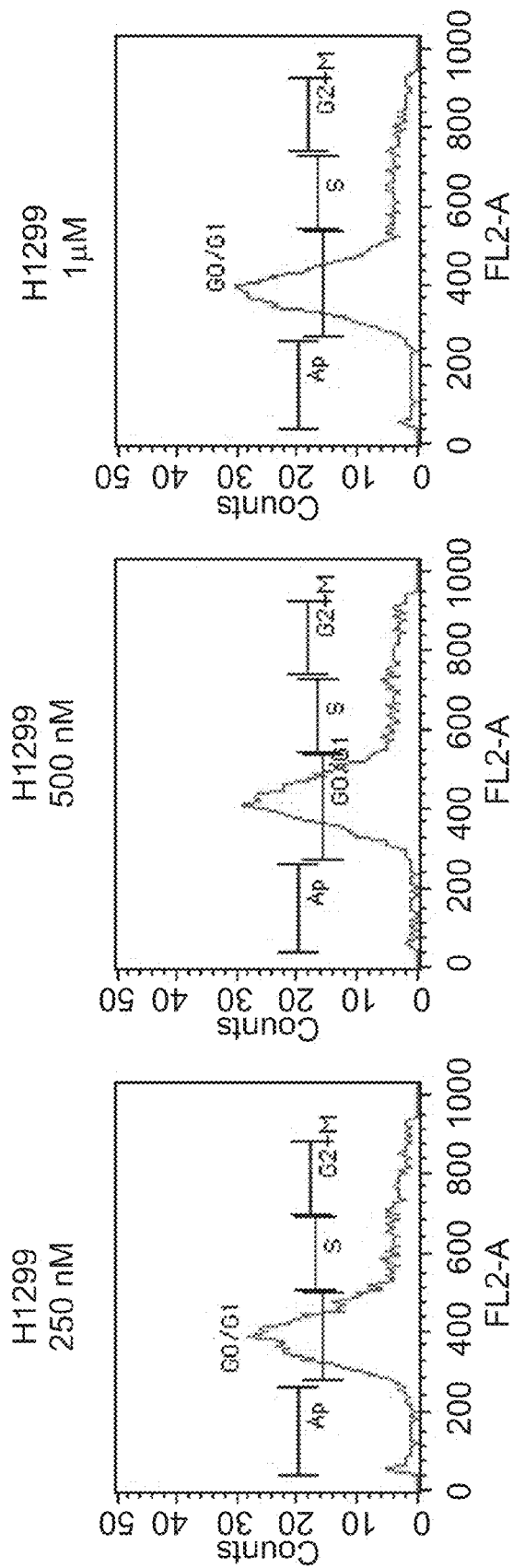

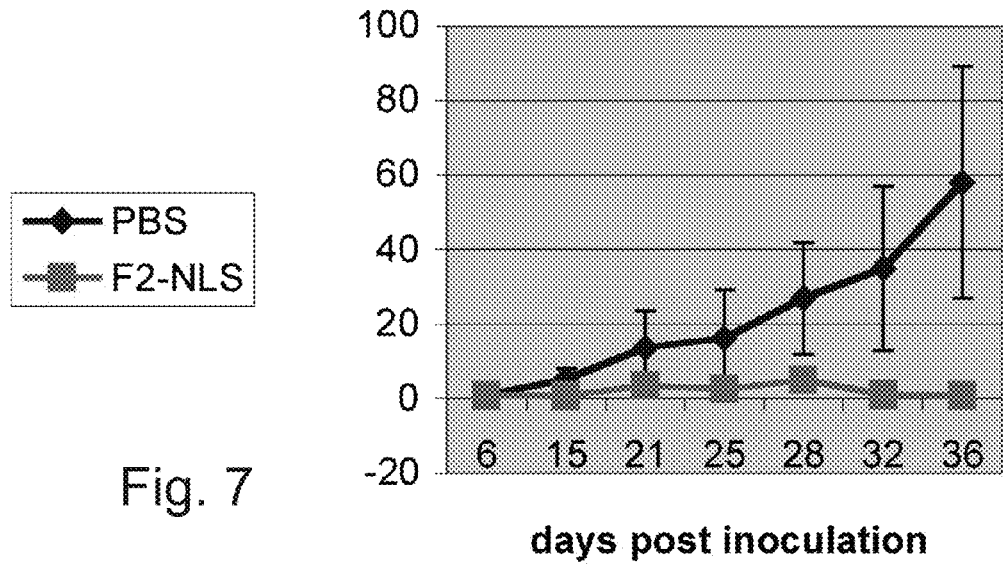
Fig. 7
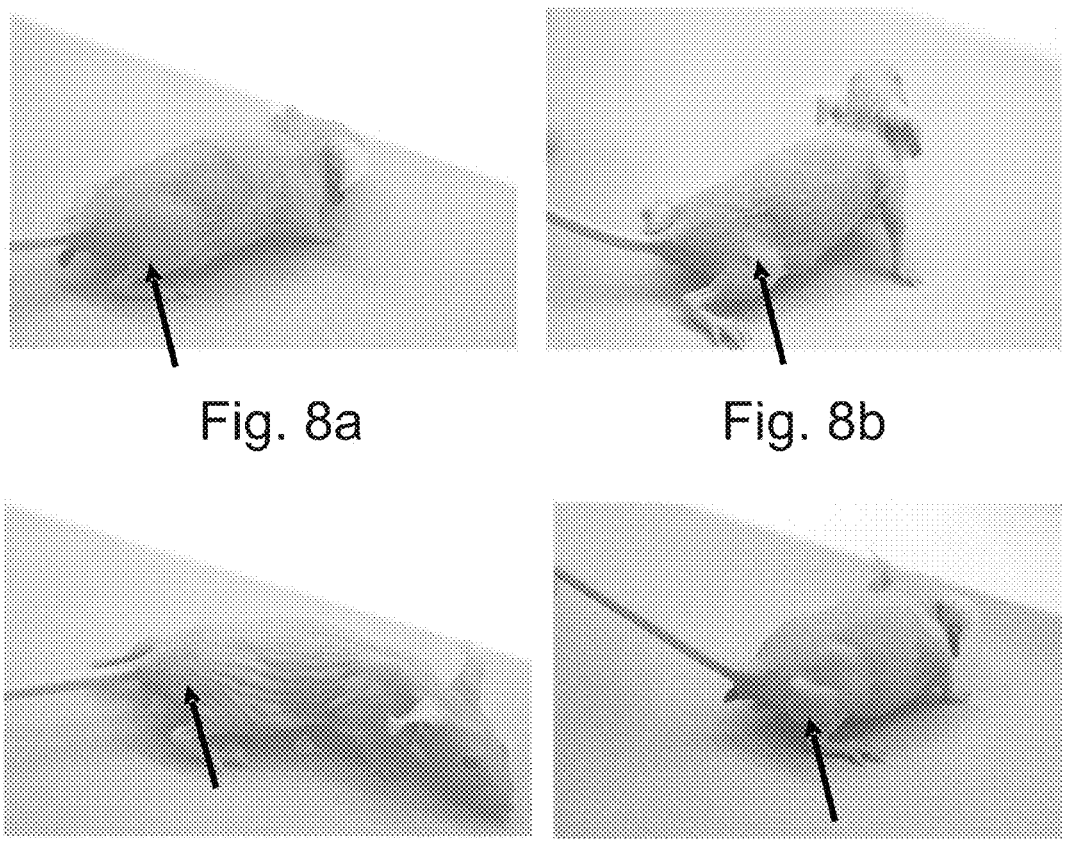
Fig. 8a  Fig. 8b
Fig. 8c  Fig. 8d

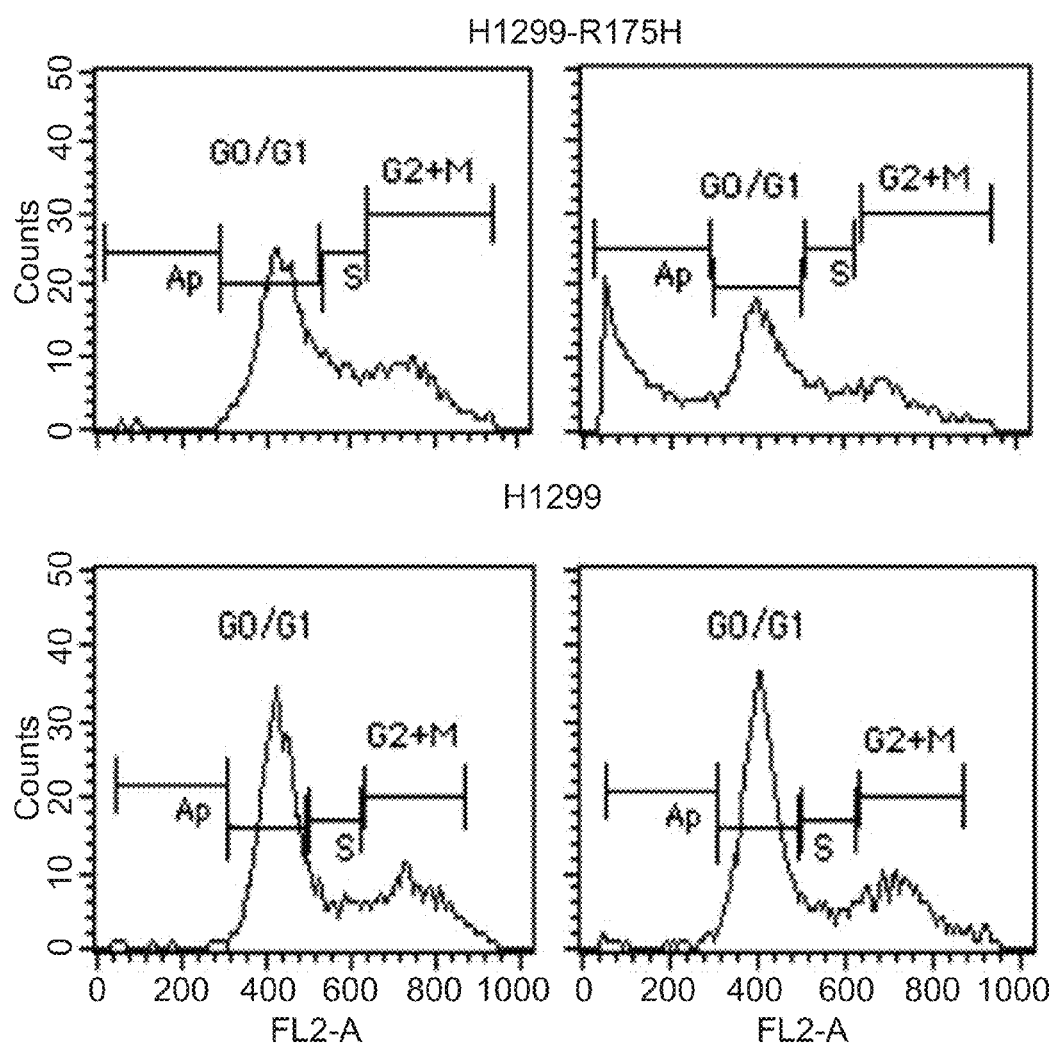

Fig. 15e
Untreated
Fig. 15f
1μM TAR1
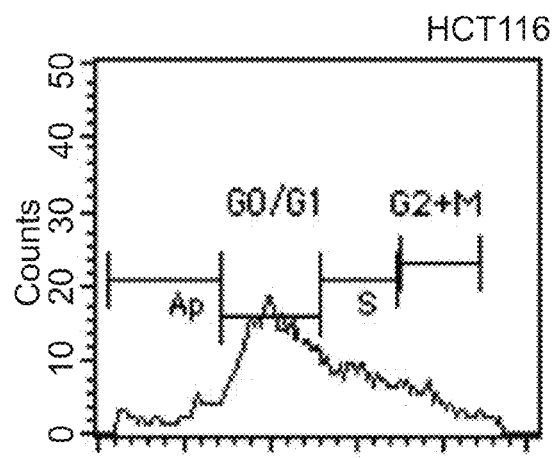
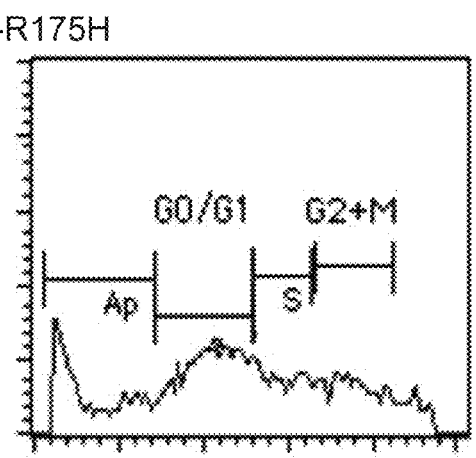
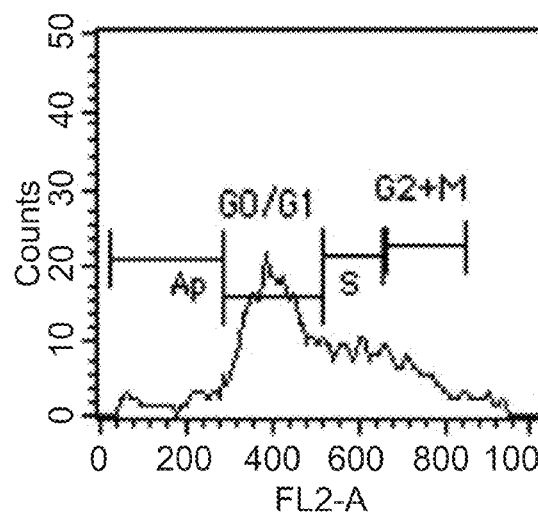
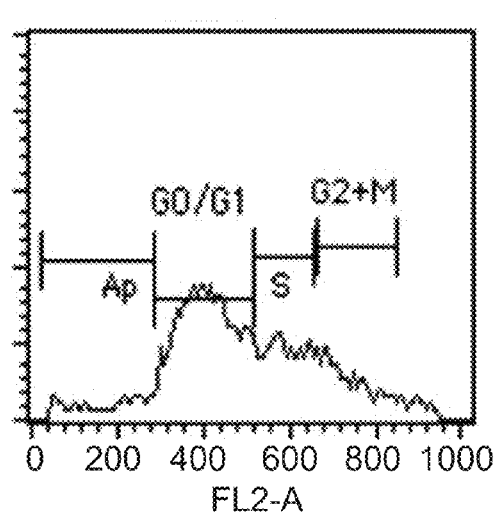
Fig. 15g
Fig. 15h Fig. 16a  Fig. 16b
H1299-R175H
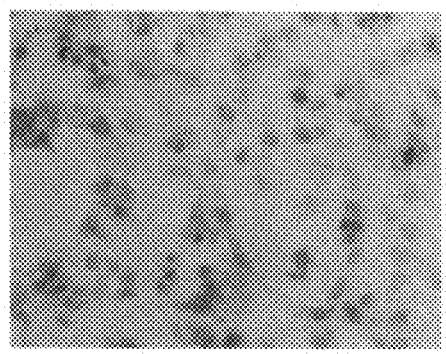 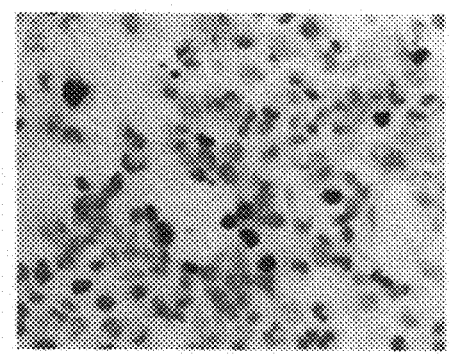
H1299
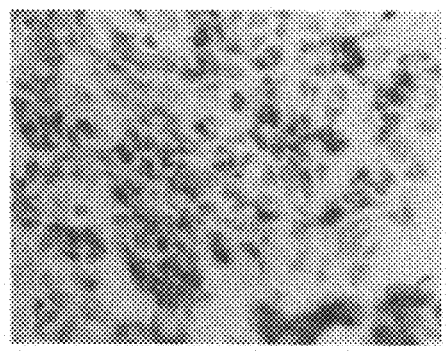 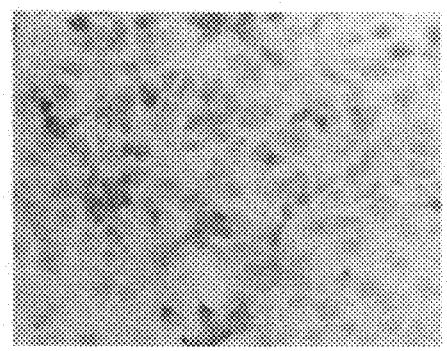
Fig. 16c  Fig. 16d Fig. 18a  Internalization peptide: PEP
EFGACRGDCLGA
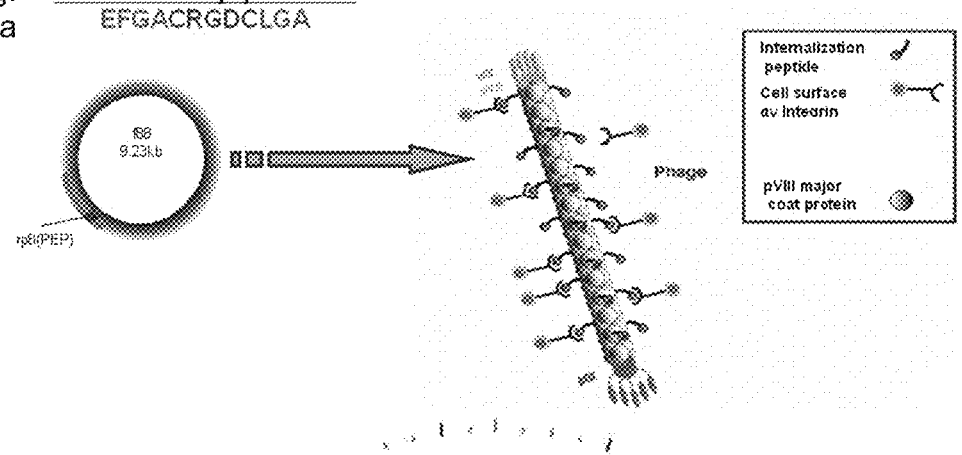
Fig. 18b
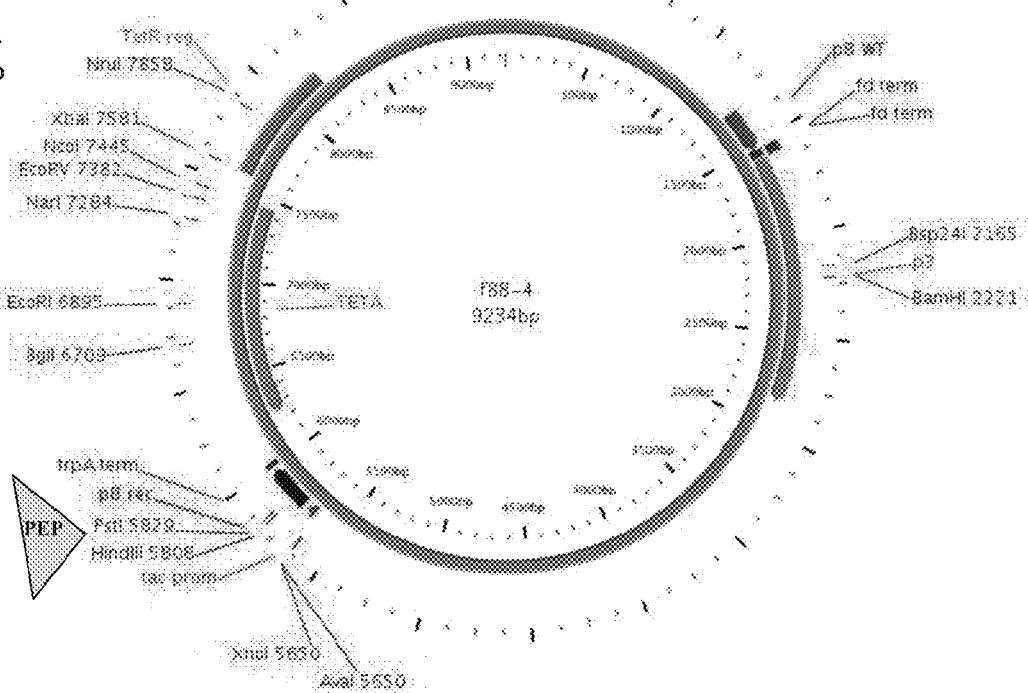

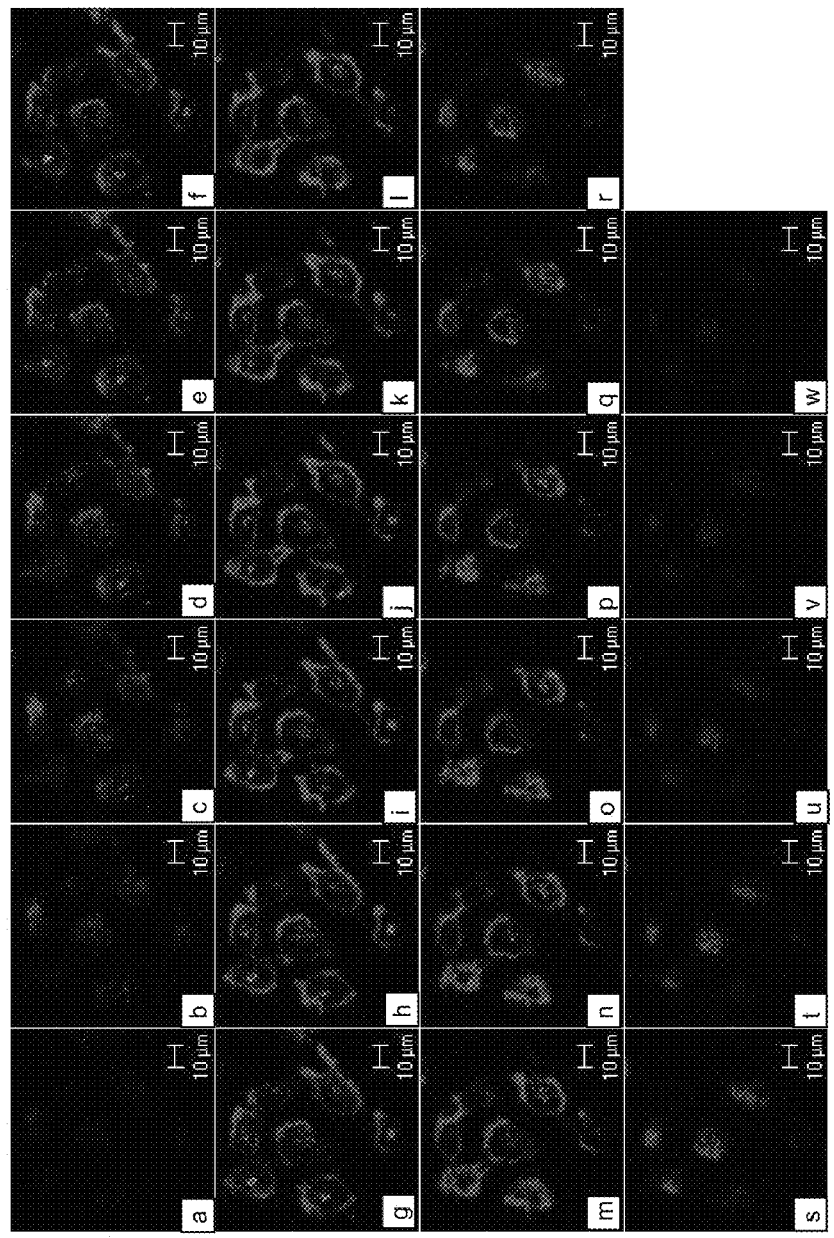
Figs. 20a-w

```
                              SEQUENCE LISTING

<160> NUMBER OF SEQ ID NOS: 136

<210> SEQ ID NO 1
<211> LENGTH: 6
<212> TYPE: PRT
<213> ORGANISM: Artificial sequence
<220> FEATURE:
<223> OTHER INFORMATION: Synthetic peptide of the common epitope of
      mutant p53

<400> SEQUENCE: 1

Phe Arg His Ser Val Val
1               5

<210> SEQ ID NO 2
<211> LENGTH: 16
<212> TYPE: PRT
<213> ORGANISM: Artificial sequence
<220> FEATURE:
<223> OTHER INFORMATION: A peptide corresponding with amino acids 1-16
      of Beta amyloid

<400> SEQUENCE: 2

Asp Ala Glu Phe Arg His Asp Ser Gly Tyr Glu Val His His Gln Lys
1               5                   10                  15

<210> SEQ ID NO 3
<211> LENGTH: 9
<212> TYPE: PRT
<213> ORGANISM: Artificial sequence
<220> FEATURE:
<223> OTHER INFORMATION: A peptide corresponding with amino acids
      144-153 of the multiple antigen peptide presenting the human
      prion protein

<400> SEQUENCE: 3

Asp Tyr Glu Asp Arg Tyr Tyr Arg Glu
1               5

<210> SEQ ID NO 4
<211> LENGTH: 9
<212> TYPE: PRT
<213> ORGANISM: Artificial sequence
<220> FEATURE:
<223> OTHER INFORMATION: A peptide corresponding to a prostate cancer
      antigen

<400> SEQUENCE: 4

Ile Leu Leu Trp Gln Pro Ile Pro Val
```

```
1               5

<210> SEQ ID NO 5
<211> LENGTH: 9
<212> TYPE: PRT
<213> ORGANISM: Artificial sequence
<220> FEATURE:
<223> OTHER INFORMATION: Variable heavy chain

<400> SEQUENCE: 5

Phe Ser Gly Tyr Trp Met His Trp Val
1               5

<210> SEQ ID NO 6
<211> LENGTH: 17
<212> TYPE: PRT
<213> ORGANISM: Artificial sequence
<220> FEATURE:
<223> OTHER INFORMATION: Variable heavy chain

<400> SEQUENCE: 6

Glu Ile Ser Gly Ser Gly Asp Ser Thr His Tyr Gly Asp Ser Val Lys
1               5                   10                  15

Gly

<210> SEQ ID NO 7
<211> LENGTH: 9
<212> TYPE: PRT
<213> ORGANISM: Artificial sequence
<220> FEATURE:
<223> OTHER INFORMATION: Variable heavy chain

<400> SEQUENCE: 7

Gly Arg Asn Gly Ser Leu Asp Tyr Trp
1               5

<210> SEQ ID NO 8
<211> LENGTH: 15
<212> TYPE: PRT
<213> ORGANISM: Artificial sequence
<220> FEATURE:
<223> OTHER INFORMATION: Variable light chain

<400> SEQUENCE: 8

Thr Gly Ser Ser Ser Asn Ile Gly Ala Asp Tyr Asp Val His Trp
1               5                   10                  15

<210> SEQ ID NO 9
<211> LENGTH: 11
<212> TYPE: PRT
<213> ORGANISM: Artificial sequence
<220> FEATURE:
<223> OTHER INFORMATION: Variable light chain

<400> SEQUENCE: 9

Ile Tyr Asp Asn His Lys Arg Pro Ser Gly Val
1               5                   10

<210> SEQ ID NO 10
<211> LENGTH: 17
<212> TYPE: PRT
<213> ORGANISM: Artificial sequence
<220> FEATURE:
<223> OTHER INFORMATION: Variable light chain

<400> SEQUENCE: 10

Cys Gln Ser Trp Asp Asn Ser Ala Val Val Phe Gly Gly Gly Thr Gln
```

<210> SEQ ID NO 11
<211> LENGTH: 15
<212> TYPE: PRT
<213> ORGANISM: Artificial sequence
<220> FEATURE:
<223> OTHER INFORMATION: Variable light chain

<400> SEQUENCE: 11

Thr Gly Ser Ser Ser Asn Ile Gly Ala Gly Tyr Asp Val His Trp
1               5                   10                  15

<210> SEQ ID NO 12
<211> LENGTH: 11
<212> TYPE: PRT
<213> ORGANISM: Artificial sequence
<220> FEATURE:
<223> OTHER INFORMATION: Variable light chain

<400> SEQUENCE: 12

Ile Tyr Ser Asn His His Arg Pro Ser Gly Val
1               5                   10

<210> SEQ ID NO 13
<211> LENGTH: 19
<212> TYPE: PRT
<213> ORGANISM: Artificial sequence
<220> FEATURE:
<223> OTHER INFORMATION: Variable light chain

<400> SEQUENCE: 13

Cys Gln Val Trp Asp Ser Ser Ser Asp His Val Val Phe Gly Gly Gly
1               5                   10                  15

Thr Gln Leu

<210> SEQ ID NO 14
<211> LENGTH: 15
<212> TYPE: PRT
<213> ORGANISM: Artificial sequence
<220> FEATURE:
<223> OTHER INFORMATION: Variable light chain

<400> SEQUENCE: 14

Thr Gly Ser Ser Ser Asn Ile Gly Ala Gly Tyr Asp Val His Trp
1               5                   10                  15

<210> SEQ ID NO 15
<211> LENGTH: 11
<212> TYPE: PRT
<213> ORGANISM: Artificial sequence
<220> FEATURE:
<223> OTHER INFORMATION: Variable light chain

<400> SEQUENCE: 15

Ile Tyr Asp Asn Ser His Arg Pro Ser Gly Val
1               5                   10

<210> SEQ ID NO 16
<211> LENGTH: 19
<212> TYPE: PRT
<213> ORGANISM: Artificial sequence
<220> FEATURE:
<223> OTHER INFORMATION: Variable light chain

<400> SEQUENCE: 16

```
Cys Gln Val Trp Asp Ser Ser Glu His Val Glu Phe Gly Gly Gly
1               5                   10                  15

Thr Gln Leu

<210> SEQ ID NO 17
<211> LENGTH: 15
<212> TYPE: PRT
<213> ORGANISM: Artificial sequence
<220> FEATURE:
<223> OTHER INFORMATION: Variable light chain

<400> SEQUENCE: 17

Thr Gly Thr Thr Ser Asn Ile Gly Ala Gly Tyr Asp Val His Trp
1               5                   10                  15

<210> SEQ ID NO 18
<211> LENGTH: 11
<212> TYPE: PRT
<213> ORGANISM: Artificial sequence
<220> FEATURE:
<223> OTHER INFORMATION: Variable light chain

<400> SEQUENCE: 18

Ile Tyr Glu Asn Asp Lys Arg Pro Ser Gly Val
1               5                   10

<210> SEQ ID NO 19
<211> LENGTH: 20
<212> TYPE: PRT
<213> ORGANISM: Artificial sequence
<220> FEATURE:
<223> OTHER INFORMATION: Variable light chain

<400> SEQUENCE: 19

Cys Ala Ser Trp Asp Asp Ser Leu Asn Gly His Val Val Phe Gly Gly
1               5                   10                  15

Gly Thr Gln Leu
            20

<210> SEQ ID NO 20
<211> LENGTH: 15
<212> TYPE: PRT
<213> ORGANISM: Artificial sequence
<220> FEATURE:
<223> OTHER INFORMATION: Variable light chain

<400> SEQUENCE: 20

Thr Gly Ser Ser Ser Asn Ile Gly Ala Asp Tyr Asp Val His Trp
1               5                   10                  15

<210> SEQ ID NO 21
<211> LENGTH: 11
<212> TYPE: PRT
<213> ORGANISM: Artificial sequence
<220> FEATURE:
<223> OTHER INFORMATION: Variable light chain

<400> SEQUENCE: 21

Ile Tyr Gly Asn Tyr His Arg Pro Ser Gly Val
1               5                   10

<210> SEQ ID NO 22
<211> LENGTH: 20
<212> TYPE: PRT
<213> ORGANISM: Artificial sequence
<220> FEATURE:
```

<223> OTHER INFORMATION: Variable light chain

<400> SEQUENCE: 22

Cys Ser Ser Trp Asp Asp Ser Gln Ser Gly His Val Ala Phe Gly Gly
1               5                   10                  15

Gly Thr Gln Val
            20

<210> SEQ ID NO 23
<211> LENGTH: 19
<212> TYPE: PRT
<213> ORGANISM: Artificial sequence
<220> FEATURE:
<223> OTHER INFORMATION: Variable light chain

<400> SEQUENCE: 23

Cys Ala Ala Trp Asp Asp Ser Leu Ser Gly Pro Val Phe Gly Gly Gly
1               5                   10                  15

Thr Gln Val

<210> SEQ ID NO 24
<211> LENGTH: 15
<212> TYPE: PRT
<213> ORGANISM: Artificial sequence
<220> FEATURE:
<223> OTHER INFORMATION: Variable light chain

<400> SEQUENCE: 24

Thr Gly Ser Ser Ser Asn Ile Gly Ala Asp Tyr Asp Val His Trp
1               5                   10                  15

<210> SEQ ID NO 25
<211> LENGTH: 11
<212> TYPE: PRT
<213> ORGANISM: Artificial sequence
<220> FEATURE:
<223> OTHER INFORMATION: Variable light chain

<400> SEQUENCE: 25

Ile Tyr Asp Asn Asp Lys Arg Pro Ser Gly Val
1               5                   10

<210> SEQ ID NO 26
<211> LENGTH: 19
<212> TYPE: PRT
<213> ORGANISM: Artificial sequence
<220> FEATURE:
<223> OTHER INFORMATION: Variable light chain

<400> SEQUENCE: 26

Cys Ala Val Trp Asp Asp Ser Leu Asn Ala Val Val Phe Gly Gly Gly
1               5                   10                  15

Thr Lys Val

<210> SEQ ID NO 27
<211> LENGTH: 15
<212> TYPE: PRT
<213> ORGANISM: Artificial sequence
<220> FEATURE:
<223> OTHER INFORMATION: Variable light chain

<400> SEQUENCE: 27

Thr Gly Ser Ser Ala Asn Ile Gly Ala Gly Tyr Asp Val His Trp
1               5                   10                  15

```
<210> SEQ ID NO 28
<211> LENGTH: 11
<212> TYPE: PRT
<213> ORGANISM: Artificial sequence
<220> FEATURE:
<223> OTHER INFORMATION: Variable light chain

<400> SEQUENCE: 28

Ile Tyr Asp Asn Asp Lys Arg Pro Ser Gly Val
1               5                   10

<210> SEQ ID NO 29
<211> LENGTH: 19
<212> TYPE: PRT
<213> ORGANISM: Artificial sequence
<220> FEATURE:
<223> OTHER INFORMATION: Variable light chain

<400> SEQUENCE: 29

Cys Ala Ala Trp Asp Asp Arg Leu Ser Gly Val Val Phe Gly Gly Gly
1               5                   10                  15

Thr Lys Val

<210> SEQ ID NO 30
<211> LENGTH: 15
<212> TYPE: PRT
<213> ORGANISM: Artificial sequence
<220> FEATURE:
<223> OTHER INFORMATION: Variable light chain

<400> SEQUENCE: 30

Thr Gly Asn Ser Ser Asn Ile Gly Ala Gly Tyr Asp Val His Trp
1               5                   10                  15

<210> SEQ ID NO 31
<211> LENGTH: 11
<212> TYPE: PRT
<213> ORGANISM: Artificial sequence
<220> FEATURE:
<223> OTHER INFORMATION: Variable light chain

<400> SEQUENCE: 31

Ile Tyr Ser Asn Asn Gln Arg Pro Ser Gly Val
1               5                   10

<210> SEQ ID NO 32
<211> LENGTH: 19
<212> TYPE: PRT
<213> ORGANISM: Artificial sequence
<220> FEATURE:
<223> OTHER INFORMATION: Variable light chain

<400> SEQUENCE: 32

Cys Ala Ala Trp Asp Asp Ser Leu Asn Gly Pro Val Phe Gly Gly Gly
1               5                   10                  15

Thr Gln Val

<210> SEQ ID NO 33
<211> LENGTH: 15
<212> TYPE: PRT
<213> ORGANISM: Artificial sequence
<220> FEATURE:
<223> OTHER INFORMATION: Variable light chain

<400> SEQUENCE: 33

Thr Gly Ser Ser Ser Asn Ile Gly Ala Gly Tyr Asp Val His Trp
1               5                   10                  15
```

<210> SEQ ID NO 34
<211> LENGTH: 11
<212> TYPE: PRT
<213> ORGANISM: Artificial sequence
<220> FEATURE:
<223> OTHER INFORMATION: Variable light chain

<400> SEQUENCE: 34

Ile Tyr Ala Asn Asn Asn Arg Pro Ser Gly Val
1               5                   10

<210> SEQ ID NO 35
<211> LENGTH: 19
<212> TYPE: PRT
<213> ORGANISM: Artificial sequence
<220> FEATURE:
<223> OTHER INFORMATION: Variable light chain

<400> SEQUENCE: 35

Cys Ala Ala Trp Asp Asp Asn Leu Asn Gly Leu Val Phe Gly Gly Gly
1               5                   10                  15

Thr Gln Leu

<210> SEQ ID NO 36
<211> LENGTH: 15
<212> TYPE: PRT
<213> ORGANISM: Artificial sequence
<220> FEATURE:
<223> OTHER INFORMATION: Variable light chain

<400> SEQUENCE: 36

Thr Gly Asn Ser Ser Asn Ile Gly Ala Gly Tyr Asp Val His Trp
1               5                   10                  15

<210> SEQ ID NO 37
<211> LENGTH: 11
<212> TYPE: PRT
<213> ORGANISM: Artificial sequence
<220> FEATURE:
<223> OTHER INFORMATION: Variable light chain

<400> SEQUENCE: 37

Ile Tyr Ser Asn Asn Gln Arg Pro Ser Gly Val
1               5                   10

<210> SEQ ID NO 38
<211> LENGTH: 19
<212> TYPE: PRT
<213> ORGANISM: Artificial sequence
<220> FEATURE:
<223> OTHER INFORMATION: Variable light chain

<400> SEQUENCE: 38

Cys Ala Ala Trp Asp Asp Ser Leu Ser Ser Val Val Phe Gly Gly Gly
1               5                   10                  15

Thr Lys Leu

<210> SEQ ID NO 39
<211> LENGTH: 15
<212> TYPE: PRT
<213> ORGANISM: Artificial sequence
<220> FEATURE:
<223> OTHER INFORMATION: Variable light chain

<400> SEQUENCE: 39

```
Ser Gly Thr Ser Ser Asn Ile Gly Ala Asp Tyr Asp Val His Trp
1               5                   10                  15

<210> SEQ ID NO 40
<211> LENGTH: 11
<212> TYPE: PRT
<213> ORGANISM: Artificial sequence
<220> FEATURE:
<223> OTHER INFORMATION: Variable light chain

<400> SEQUENCE: 40

Ile Tyr Asp Asn Asn Lys Arg Pro Ser Gly Val
1               5                   10

<210> SEQ ID NO 41
<211> LENGTH: 19
<212> TYPE: PRT
<213> ORGANISM: Artificial sequence
<220> FEATURE:
<223> OTHER INFORMATION: Variable light chain

<400> SEQUENCE: 41

Cys Ala Ala Trp Asp Ser Ser Leu Ser Ser Val Val Phe Gly Gly Gly
1               5                   10                  15

Thr Gln Leu

<210> SEQ ID NO 42
<211> LENGTH: 15
<212> TYPE: PRT
<213> ORGANISM: Artificial sequence
<220> FEATURE:
<223> OTHER INFORMATION: Variable light chain

<400> SEQUENCE: 42

Ser Gly Ser Ser Ser Asn Ile Gly Ala Asp Tyr Asp Val His Trp
1               5                   10                  15

<210> SEQ ID NO 43
<211> LENGTH: 11
<212> TYPE: PRT
<213> ORGANISM: Artificial sequence
<220> FEATURE:
<223> OTHER INFORMATION: Variable light chain

<400> SEQUENCE: 43

Ile Tyr Ser Asn Asn Gln Arg Pro Ser Gly Val
1               5                   10

<210> SEQ ID NO 44
<211> LENGTH: 19
<212> TYPE: PRT
<213> ORGANISM: Artificial sequence
<220> FEATURE:
<223> OTHER INFORMATION: Variable light chain

<400> SEQUENCE: 44

Cys Ala Ala Trp Asp Asp Ser Leu Asn Gly Tyr Val Phe Gly Thr Gly
1               5                   10                  15

Thr Lys Leu

<210> SEQ ID NO 45
<211> LENGTH: 15
<212> TYPE: PRT
<213> ORGANISM: Artificial sequence
<220> FEATURE:
<223> OTHER INFORMATION: Variable light chain
```

-continued

```
<400> SEQUENCE: 45

Ser Gly Ser Ser Ser Asn Ile Gly Ala Gly Tyr Asp Val His Trp
1               5                   10                  15

<210> SEQ ID NO 46
<211> LENGTH: 11
<212> TYPE: PRT
<213> ORGANISM: Artificial sequence
<220> FEATURE:
<223> OTHER INFORMATION: Variable light chain

<400> SEQUENCE: 46

Ile Tyr Gly Asn Thr Asn Arg Pro Ser Gly Val
1               5                   10

<210> SEQ ID NO 47
<211> LENGTH: 19
<212> TYPE: PRT
<213> ORGANISM: Artificial sequence
<220> FEATURE:
<223> OTHER INFORMATION: Variable light chain

<400> SEQUENCE: 47

Cys Gln Ser Phe Asp Ser Thr Leu Ser Gly Pro Val Phe Gly Gly
1               5                   10                  15

Thr Lys Val

<210> SEQ ID NO 48
<211> LENGTH: 15
<212> TYPE: PRT
<213> ORGANISM: Artificial sequence
<220> FEATURE:
<223> OTHER INFORMATION: Variable light chain

<400> SEQUENCE: 48

Ser Gly Ser Ser Ser Asn Ile Gly Ala Gly Tyr Asp Val His Trp
1               5                   10                  15

<210> SEQ ID NO 49
<211> LENGTH: 11
<212> TYPE: PRT
<213> ORGANISM: Artificial sequence
<220> FEATURE:
<223> OTHER INFORMATION: Variable light chain

<400> SEQUENCE: 49

Ile Tyr Gly Asn Thr Asn Arg Pro Ser Gly Val
1               5                   10

<210> SEQ ID NO 50
<211> LENGTH: 19
<212> TYPE: PRT
<213> ORGANISM: Artificial sequence
<220> FEATURE:
<223> OTHER INFORMATION: Variable light chain

<400> SEQUENCE: 50

Cys Ala Ala Trp Asp Asp Ser Leu Asn Gly Leu Val Phe Gly Gly
1               5                   10                  15

Thr Gln Val

<210> SEQ ID NO 51
<211> LENGTH: 15
<212> TYPE: PRT
<213> ORGANISM: Artificial sequence
<220> FEATURE:
```

<223> OTHER INFORMATION: Variable light chain

<400> SEQUENCE: 51

Ser Gly Ser Asn Ser Asn Ile Gly Ala Gly Tyr Asp Val Gln Trp
1               5                   10                  15

<210> SEQ ID NO 52
<211> LENGTH: 11
<212> TYPE: PRT
<213> ORGANISM: Artificial sequence
<220> FEATURE:
<223> OTHER INFORMATION: Variable light chain

<400> SEQUENCE: 52

Ile Tyr Ala Asn Ser Asn Arg Pro Ser Gly Val
1               5                   10

<210> SEQ ID NO 53
<211> LENGTH: 19
<212> TYPE: PRT
<213> ORGANISM: Artificial sequence
<220> FEATURE:
<223> OTHER INFORMATION: Variable light chain

<400> SEQUENCE: 53

Cys Gly Val Trp Asp Asp Ser Leu Asn Gly Pro Val Phe Gly Gly Gly
1               5                   10                  15

Thr Pro Val

<210> SEQ ID NO 54
<211> LENGTH: 14
<212> TYPE: PRT
<213> ORGANISM: Artificial sequence
<220> FEATURE:
<223> OTHER INFORMATION: Variable light chain

<400> SEQUENCE: 54

Thr Gly Gly Ser Ser Asn Ile Gly Asn His His Val Ser Trp
1               5                   10

<210> SEQ ID NO 55
<211> LENGTH: 11
<212> TYPE: PRT
<213> ORGANISM: Artificial sequence
<220> FEATURE:
<223> OTHER INFORMATION: Variable light chain

<400> SEQUENCE: 55

Ile Tyr Gly Asn Thr Asn Arg Pro Ser Gly Val
1               5                   10

<210> SEQ ID NO 56
<211> LENGTH: 19
<212> TYPE: PRT
<213> ORGANISM: Artificial sequence
<220> FEATURE:
<223> OTHER INFORMATION: Variable light chain

<400> SEQUENCE: 56

Cys Gln Val Trp Asp Ser Ser Ser Asp His Val Val Phe Gly Gly Gly
1               5                   10                  15

Thr Lys Val

<210> SEQ ID NO 57
<211> LENGTH: 14
<212> TYPE: PRT

```
<213> ORGANISM: Artificial sequence
<220> FEATURE:
<223> OTHER INFORMATION: Variable light chain

<400> SEQUENCE: 57

Ser Gly Thr Ser Ser Asn Ile Gly Ser His Thr Val His Trp
1               5                   10

<210> SEQ ID NO 58
<211> LENGTH: 11
<212> TYPE: PRT
<213> ORGANISM: Artificial sequence
<220> FEATURE:
<223> OTHER INFORMATION: Variable light chain

<400> SEQUENCE: 58

Ile Tyr Glu Val Asn Lys Arg Pro Ser Gly Val
1               5                   10

<210> SEQ ID NO 59
<211> LENGTH: 19
<212> TYPE: PRT
<213> ORGANISM: Artificial sequence
<220> FEATURE:
<223> OTHER INFORMATION: Variable light chain

<400> SEQUENCE: 59

Cys Gln Ser Tyr Asp Ser Ser Leu Ser Ala Val Val Phe Gly Gly Gly
1               5                   10                  15

Thr Gln Val

<210> SEQ ID NO 60
<211> LENGTH: 14
<212> TYPE: PRT
<213> ORGANISM: Artificial sequence
<220> FEATURE:
<223> OTHER INFORMATION: Variable light chain

<400> SEQUENCE: 60

Thr Gly Gly Arg Phe Asn Ile Gly Asp Tyr Ala Val His Trp
1               5                   10

<210> SEQ ID NO 61
<211> LENGTH: 11
<212> TYPE: PRT
<213> ORGANISM: Artificial sequence
<220> FEATURE:
<223> OTHER INFORMATION: Variable light chain

<400> SEQUENCE: 61

Ile Tyr Asp Asn Asp Arg Arg Pro Ser Gly Val
1               5                   10

<210> SEQ ID NO 62
<211> LENGTH: 19
<212> TYPE: PRT
<213> ORGANISM: Artificial sequence
<220> FEATURE:
<223> OTHER INFORMATION: Variable light chain

<400> SEQUENCE: 62

Cys Ala Ala Trp Asp Asp Ser Leu Asp Gly Leu Val Phe Gly Gly Gly
1               5                   10                  15

Thr Gln Leu

<210> SEQ ID NO 63
```

```
<211> LENGTH: 14
<212> TYPE: PRT
<213> ORGANISM: Artificial sequence
<220> FEATURE:
<223> OTHER INFORMATION: Variable light chain

<400> SEQUENCE: 63

Thr Gly Gly Arg Phe Asn Ile Gly Asp Tyr Ala Val His Trp
1               5                   10

<210> SEQ ID NO 64
<211> LENGTH: 11
<212> TYPE: PRT
<213> ORGANISM: Artificial sequence
<220> FEATURE:
<223> OTHER INFORMATION: Variable light chain

<400> SEQUENCE: 64

Ile Tyr Asp Asn Asp Arg Arg Pro Ser Gly Val
1               5                   10

<210> SEQ ID NO 65
<211> LENGTH: 19
<212> TYPE: PRT
<213> ORGANISM: Artificial sequence
<220> FEATURE:
<223> OTHER INFORMATION: Variable light chain

<400> SEQUENCE: 65

Cys Gln Ser Phe Asp Ser Thr Leu Ser Gly Pro Val Phe Gly Gly Gly
1               5                   10                  15

Thr Lys Val

<210> SEQ ID NO 66
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 66

Thr Gly Ser Ser Ser Asn Ile Gly Ala Asp Tyr Asp Val His Trp
1               5                   10                  15

<210> SEQ ID NO 67
<211> LENGTH: 11
<212> TYPE: PRT
<213> ORGANISM: Artificial sequence
<220> FEATURE:
<223> OTHER INFORMATION: Light chain Unique CDR

<400> SEQUENCE: 67

Ile Tyr Asp Asn His Lys Arg Pro Ser Gly Val
1               5                   10

<210> SEQ ID NO 68
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 68

Ser Trp Asp Asn Ser Ala Val Val Phe Gly Gly Gly Thr Gln Leu
1               5                   10                  15

<210> SEQ ID NO 69
```

```
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 69

Thr Gly Ser Ser Ser Asn Ile Gly Ala Gly Tyr Asp Val His Trp
1               5                   10                  15

<210> SEQ ID NO 70
<211> LENGTH: 11
<212> TYPE: PRT
<213> ORGANISM: Artificial sequence
<220> FEATURE:
<223> OTHER INFORMATION: Light chain Unique CDR

<400> SEQUENCE: 70

Ile Tyr Ser Asn His His Arg Pro Ser Gly Val
1               5                   10

<210> SEQ ID NO 71
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 71

Gln Val Trp Asp Ser Ser Ser Asp His Val Val Phe Gly Gly Gly Thr
1               5                   10                  15

Gln Leu

<210> SEQ ID NO 72
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 72

Thr Gly Thr Thr Ser Asn Ile Gly Ala Gly Tyr Asp Val His Trp
1               5                   10                  15

<210> SEQ ID NO 73
<211> LENGTH: 11
<212> TYPE: PRT
<213> ORGANISM: Artificial sequence
<220> FEATURE:
<223> OTHER INFORMATION: Light chain Unique CDR

<400> SEQUENCE: 73

Ile Tyr Asp Asn Ser His Arg Pro Ser Gly Val
1               5                   10

<210> SEQ ID NO 74
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 74

Gln Val Trp Asp Ser Ser Ser Glu His Val Glu Phe Gly Gly Gly Thr
1               5                   10                  15

Gln Leu
```

<210> SEQ ID NO 75
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 75

Thr Gly Ser Ser Ala Asn Ile Gly Ala Gly Tyr Asp Val His Trp
1               5                   10                  15

<210> SEQ ID NO 76
<211> LENGTH: 10
<212> TYPE: PRT
<213> ORGANISM: Artificial sequence
<220> FEATURE:
<223> OTHER INFORMATION: Light chain Unique CDR

<400> SEQUENCE: 76

Tyr Glu Asn Asp Lys Arg Pro Ser Gly Val
1               5                   10

<210> SEQ ID NO 77
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 77

Ala Ser Trp Asp Asp Ser Leu Asn Gly His Val Val Phe Gly Gly Gly
1               5                   10                  15

Thr Gln Leu

<210> SEQ ID NO 78
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 78

Thr Gly Asn Ser Ser Asn Ile Gly Ala Gly Tyr Asp Val His Trp
1               5                   10                  15

<210> SEQ ID NO 79
<211> LENGTH: 10
<212> TYPE: PRT
<213> ORGANISM: Artificial sequence
<220> FEATURE:
<223> OTHER INFORMATION: Light chain Unique CDR

<400> SEQUENCE: 79

Tyr Gly Asn Tyr His Arg Pro Ser Gly Val
1               5                   10

<210> SEQ ID NO 80
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 80

Ser Ser Trp Asp Asp Ser Gln Ser Gly His Val Ala Phe Gly Gly Gly
1               5                   10                  15

Thr Gln Val

<210> SEQ ID NO 81
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 81

Ser Gly Thr Ser Ser Asn Ile Gly Ala Asp Tyr Asp Val His Trp
1               5                   10                  15

<210> SEQ ID NO 82
<211> LENGTH: 10
<212> TYPE: PRT
<213> ORGANISM: Artificial sequence
<220> FEATURE:
<223> OTHER INFORMATION: Light chain Unique CDR

<400> SEQUENCE: 82

Tyr Asp Asn Asp Lys Arg Pro Ser Gly Val
1               5                   10

<210> SEQ ID NO 83
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 83

Ala Ala Trp Asp Asp Ser Leu Ser Gly Pro Val Phe Gly Gly Gly Thr
1               5                   10                  15

Gln Val

<210> SEQ ID NO 84
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 84

Ser Gly Ser Ser Ser Asn Ile Gly Ala Asp Tyr Asp Val His Trp
1               5                   10                  15

<210> SEQ ID NO 85
<211> LENGTH: 10
<212> TYPE: PRT
<213> ORGANISM: Artificial sequence
<220> FEATURE:
<223> OTHER INFORMATION: Light chain Unique CDR

<400> SEQUENCE: 85

Tyr Ser Asn Asn Gln Arg Pro Ser Gly Val
1               5                   10

<210> SEQ ID NO 86
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 86

Ala Val Trp Asp Asp Ser Leu Asn Ala Val Val Phe Gly Gly Gly Thr

Lys Val

<210> SEQ ID NO 87
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 87

Ser Gly Ser Ser Ser Asn Ile Gly Ala Gly Tyr Asp Val His Trp
1               5                   10                  15

<210> SEQ ID NO 88
<211> LENGTH: 9
<212> TYPE: PRT
<213> ORGANISM: Artificial sequence
<220> FEATURE:
<223> OTHER INFORMATION: Light chain Unique CDR

<400> SEQUENCE: 88

Ala Asn Asn Asn Arg Pro Ser Gly Val
1               5

<210> SEQ ID NO 89
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 89

Ala Ala Trp Asp Asp Arg Leu Ser Gly Val Val Phe Gly Gly Gly Thr
1               5                   10                  15

Lys Val

<210> SEQ ID NO 90
<211> LENGTH: 15
<212> TYPE: PRT
<213> ORGANISM: Artificial sequence
<220> FEATURE:
<223> OTHER INFORMATION: Light chain Unique CDR

<400> SEQUENCE: 90

Ser Gly Ser Asn Ser Asn Ile Gly Ala Gly Tyr Asp Val Gln Trp
1               5                   10                  15

<210> SEQ ID NO 91
<211> LENGTH: 10
<212> TYPE: PRT
<213> ORGANISM: Artificial sequence
<220> FEATURE:
<223> OTHER INFORMATION: Light chain Unique CDR

<400> SEQUENCE: 91

Tyr Asp Asn Asn Lys Arg Pro Ser Gly Val
1               5                   10

<210> SEQ ID NO 92
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 92

```
Ala Ala Trp Asp Asp Ser Leu Asn Gly Pro Val Phe Gly Gly Thr
1               5                   10                  15

Gln Val

<210> SEQ ID NO 93
<211> LENGTH: 14
<212> TYPE: PRT
<213> ORGANISM: Artificial sequence
<220> FEATURE:
<223> OTHER INFORMATION: Light chain Unique CDR

<400> SEQUENCE: 93

Thr Gly Gly Ser Ser Asn Ile Gly Asn His His Val Ser Trp
1               5                   10

<210> SEQ ID NO 94
<211> LENGTH: 9
<212> TYPE: PRT
<213> ORGANISM: Artificial sequence
<220> FEATURE:
<223> OTHER INFORMATION: Light chain Unique CDR

<400> SEQUENCE: 94

Gly Asn Thr Asn Arg Pro Ser Gly Val
1               5

<210> SEQ ID NO 95
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 95

Ala Ala Trp Asp Asp Asn Leu Asn Gly Leu Val Phe Gly Gly Thr
1               5                   10                  15

Gln Leu

<210> SEQ ID NO 96
<211> LENGTH: 14
<212> TYPE: PRT
<213> ORGANISM: Artificial sequence
<220> FEATURE:
<223> OTHER INFORMATION: Light chain Unique CDR

<400> SEQUENCE: 96

Ser Gly Thr Ser Ser Asn Ile Gly Ser His Thr Val His Trp
1               5                   10

<210> SEQ ID NO 97
<211> LENGTH: 9
<212> TYPE: PRT
<213> ORGANISM: Artificial sequence
<220> FEATURE:
<223> OTHER INFORMATION: Light chain Unique CDR

<400> SEQUENCE: 97

Ala Asn Ser Asn Arg Pro Ser Gly Val
1               5

<210> SEQ ID NO 98
<211> LENGTH: 17
<212> TYPE: PRT
<213> ORGANISM: Artificial sequence
<220> FEATURE:
<223> OTHER INFORMATION: Light chain Unique CDR
```

<400> SEQUENCE: 98

Ala Trp Asp Asp Ser Leu Ser Ser Val Val Phe Gly Gly Gly Thr Lys
1               5                   10                  15

Leu

<210> SEQ ID NO 99
<211> LENGTH: 14
<212> TYPE: PRT
<213> ORGANISM: Artificial sequence
<220> FEATURE:
<223> OTHER INFORMATION: Light chain Unique CDR

<400> SEQUENCE: 99

Thr Gly Gly Arg Phe Asn Ile Gly Asp Tyr Ala Val His Trp
1               5                   10

<210> SEQ ID NO 100
<211> LENGTH: 9
<212> TYPE: PRT
<213> ORGANISM: Artificial sequence
<220> FEATURE:
<223> OTHER INFORMATION: Light chain Unique CDR

<400> SEQUENCE: 100

Glu Val Asn Lys Arg Pro Ser Gly Val
1               5

<210> SEQ ID NO 101
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 101

Ala Ala Trp Asp Ser Ser Leu Ser Ser Val Val Phe Gly Gly Gly Thr
1               5                   10                  15

Gln Leu

<210> SEQ ID NO 102
<211> LENGTH: 11
<212> TYPE: PRT
<213> ORGANISM: Artificial sequence
<220> FEATURE:
<223> OTHER INFORMATION: Light chain Unique CDR

<400> SEQUENCE: 102

Ile Tyr Asp Asn Asp Arg Arg Pro Ser Gly Val
1               5                   10

<210> SEQ ID NO 103
<211> LENGTH: 18
<212> TYPE: PRT
<213> ORGANISM: Artificial sequence
<220> FEATURE:
<223> OTHER INFORMATION: Light chain Unique CDR

<400> SEQUENCE: 103

Ala Ala Trp Asp Asp Ser Leu Asn Gly Tyr Val Phe Gly Thr Gly Thr
1               5                   10                  15

Lys Leu

<210> SEQ ID NO 104
<211> LENGTH: 19

```
<212> TYPE: PRT
<213> ORGANISM: Artificial sequence
<220> FEATURE:
<223> OTHER INFORMATION: Light chain Unique CDR

<400> SEQUENCE: 104

Cys Gln Ser Phe Asp Ser Thr Leu Ser Gly Pro Val Phe Gly Gly Gly
1               5                   10                  15

Thr Lys Val

<210> SEQ ID NO 105
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 105

Cys Ala Ala Trp Asp Asp Ser Leu Asn Gly Leu Val Phe Gly Gly Gly
1               5                   10                  15

Thr Gln Val

<210> SEQ ID NO 106
<211> LENGTH: 11
<212> TYPE: PRT
<213> ORGANISM: Artificial sequence
<220> FEATURE:
<223> OTHER INFORMATION: Light chain Unique CDR

<400> SEQUENCE: 106

Asn Gly Pro Val Phe Gly Gly Gly Thr Pro Val
1               5                   10

<210> SEQ ID NO 107
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 107

Cys Gln Val Trp Asp Ser Ser Ser Asp His Val Val Phe Gly Gly Gly
1               5                   10                  15

Thr Lys Val

<210> SEQ ID NO 108
<211> LENGTH: 12
<212> TYPE: PRT
<213> ORGANISM: Artificial sequence
<220> FEATURE:
<223> OTHER INFORMATION: Light chain Unique CDR

<400> SEQUENCE: 108

Leu Ser Ala Val Val Phe Gly Gly Gly Thr Gln Val
1               5                   10

<210> SEQ ID NO 109
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 109

Cys Ala Ala Trp Asp Asp Ser Leu Asp Gly Leu Val Phe Gly Gly Gly
1               5                   10                  15
```

Thr Gln Leu

<210> SEQ ID NO 110
<211> LENGTH: 19
<212> TYPE: PRT
<213> ORGANISM: Artificial sequence
<220> FEATURE:
<223> OTHER INFORMATION: Light chain Unique CDR

<400> SEQUENCE: 110

Cys Gln Ser Phe Asp Ser Thr Leu Ser Gly Pro Val Phe Gly Gly Gly
1               5                   10                  15

Thr Lys Val

<210> SEQ ID NO 111
<211> LENGTH: 15
<212> TYPE: PRT
<213> ORGANISM: Artificial sequence
<220> FEATURE:
<223> OTHER INFORMATION: Variable light chain

<400> SEQUENCE: 111

Thr Gly Ser Ser Ser Asn Ile Gly Ala Asp Tyr Asp Val His Trp
1               5                   10                  15

<210> SEQ ID NO 112
<211> LENGTH: 11
<212> TYPE: PRT
<213> ORGANISM: Artificial sequence
<220> FEATURE:
<223> OTHER INFORMATION: Variable light chain

<400> SEQUENCE: 112

Ile Tyr Asp Asn Asp Lys Arg Pro Ser Gly Val
1               5                   10

<210> SEQ ID NO 113
<211> LENGTH: 244
<212> TYPE: PRT
<213> ORGANISM: Artificial sequence
<220> FEATURE:
<223> OTHER INFORMATION: Single chain Fv

<400> SEQUENCE: 113

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
                20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly
        115                 120                 125

Ser Gly Gly Gly Gly Ser Asp Ile Val Leu Thr Gln Pro Pro Ser Ala
        130                 135                 140

Ser Gly Thr Pro Gly Gln Arg Val Thr Ile Ser Cys Ser Gly Thr Ser
145                 150                 155                 160

Ser Asn Ile Gly Ala Asp Tyr Asp Val His Trp Tyr Gln Gln Leu Pro
            165                 170                 175

Gly Lys Ala Pro Lys Leu Leu Ile Tyr Asp Asn Asn Lys Arg Pro Ser
            180                 185                 190

Gly Val Ser Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Ala Ala Trp Asp Ser Ser Leu Ser Ser Val Val Phe Gly Gly Gly Thr
225                 230                 235                 240

Gln Leu Thr Val

<210> SEQ ID NO 114
<211> LENGTH: 244
<212> TYPE: PRT
<213> ORGANISM: Artificial sequence
<220> FEATURE:
<223> OTHER INFORMATION: Single chain Fv

<400> SEQUENCE: 114

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Ala Gly Tyr Asp Val His Trp Tyr Gln Gln Leu Pro
            165                 170                 175

Gly Thr Ala Pro Lys Leu Leu Ile Tyr Gly Asn Thr Asn Arg Pro Ser
            180                 185                 190

Gly Val Ser Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Gln Ser Phe Asp Ser Thr Leu Ser Gly Pro Val Phe Gly Gly Gly Thr
225                 230                 235                 240

Lys Val Thr Val

<210> SEQ ID NO 115

```
<211> LENGTH: 243
<212> TYPE: PRT
<213> ORGANISM: Artificial sequence
<220> FEATURE:
<223> OTHER INFORMATION: Single chain Fv

<400> SEQUENCE: 115

Val Gln Leu Leu Glu Ser Gly Gly Gly Leu Val Gln Pro Gly Gly Ser
1               5                   10                  15

Pro Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Arg
145                 150                 155                 160

Phe Asn Ile Gly Asp Tyr Ala Val Asn Trp Tyr Gln Gln Leu Pro Gly
                165                 170                 175

Lys Ala Pro Lys Leu Leu Ile Tyr Asp Asn Asp Arg Arg Pro Ser Gly
            180                 185                 190

Val Ser Asp Arg Phe Ser Gly Ser Lys Ser Gly Thr Ser Ala Ser Leu
        195                 200                 205

Ala Ile Ser Gly Leu Arg Ser Glu Asp Glu Ala Asp Tyr Tyr Cys Ala
    210                 215                 220

Ala Trp Asp Asp Ser Leu Asp Gly Leu Val Phe Gly Gly Gly Thr Gln
225                 230                 235                 240

Leu Thr Val

<210> SEQ ID NO 116
<211> LENGTH: 242
<212> TYPE: PRT
<213> ORGANISM: Artificial sequence
<220> FEATURE:
<223> OTHER INFORMATION: Single chain Fv

<400> SEQUENCE: 116

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Asp Tyr Asp Val His Trp Tyr Gln Gln Leu Pro
                165                 170                 175

Gly Lys Ala Pro Lys Leu Leu Ile Tyr Asp Asn His Lys Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Gln Ser Trp Asp Asn Ser Ala Val Val Phe Gly Gly Thr Gln Leu
225                 230                 235                 240

Ser Val

<210> SEQ ID NO 117
<211> LENGTH: 244
<212> TYPE: PRT
<213> ORGANISM: Artificial sequence
<220> FEATURE:
<223> OTHER INFORMATION: Single chain Fv

<400> SEQUENCE: 117

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Asp Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Ser Asn His His Arg Pro Ser
            180                 185                 190

Gly Val Pro Asp Arg Phe Ser Gly Ser Lys Ser Gly Thr Ser Ala Ser
        195                 200                 205

```
Leu Ala Ile Ser Gly Leu Arg Ser Glu Asp Glu Ala Asp Tyr Tyr Cys
    210                 215                 220

Gln Val Trp Asp Ser Ser Asp His Val Val Phe Gly Gly Gly Thr
225                 230                 235                 240

Gln Leu Thr Val

<210> SEQ ID NO 118
<211> LENGTH: 244
<212> TYPE: PRT
<213> ORGANISM: Artificial sequence
<220> FEATURE:
<223> OTHER INFORMATION: Single chain Fv

<400> SEQUENCE: 118

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Ala Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Lys Ala Pro Lys Leu Leu Ile Tyr Asp Asn Ser His Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Gln Val Trp Asp Ser Ser Glu His Val Glu Phe Gly Gly Gly Thr
225                 230                 235                 240

Gln Leu Thr Val

<210> SEQ ID NO 119
<211> LENGTH: 245
<212> TYPE: PRT
<213> ORGANISM: Artificial sequence
<220> FEATURE:
<223> OTHER INFORMATION: Single chain Fv

<400> SEQUENCE: 119

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
```

```
                 20                  25                  30
Met His Trp Val Arg Gln Ala Pro Gly Lys Gly Leu Glu Trp Val Ser
         35                  40                  45
Glu Ile Ser Gly Ser Gly Asp Ser Thr His Tyr Gly Asp Ser Val Lys
         50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                 85                  90                  95
Arg Gly Arg Asn Gly Ser Leu Asp Tyr Trp Gly Gln Gly Thr Leu Val
                100                 105                 110
Thr Val Ser Ser Gly Ser Ala Gly Gly Gly Ser Gly Gly Gly Gly
             115                 120                 125
Ser Gly Gly Gly Gly Ser Asp Ile Val Leu Thr Gln Pro Pro Ser Ala
         130                 135                 140
Ser Gly Thr Pro Gly Gln Arg Val Thr Ile Ser Cys Thr Gly Thr Thr
145                 150                 155                 160
Ser Asn Ile Gly Ala Gly Tyr Asp Val His Trp Tyr Gln Gln Leu Pro
                165                 170                 175
Gly Thr Ala Pro Lys Leu Leu Ile Tyr Glu Asn Asp Lys Arg Pro Ser
                180                 185                 190
Gly Val Pro Asp Arg Phe Ser Gly Ser Lys Ser Gly Thr Ser Ala Ser
                195                 200                 205
Leu Ala Ile Ser Gly Leu Arg Ser Glu Asp Glu Ala Asp Tyr Tyr Cys
            210                 215                 220
Ala Ser Trp Asp Asp Ser Leu Asn Gly His Val Val Phe Gly Gly
225                 230                 235                 240
Thr Gln Leu Thr Val
            245

<210> SEQ ID NO 120
<211> LENGTH: 245
<212> TYPE: PRT
<213> ORGANISM: Artificial sequence
<220> FEATURE:
<223> OTHER INFORMATION: Single chain Fv

<400> SEQUENCE: 120

Val Gln Leu Leu Glu Ser Gly Gly Gly Leu Val Gln Pro Gly Gly Ser
1               5                  10                  15
Leu Arg Leu Ser Cys Ala Ala Ser Gly Phe Thr Phe Ser Gly Tyr Trp
                 20                  25                  30
Met His Trp Val Arg Gln Ala Pro Gly Lys Gly Leu Glu Trp Val Ser
         35                  40                  45
Glu Ile Ser Gly Ser Gly Asp Ser Thr His Tyr Gly Asp Ser Val Lys
         50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                 85                  90                  95
Arg Gly Arg Asn Gly Ser Leu Asp Tyr Trp Gly Gln Gly Thr Leu Val
                100                 105                 110
Thr Val Ser Ser Gly Ser Ala Gly Gly Gly Ser Gly Gly Gly Gly
             115                 120                 125
Ser Gly Gly Gly Gly Ser Asp Ile Val Leu Thr Gln Pro Pro Ser Ala
         130                 135                 140
```

Ser Gly Thr Pro Gly Gln Arg Val Thr Ile Ser Cys Thr Gly Ser Ser
145                 150                 155                 160

Ser Asn Ile Gly Ala Asp Tyr Asp Val His Trp Tyr Gln Gln Leu Pro
            165                 170                 175

Gly Lys Ala Pro Lys Leu Leu Ile Tyr Gly Asn Tyr His Arg Pro Ser
            180                 185                 190

Gly Val Pro Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Ser Ser Trp Asp Asp Ser Gln Ser Gly His Val Ala Phe Gly Gly Gly
225                 230                 235                 240

Thr Gln Val Thr Val
            245

<210> SEQ ID NO 121
<211> LENGTH: 244
<212> TYPE: PRT
<213> ORGANISM: Artificial sequence
<220> FEATURE:
<223> OTHER INFORMATION: Single chain Fv

<400> SEQUENCE: 121

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
            130                 135                 140

Ser Gly Thr Pro Gly Gln Arg Val Thr Ile Ser Cys Thr Gly Ser Ser
145                 150                 155                 160

Ser Asn Ile Gly Ala Asp Tyr Asp Val His Trp Tyr Gln Gln Leu Pro
            165                 170                 175

Gly Lys Ala Pro Lys Leu Leu Ile Tyr Asp Asn Asp Lys Arg Pro Ser
            180                 185                 190

Gly Val Pro Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Ala Ala Trp Asp Asp Ser Leu Ser Gly Pro Val Phe Gly Gly Gly Thr
225                 230                 235                 240

Gln Val Thr Val

```
-continued

<210> SEQ ID NO 122
<211> LENGTH: 244
<212> TYPE: PRT
<213> ORGANISM: Artificial sequence
<220> FEATURE:
<223> OTHER INFORMATION: Single chain Fv

<400> SEQUENCE: 122

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ala Asn Ile Gly Ala Gly Tyr Asp Val His Trp Tyr Gln Gln Leu Pro
                165                 170                 175

Gly Lys Ala Pro Lys Leu Leu Ile Tyr Asp Asn Asp Lys Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Arg Leu Ser Gly Val Val Phe Gly Gly Gly Thr
225                 230                 235                 240

Lys Val Thr Val

<210> SEQ ID NO 123
<211> LENGTH: 243
<212> TYPE: PRT
<213> ORGANISM: Artificial sequence
<220> FEATURE:
<223> OTHER INFORMATION: Single chain Fv

<400> SEQUENCE: 123

Val Arg Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly
            115                 120                 125

Ser Gly Gly Gly Gly Ser Asp Ile Val Leu Thr Gln Pro Pro Ser Ala
            130                 135                 140

Ser Gly Thr Pro Gly Gln Arg Val Thr Ile Ser Cys Thr Gly Asn Ser
145                 150                 155                 160

Ser Asn Ile Gly Ala Gly Tyr Asp Val His Trp Tyr Gln Gln Leu Pro
                165                 170                 175

Gly Lys Ala Pro Lys Leu Leu Ile Tyr Ser Asn Asn Gln Arg Pro Ser
                180                 185                 190

Gly Val Pro Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Asn Gly Pro Val Phe Gly Gly Gly Thr
225                 230                 235                 240

Gln Val Thr

<210> SEQ ID NO 124
<211> LENGTH: 244
<212> TYPE: PRT
<213> ORGANISM: Artificial sequence
<220> FEATURE:
<223> OTHER INFORMATION: Single chain Fv

<400> SEQUENCE: 124

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
                20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
            130                 135                 140

Ser Gly Thr Pro Gly Gln Arg Val Thr Ile Ser Cys Thr Gly Asn Ser
145                 150                 155                 160

Ser Asn Ile Gly Ala Gly Tyr Asp Val His Trp Tyr Gln Gln Leu Pro
                165                 170                 175

Gly Lys Ala Pro Lys Leu Leu Ile Tyr Ser Asn Asn Gln Arg Pro Ser
                180                 185                 190

Gly Val Pro Asp Arg Phe Ser Gly Ser Lys Ser Gly Thr Ser Ala Ser
```

```
            195                 200                 205
Leu Ala Ile Ser Gly Leu Arg Ser Glu Asp Glu Ala Asp Tyr Tyr Cys
    210                 215                 220

Ala Ala Trp Asp Asp Ser Leu Ser Ser Val Val Phe Gly Gly Gly Thr
225                 230                 235                 240

Lys Leu Thr Val

<210> SEQ ID NO 125
<211> LENGTH: 244
<212> TYPE: PRT
<213> ORGANISM: Artificial sequence
<220> FEATURE:
<223> OTHER INFORMATION: Single chain Fv

<400> SEQUENCE: 125

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
        35                  40                  45

Glu Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Lys Ala Pro Lys Leu Leu Ile Tyr Ala Asn Asn Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Asn Leu Asn Gly Leu Val Phe Gly Gly Gly Thr
225                 230                 235                 240

Gln Leu Thr Val

<210> SEQ ID NO 126
<211> LENGTH: 244
<212> TYPE: PRT
<213> ORGANISM: Artificial sequence
<220> FEATURE:
<223> OTHER INFORMATION: Single chain Fv

<400> SEQUENCE: 126

Val Gln Leu Leu Glu Ser Gly Gly Gly Leu Val Gln Pro Gly Gly Ser
1               5                   10                  15
```

-continued

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
 50                  55                  60

Gly Arg Phe Thr Ile Ser Arg Asp Asn Ser Lys Asn Thr Leu Tyr Leu
 65              70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Ala Asp Tyr Asp Val His Trp Tyr Gln Gln Leu Pro
                165                 170                 175

Gly Thr Ala Pro Lys Leu Leu Ile Tyr Ser Asn Asn Gln Arg Pro Ser
            180                 185                 190

Gly Val Ser Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Asn Gly Tyr Val Phe Gly Thr Gly Thr
225                 230                 235                 240

Lys Leu Thr Val

<210> SEQ ID NO 127
<211> LENGTH: 244
<212> TYPE: PRT
<213> ORGANISM: Artificial sequence
<220> FEATURE:
<223> OTHER INFORMATION: Single chain Fv

<400> SEQUENCE: 127

Val Gln Leu Leu Glu Ser Gly Gly Gly Leu Val Gln Pro Gly Gly Ser
 1               5                  10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
 50                  55                  60

Gly Arg Phe Thr Ile Ser Arg Asp Asn Ser Lys Asn Thr Leu Tyr Leu
 65              70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
    130                 135                 140

```
Ser Gly Thr Pro Gly Gln Arg Val Thr Ile Ser Cys Ser Gly Ser Ser
145                 150                 155                 160

Ser Asn Ile Gly Ala Gly Tyr Asp Val His Trp Tyr Gln Gln Leu Pro
            165                 170                 175

Gly Thr Ala Pro Lys Leu Leu Ile Tyr Gly Asn Thr Asn Arg Pro Ser
            180                 185                 190

Gly Val Ser Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Ala Ala Trp Asp Asp Ser Leu Asn Gly Leu Val Phe Gly Gly Gly Thr
225                 230                 235                 240

Gln Val Thr Val

<210> SEQ ID NO 128
<211> LENGTH: 244
<212> TYPE: PRT
<213> ORGANISM: Artificial sequence
<220> FEATURE:
<223> OTHER INFORMATION: Single chain Fv

<400> SEQUENCE: 128

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
            20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
            115                 120                 125

Ser Gly Gly Gly Gly Ser Asp Ile Val Leu Thr Gln Pro Pro Ser Ala
            130                 135                 140

Ser Gly Thr Pro Gly Gln Arg Val Thr Ile Ser Cys Ser Gly Ser Asn
145                 150                 155                 160

Ser Asn Ile Gly Ala Gly Tyr Asp Val Gln Trp Tyr Gln Gln Leu Pro
            165                 170                 175

Gly Thr Ala Pro Lys Leu Leu Ile Tyr Ala Asn Ser Asn Arg Pro Ser
            180                 185                 190

Gly Val Pro Asp Arg Phe Ser Gly Ser Lys Ser Gly Thr Ser Ala Ser
            195                 200                 205

Leu Ala Ile Ser Gly Leu Arg Ser Glu Asp Glu Ala Asp Tyr Tyr Cys
            210                 215                 220

Gly Val Trp Asp Asp Ser Leu Asn Gly Pro Val Phe Gly Gly Gly Thr
225                 230                 235                 240

Pro Val Thr Val

<210> SEQ ID NO 129
```

```
<211> LENGTH: 243
<212> TYPE: PRT
<213> ORGANISM: Artificial sequence
<220> FEATURE:
<223> OTHER INFORMATION: Single chain Fv

<400> SEQUENCE: 129

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
                20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
130                 135                 140

Ser Gly Thr Pro Gly Gln Arg Val Thr Ile Ser Cys Ser Gly Thr Ser
145                 150                 155                 160

Ser Asn Ile Gly Ser His Thr Val His Trp Tyr Gln Gln Leu Pro Gly
                165                 170                 175

Thr Ala Pro Lys Leu Leu Ile Tyr Glu Val Asn Lys Arg Pro Ser Gly
            180                 185                 190

Val Pro Asp Arg Phe Ser Gly Ser Lys Ser Gly Thr Ser Ala Ser Leu
        195                 200                 205

Ala Ile Ser Gly Leu Arg Ser Glu Asp Glu Ala Asp Tyr Tyr Cys Gln
    210                 215                 220

Ser Tyr Asp Ser Ser Leu Ser Ala Val Val Phe Gly Gly Gly Thr Gln
225                 230                 235                 240

Val Thr Val

<210> SEQ ID NO 130
<211> LENGTH: 243
<212> TYPE: PRT
<213> ORGANISM: Artificial sequence
<220> FEATURE:
<223> OTHER INFORMATION: Single chain Fv

<400> SEQUENCE: 130

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Gly Tyr Trp
                20                  25                  30

Met His Trp Val Arg Gln Ala Pro Gly Lys Gly Leu Glu Trp Val Ser
            35                  40                  45

Glu Ile Ser Gly Ser Gly Asp Ser Thr His Tyr Gly Asp Ser Val Lys
        50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Gly Ser
145                 150                 155                 160

Ser Asn Ile Gly Asn His His Val Ser Trp Tyr Gln Gln Leu Pro Gly
                165                 170                 175

Thr Ala Pro Lys Leu Leu Ile Tyr Gly Asn Thr Asn Arg Pro Ser Gly
            180                 185                 190

Val Ser Asp Arg Phe Ser Gly Ser Lys Ser Gly Thr Ser Ala Ser Leu
            195                 200                 205

Ala Ile Ser Gly Leu Arg Ser Glu Asp Glu Ala Asp Tyr Tyr Cys Gln
    210                 215                 220

Val Trp Asp Ser Ser Asp His Val Val Phe Gly Gly Gly Thr Lys
225                 230                 235                 240

Val Thr Val

<210> SEQ ID NO 131
<211> LENGTH: 243
<212> TYPE: PRT
<213> ORGANISM: Artificial sequence
<220> FEATURE:
<223> OTHER INFORMATION: Single chain Fv

<400> SEQUENCE: 131

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Arg Tyr Trp
            20                  25                  30

Met His Trp Val Arg Gln Ala Pro Gly Lys Gly Leu Glu Trp Val Ser
        35                  40                  45

Ala Ile Ser Gly Ser Gly Asp Ser Thr His Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Asn Gly Ser Leu Asp Tyr Trp Gly Gln Gly Thr Leu Val
            100                 105                 110

Thr Val Ser Ser Gly Ser Ala Gly Gly Gly Ser Gly Gly Gly Gly
        115                 120                 125

Ser Gly Gly Gly Gly Ser Asp Ile Val Leu Thr Gln Pro Pro Ser Ala
    130                 135                 140

Ser Gly Thr Pro Gly Gln Arg Val Thr Ile Ser Cys Thr Gly Gly Arg
145                 150                 155                 160

Phe Asn Ile Gly Asp Tyr Ala Val Asn Trp Tyr Gln Gln Leu Pro Gly
                165                 170                 175

Lys Ala Pro Lys Leu Leu Ile Tyr Asp Asn Asp Arg Arg Pro Ser Gly
            180                 185                 190

Val Ser Asp Arg Phe Ser Gly Ser Lys Ser Gly Thr Ser Ala Ser Leu
            195                 200                 205
```

```
Ala Ile Ser Gly Leu Arg Ser Glu Asp Glu Ala Asp Tyr Tyr Cys Gln
        210                 215                 220

Ser Phe Asp Ser Thr Leu Ser Gly Pro Val Phe Gly Gly Gly Thr Lys
225                 230                 235                 240

Val Thr Val

<210> SEQ ID NO 132
<211> LENGTH: 151
<212> TYPE: PRT
<213> ORGANISM: Artificial sequence
<220> FEATURE:
<223> OTHER INFORMATION: Single chain Fv

<400> SEQUENCE: 132

Ser Val Pro Ser Ser Leu Val Ile Glu Gly Arg Pro Glu Phe Ser Thr
1               5                   10                  15

Met Ala Glu Val Gln Leu Leu Glu Ser Gly Gly Gly Leu Val Gln Pro
            20                  25                  30

Gly Gly Ser Leu Arg Leu Ser Cys Ala Ala Ser Gly Phe Thr Phe Ser
        35                  40                  45

Gly Tyr Trp Met His Trp Val Arg Gln Ala Pro Gly Lys Gly Leu Glu
50                  55                  60

Trp Val Ser Glu Ile Ser Gly Ser Gly Asp Ser Thr His Tyr Gly Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gly Arg Asn Gly Ser Leu Asp Tyr Trp Gly Gln Gly
        115                 120                 125

Thr Leu Val Thr Val Ser Ser Gly Ser Ala Gly Gly Gly Ser Gly
    130                 135                 140

Gly Gly Gly Ser Gly Gly Gly
145                 150

<210> SEQ ID NO 133
<211> LENGTH: 10
<212> TYPE: PRT
<213> ORGANISM: Artificial sequence
<220> FEATURE:
<223> OTHER INFORMATION: TAT peptide

<400> SEQUENCE: 133

Arg Lys Lys Arg Arg Gln Arg Arg Arg Gly
1               5                   10

<210> SEQ ID NO 134
<211> LENGTH: 8
<212> TYPE: PRT
<213> ORGANISM: Artificial sequence
<220> FEATURE:
<223> OTHER INFORMATION: Nuclear localization signal

<400> SEQUENCE: 134

Asp Pro Lys Lys Lys Arg Lys Val
1               5

<210> SEQ ID NO 135
<211> LENGTH: 393
<212> TYPE: PRT
<213> ORGANISM: Homo sapiens
```

<400> SEQUENCE: 135

```
Met Glu Glu Pro Gln Ser Asp Pro Ser Val Glu Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 136

```
<211> LENGTH: 12
<212> TYPE: PRT
<213> ORGANISM: Artificial sequence
<220> FEATURE:
<223> OTHER INFORMATION: Cell internalization peptide

<400> SEQUENCE: 136

Glu Phe Gly Ala Cys Arg Gly Asp Cys Leu Gly Ala
1               5                   10
```

HUMAN SYNTHETIC SINGLE-CHAIN ANTIBODIES DIRECTED AGAINST THE COMMON EPITOPE OF MUTANT P53 AND THEIR USES

RELATED APPLICATIONS

This Application is a National Phase of PCT patent application Ser. No. PCT/IL2006/000372 having International Filing Date of Mar. 23, 2006, which claims the benefit of U.S. Provisional Patent Application Nos. 60/698,919 filed on Jul. 14, 2005 and 60/664,967 filed on Mar. 25, 2005. The contents of the above Applications are all incorporated herein by reference.

FIELD AND BACKGROUND OF THE INVENTION

The present invention relates to methods of treating cancer using antibodies directed against p53 mutant proteins.

The tumor suppressor gene p53 inhibits tumor growth primarily via induction of apoptosis. Mutations in the p53 tumor suppressor gene are the most common genetic alterations and occur in more than half of all human tumors. Approximately 90% of these alterations are missense mutations in the DNA-binding core domain responsible for sequence-specific binding of wild-type p53 protein to target genes. Many of these mutations cause a common conformational change in the p53 protein, which results in the exposure of an epitope that is otherwise hidden inside the wild type p53 molecule.

The involvement of p53 mutants in cancer progression was suggested to be associated either with trans-dominant suppression of wild-type p53 or a wild-type p53-independent oncogenic "gain of function". As wild-type p53 forms a tetramer to exert its tumor suppressor activity, it is generally accepted that heteromerization of mutant p53 with wild-type p53 drives the wild-type protein into a mutant or otherwise inactive conformation which leads to the trans-dominant suppression phenomenon. The "gain of function" of mutant p53 may be attributed to two mutually possible mechanisms. One is the abrogation of the tumor suppressor activity of p53 family members, p63 and p73, that were found to physically interact with mutant p53, but not with the wild-type p53 protein, and to interfere with their activity. The second involves the ability of mutant p53 to trans-activate or repress specific genes that mediate the various oncogenic activities of these mutants. Core domain p53 mutants were found to trans-activate genes, such as multiple drug resistance (MDR-1), c-myc, proliferating cell nuclear antigen (PCNA), interleukin-6 (IL-6) and epidermal growth factor receptor (EGFR) and early growth receptor (EGR-1), these genes being different from those reactivated by wild type p53.

Given the active role of p53 mutants in promoting tumorigenicity, efforts have been made to inactivate their function or to revert them into a wild-type phenotype. These include the introduction of second site suppressor mutations (e.g., N239Y, N268D and H168R) that can at least partially restore specific DNA binding to mutant p53. In addition, synthetic peptides derived from the C-terminus of the p53 protein, or the CDB3, a p53-binding protein (p53BP2) derived compound, were found to restore DNA binding followed by transcriptional trans-activation, as well as induction of p53 dependent apoptosis to tumor cells. Moreover, low molecular weight compounds, such as CP-31398 and PRIMA-1, were shown to restore wild type conformation, transcriptional trans-activation and to induce apoptosis in cells and in human tumor xenografts carrying mutant p53. However, such peptides and compounds lack the ability to distinguish between the wild-type and mutant form of p53, a property crucial for targeted treatment.

Thus, novel anti cancer treatment modalities which specifically target a broad range of p53 mutants and not wild-type p53 proteins are desired More than 90% of the mutations found in the p53 protein produce a conformational change in the p53 protein which results in the exposure of an epitope, which is otherwise hidden in the hydrophobic core of the molecule. Such an epitope was localized to amino acids 212-217 of the human p53 protein (GenBank Accession No. NP_000537) or amino acids 209-214 of the mouse p53 protein (GenBank Accession No. NP_035770) and has a sequence of FRHSVV (SEQ ID NO:1). Prior studies describe the isolation of a single-chain scFv mouse antibody prepared from a mouse immunized with SEQ ID NO:1. This antibody (named ME1), was found to be expressed in the cytosol of mammalian cells and to bind mutant p53 protein but not the wild-type p53 protein with an affinity of $10^{-7}$ M (Govorko D, Cohen G and Solomon B., 2001, J. Immunol. Methods. 258: 169-81). However, although this antibody presents a useful tool for clarifying the role of mutant p53 in tumor transformation, due to its mouse origin and its moderate affinity towards the mutated p53, its therapeutic application is limited.

There is thus a widely recognized need for, and it would be highly advantageous to have, a human derived antibody capable of specifically targeting with high affinity mutant p53 proteins.

SUMMARY OF THE INVENTION

According to one aspect of the present invention there is provided an isolated polynucleotide comprising a nucleic acid sequence encoding a polypeptide capable of specifically binding an exposed epitope shared by p53 mutant proteins and not by wild type p53 protein, wherein an affinity of said specific binding is less than 25 nanomolar.

According to another aspect of the present invention there is provided an isolated polynucleotide comprising a nucleic acid sequence encoding a CDR-containing polypeptide comprising at least one CDR selected from the group consisting of CDR SEQ ID NOs:8-112.

According to still another aspect of the present invention there is provided an isolated polypeptide comprising an amino acid sequence capable of specifically binding an exposed epitope shared by p53 mutant proteins and not by wild type p53 protein, wherein an affinity of the specific binding is less than 25 nanomolar.

According to an additional aspect of the present invention there is provided an isolated polypeptide comprising an amino acid sequence of at least one CDR selected from the group consisting of CDR SEQ ID NOs:8-112.

According to yet another aspect of the present invention there is provided a pharmaceutical composition comprising as an active ingredient the isolated polynucleotide and a pharmaceutically acceptable carrier.

According to still an additional aspect of the present invention there is provided a nucleic acid construct comprising the isolated polynucleotide and a promoter for directing an expression of said isolated polynucleotide in cells.

According to a further aspect of the present invention there is provided a method of inducing apoptosis and/or growth arrest of cancer cells, comprising contacting with or expressing in the cancer cells the isolated polypeptide, thereby inducing apoptosis and/or growth arrest of the cancer cells.

According to yet a further aspect of the present invention there is provided a method of treating a subject suffering from or being predisposed to a p53-related cancer, comprising administering to or expressing in cells of the subject a therapeutically effective amount of the isolated polypeptide, thereby treating the p53-related cancer in the subject.

According to still a further aspect of the present invention there is provided a method of diagnosing a p53-related cancer in a subject comprising: (a) contacting a biological sample of the subject with the isolated polypeptide under conditions suitable for immunocomplex formation which comprises the isolated polypeptide and p53 mutant proteins; and (b) detecting formation of the immunocomplex, thereby diagnosing the cancer in the subject.

According to still a further aspect of the present invention there is provided a use of the isolated polypeptide for the manufacture of a medicament identified for the treatment of a p53-related cancer.

According to still a further aspect of the present invention there is provided a use of the isolated polynucleotide for the manufacture of a medicament identified for the treatment of a p53-related cancer.

According to still a further aspect of the present invention there is provided a use of the nucleic acid construct for the manufacture of a medicament identified for the treatment of a p53-related cancer.

According to still a further aspect of the present invention there is provided a composition comprising a viral display vehicle expressing on a surface thereof a polypeptide capable of specifically binding an exposed epitope shared by p53 mutant proteins and not by wild type p53 protein, wherein an affinity of the specific binding is less than 25 nanomolar.

According to still a further aspect of the present invention there is provided a composition comprising a viral display vehicle expressing on a surface thereof a CDR-containing polypeptide comprising at least one CDR selected from the group consisting of CDR SEQ ID NOs:8-112.

According to still a further aspect of the present invention there is provided a pharmaceutical composition comprising as an active ingredient the viral display vehicle, and a pharmaceutically acceptable carrier.

According to still a further aspect of the present invention there is provided a method of inducing apoptosis and/or growth arrest of cancer cells, comprising contacting with the cancer cells the viral display vehicle, thereby inducing apoptosis and/or growth arrest of the cancer cells.

According to still a further aspect of the present invention there is provided a method of treating a subject suffering from or being predisposed to a p53-related cancer, comprising administering to the subject a therapeutically effective amount of the viral display vehicle, thereby treating the p53-related cancer in the subject.

According to still a further aspect of the present invention there is provided a use of the viral display vehicle for the manufacture of a medicament identified for the treatment of a p53-related cancer.

According to further features in preferred embodiments of the invention described below, the pharmaceutical composition, the epitope is as set forth by SEQ ID NO:1.

According to still further features in the described preferred embodiments the polypeptide comprises at least one CDR selected from the group consisting of SEQ ID NOs:39-41, 45-47 and 60-62.

According to still further features in the described preferred embodiments the polypeptide is selected from the group consisting of a Fab fragment, an Fv fragment, a single chain antibody, a single domain antibody and an antibody.

According to still further features in the described preferred embodiments the single chain antibody is selected from the group consisting of SEQ ID NO:113, SEQ ID NO:114 and SEQ ID NO:115.

According to still further features in the described preferred embodiments the nucleic acid construct further comprising an additional nucleic acid sequence encoding a nuclear localization signal (NLS) fused to the isolated polypeptide.

According to still further features in the described preferred embodiments the NLS is set forth by SEQ ID NO:134.

According to still further features in the described preferred embodiments the polynucleotide further comprises an additional nucleic acid sequence encoding a drug. According to still further features in the described preferred embodiments the polypeptide further comprises an amino acid sequence of a drug.

According to still further features in the described preferred embodiments the polypeptide is attached to a drug.

According to still further features in the described preferred embodiments the drug is a toxin and/or a chemotherapy drug.

According to still further features in the described preferred embodiments the polynucleotide further comprises an additional nucleic acid sequence encoding a detectable label.

According to still further features in the described preferred embodiments the polypeptide further comprises a detectable label.

According to still further features in the described preferred embodiments the detectable label is biotin and digoxigenin.

According to still further features in the described preferred embodiments the biological sample is selected from the group consisting of blood, lymph node biopsy, bone marrow aspirate and a tissue sample.

According to still further features in the described preferred embodiments each of the Fab fragment, the Fv fragment, the single chain antibody, the single domain antibody and the antibody is humanized.

The present invention successfully addresses the shortcomings of the presently known configurations by providing antibodies and methods of inhibiting cell growth and inducing apoptosis by using antibodies directed against mutant p53 proteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b depict amino acid sequence alignments of the twenty human scFv clones selected for binding the common epitope of mutant p53 (FRHSVV; SEQ ID NO:1). The scFvs are set forth by SEQ ID NOs:113-132. FIG. 1a depicts amino acids of the variable Heavy chain ($V_H$) (1-119) and FIG. 1b depicts amino acids of the variable light chain ($V_L$) (135-245); twenty human scFvs against the mutant p53 common epitope. Red=identical amino acids, blue=amino acids which have low consensus values (more than 50% identical) and black=amino acids which are less than 50% identical. CDRs are indicated by a black bar.

Figure 2A:
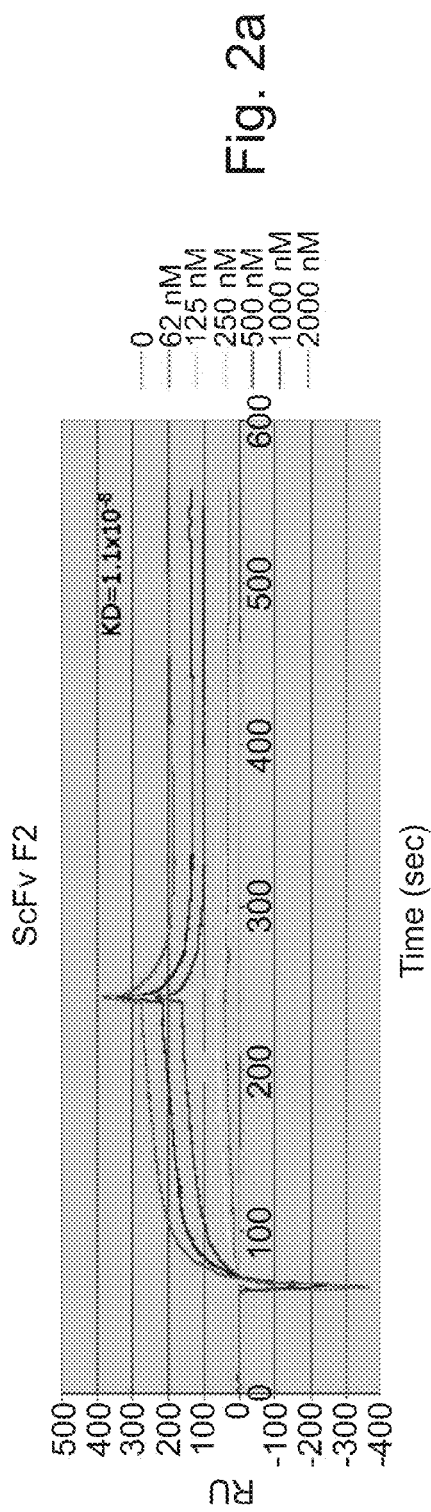
Figure 2B:
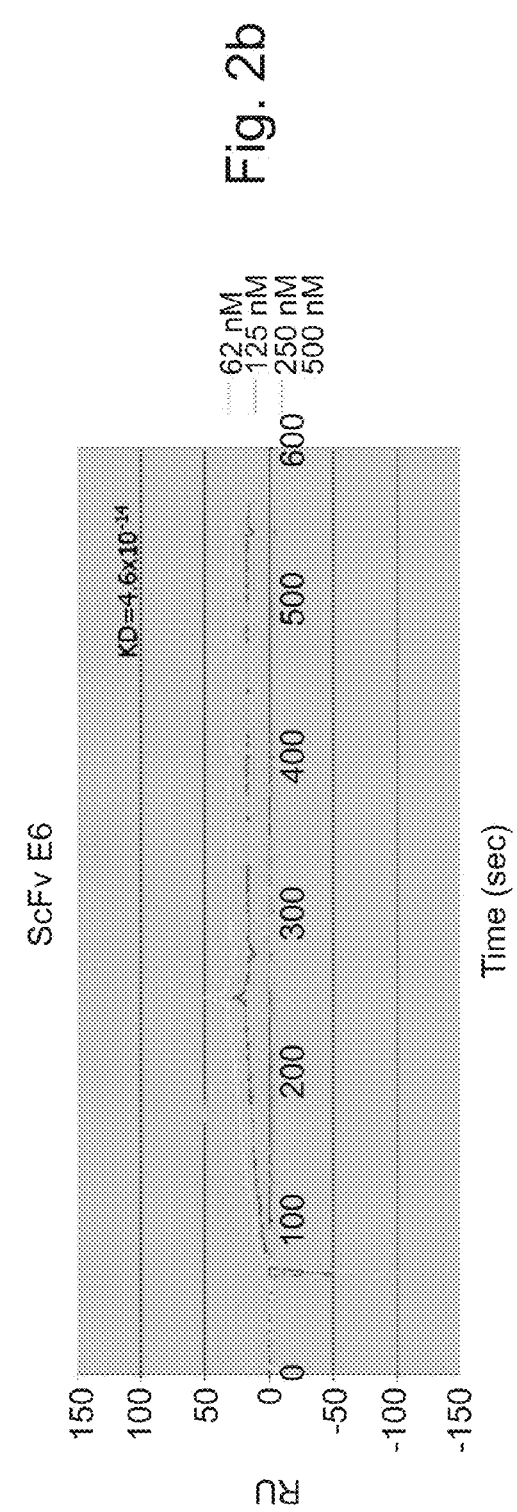

FIGS. 2a-b depict the binding of F2 scFv (also referred to herein as "TAR1") (FIG. 2a) and E6 scFv (FIG. 2b) clones to the FRHSVV (SEQ ID NO:1) epitope. Binding was determined using the BIACore at the indicated concentrations of antibodies. The sequences of the VH and VL chains of the F2 and E6 scFv clones are shown in FIGS. 1a-b. RU=resonance units. The binding constant was determined using the software that is supplied with the BIAcore instrument.

Figure 3:
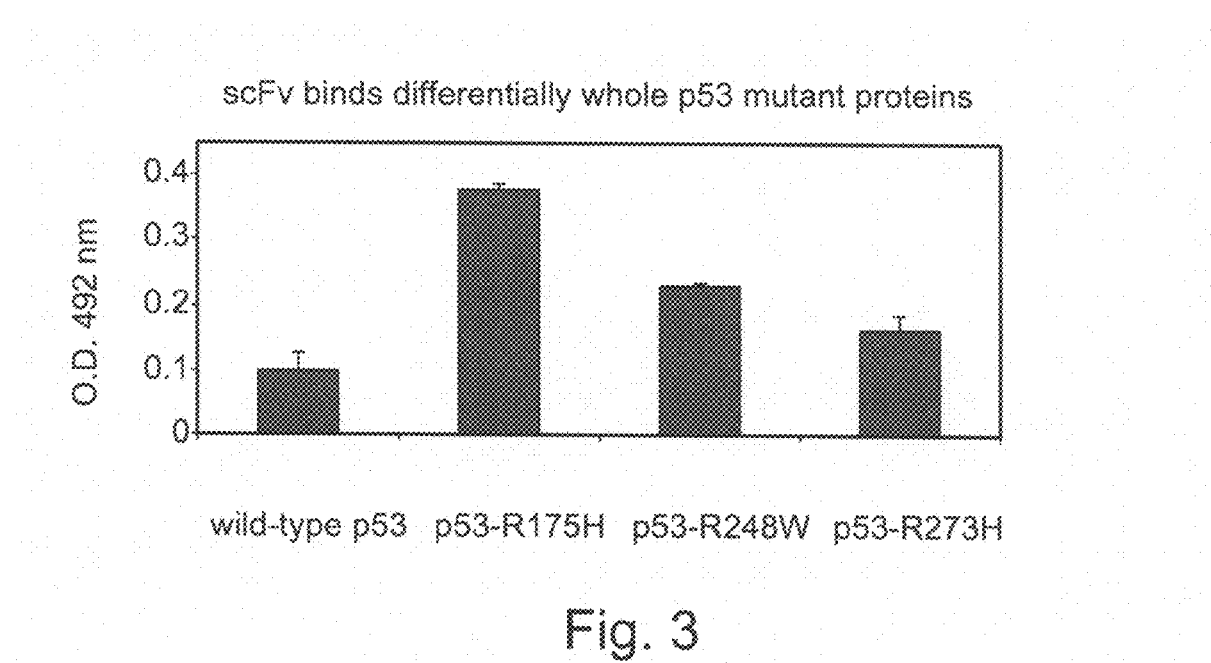

FIG. 3 is a bar graph depicting the binding of scFv F2 to whole p53 molecules as determined using an ELISA. ELISA plates were coated with wild-type p53 or mutant p53-R175H, p53-R248H and p53-R273W whole p53 proteins which were prepared from recombinant baculovirus infected sf9 insect cells (Hupp T. R and Lane D. P., Curr. Biol. 1994, 4. 865-875), and 250 ng scFv F2 was added. Note the specific binding of the scFv F2 to the R175H-mutant p53 molecule as compared with the low binding to the wild type p53.

Figure 4F:
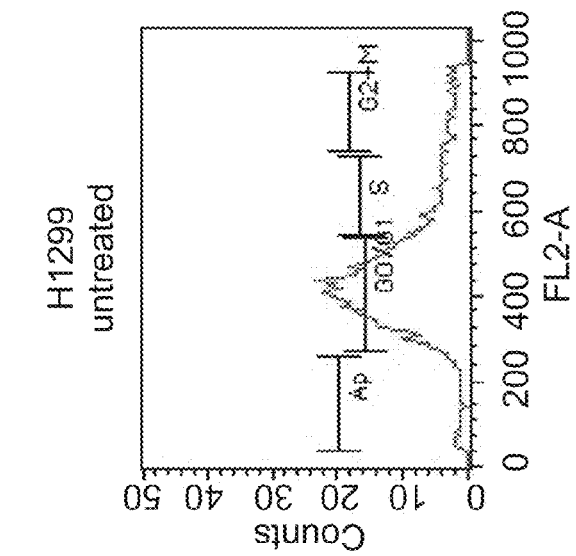
Figure 4E:
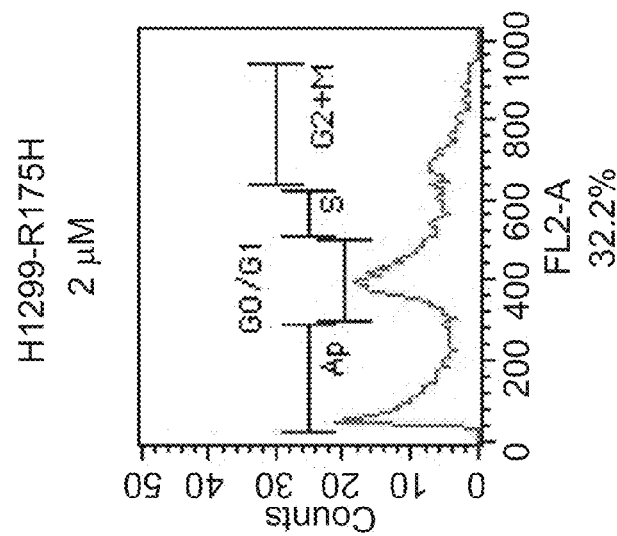
Figure 4D:
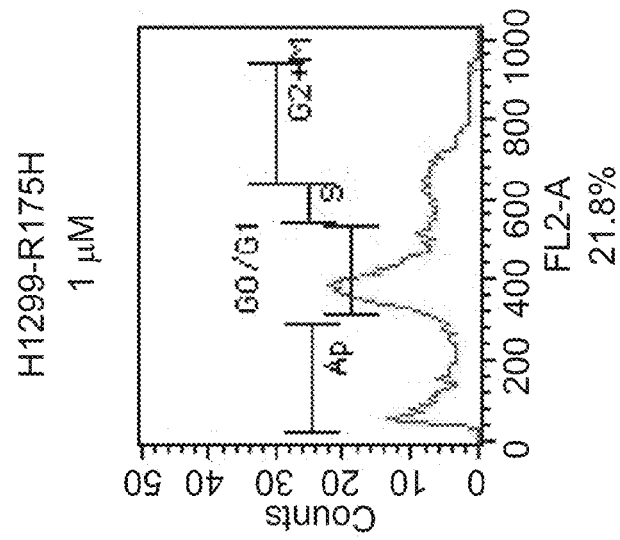
Figure 4J:
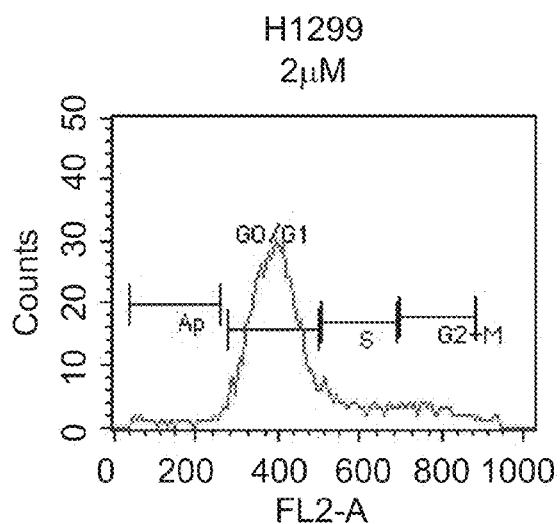

FIGS. 4a-j are FACS analyses depicting the effect of the scFv F2 on apoptosis in p53 null human lung carcinoma cells (H1299 p53−/−; FIGS. 4f-j) or in human lung carcinoma cells carrying the hot spot mutation R175H (H1299-R175H; FIGS. 4a-e). Cells were incubated for 24 hours with scFv-F2 at the following concentrations: 0 nM (untreated cells, FIGS. 4a and f), 250 nM (FIGS. 4b and g), 500 nM (FIGS. 4c and h), 1 µM (FIGS. 4d and i) and 2 µM (FIGS. 4e and j). Following 24 hours, the cells were fixed with ethanol, stained with Propidium Iodide and the cell cycle profile was determined. Numbers indicate the % of apoptotic cells in each preparation [0.8% % (FIG. 4a), 1.9% (FIG. 4c), 21.8% (FIG. 4d), 32.2% (FIG. 4e), 0-0.8% (FIGS. 4f-j)]. Note the significant increase in apoptosis in the presence of the scFv-F2 antibody in cells expressing the R175H p53 mutation.

Figure 5:
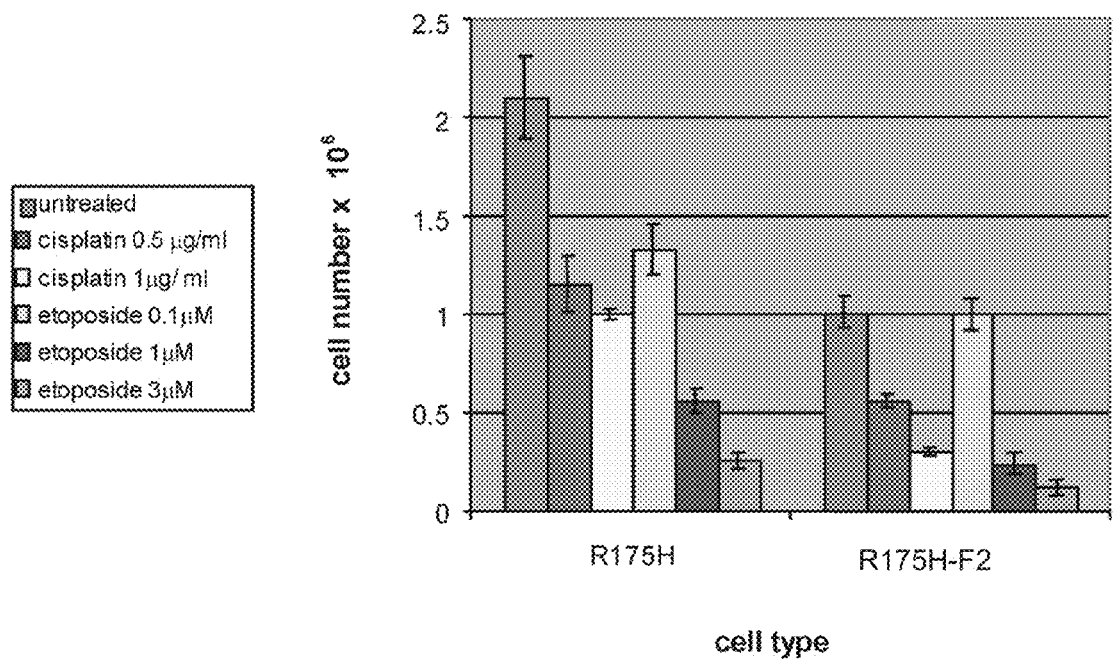

FIG. 5 is a bar graph depicting increased susceptibility to drug treatment of cells expressing the scFv F2 antibody. Human lung carcinoma cells carrying the R175H mutation (H1299-R175H) were stably transfected to express the scFv F2 antibody (H1299-R175H-scFv-F2) and the effect of the etoposide and cisplatin drugs on cell survival (by cell counts) was determined 48 hours following drug treatment. Note the increased susceptibility of the lung carcinoma cells to low concentrations of cisplatin (0.5 µg/ml) or etoposide (1 µM) in cells expressing the scFvF2 antibody.

Figures 6A, 6B:
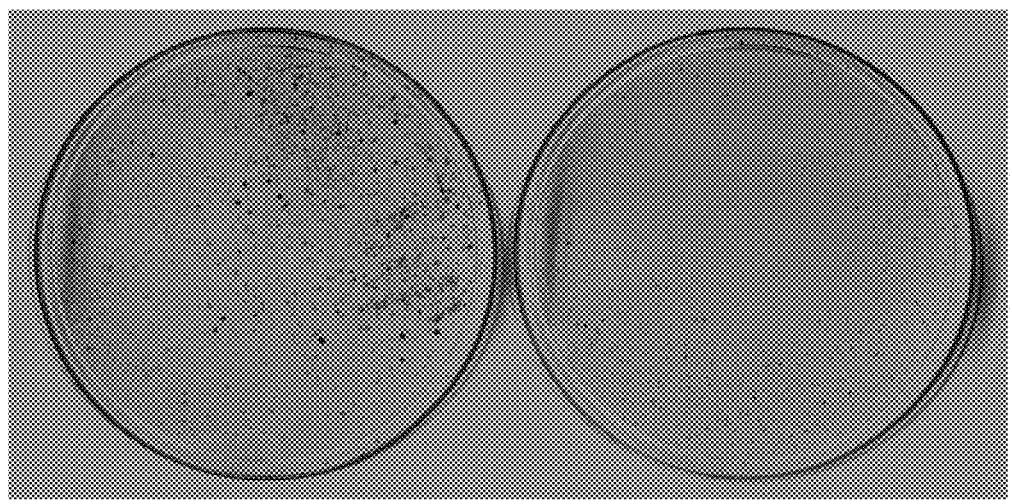
Figure 6C:
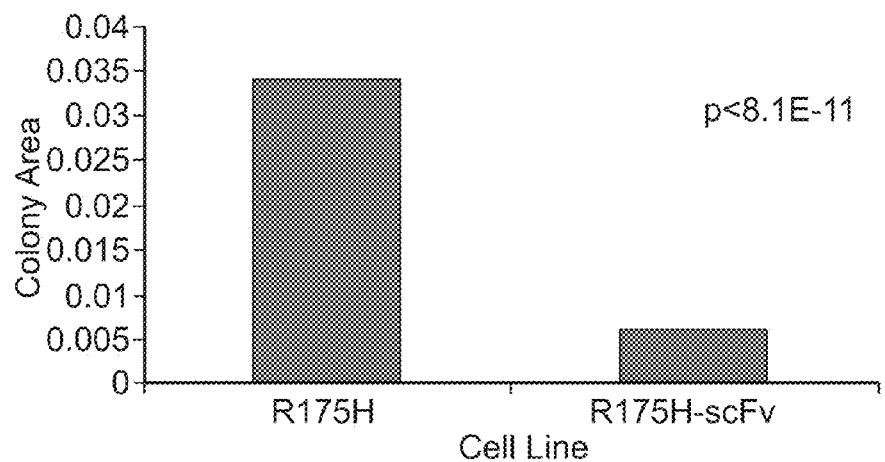
Figure 6D:
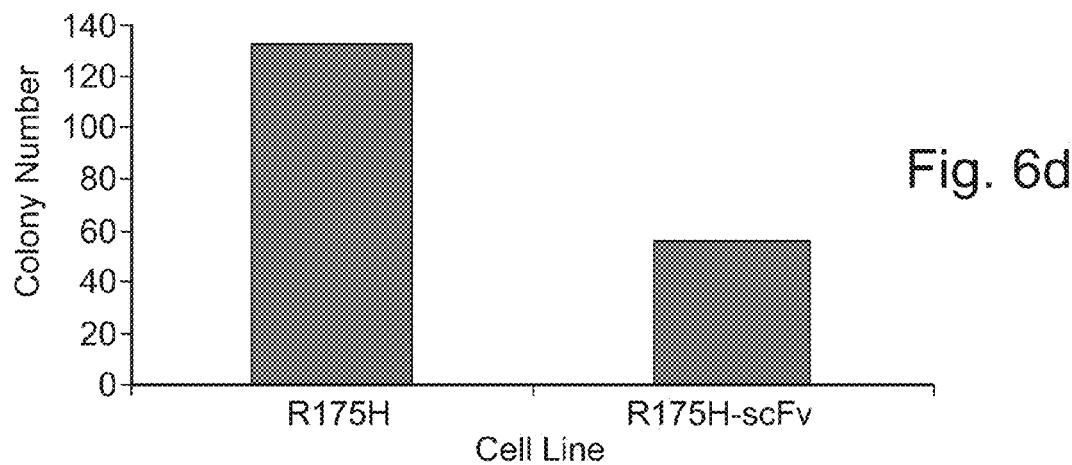

FIGS. 6a-d depict inhibition of colony formation in lung carcinoma cells expressing the scFv F2 antibody. H1299-R175H cells were stably transfected to express the scFv F2 antibody (H1299-R175H-scFv-F2) and the effect of the intracellular expression of scFv F2 on colony formation was determined. 500-1000 cell/plate of H1299-R175H cells or H1299-R175H-scFv-F2 cells were seeded on plates containing RPMI culture medium and allowed to grow for two weeks. FIGS. 6a-b are photographs of the Giemsa-stained colonies present following two weeks in culture. FIG. 6a—H1299-R175H cells; FIG. 6b—H1299-R175H-scFv-F2 cells. FIGS. 6c-d are bar graphs depicting the colony number (FIG. 6c) and the colony area (FIG. 6d) of the H1299-R175H or H1299-R175H-scFv-F2 cells following two weeks in culture. Note the significant decrease in both the colony number (FIG. 6c) and colony area (FIG. 6d) in cells expressing the scFv F2 antibody.

FIG. 7 is a graph depicting the anti tumor effect of scFv F2 on human tumor cell xenografts in mice. Nude mice were subcutaneously injected with $5 \times 10^6$ of the lung carcinoma H1299-R175H cells. Following three days, the mice received an intra-tumor injection of 200 µg scFv F2 or PBS (50 µl) as control, which was repeated every other day during two weeks. The tumor size was measured following 6, 15, 21, 25, 28, 32, and 36 days post inoculation with H1299-R175H cells and the tumor volume was calculated. The results are presented as relative volume $V_t/V_o$ where $V_t$ is the volume at the indicated day and $V_o$ is the volume at the first scFv F2 injection.

Figures 8E, 8F:
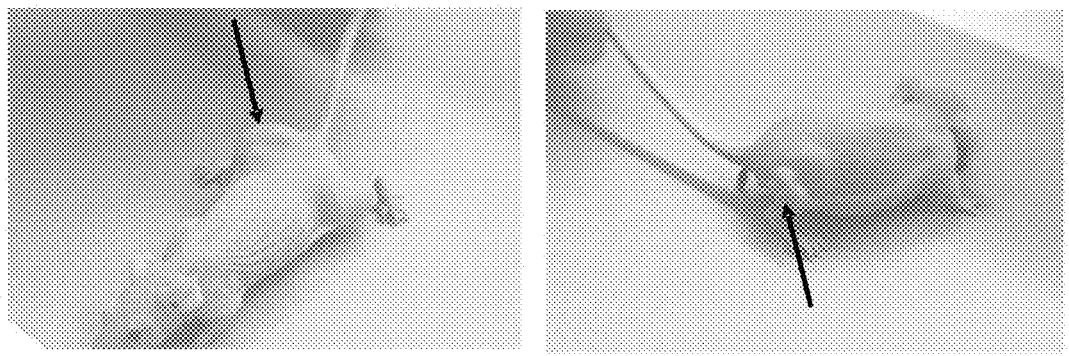

FIGS. 8a-f depict the effect of the scFv F2 antibody on tumor growth in vivo. Mice were subcutaneously injected with human xenografts of H1299-R175H cells followed by intra-tumor injections as described for FIG. 7. Shown are representative photographs of the PBS—injected mice (FIGS. 8d-f) as compared with the scFv F2—injected mice (FIGS. 8a-c). The arrows point to the place of xenograft and tumor formation. Note the presence of large tumors in the PBS-treated mice (FIGS. 8a-c) and the absence of such tumors in the scFv F2 treated mice (FIGS. 8d-f).

Figure 9:
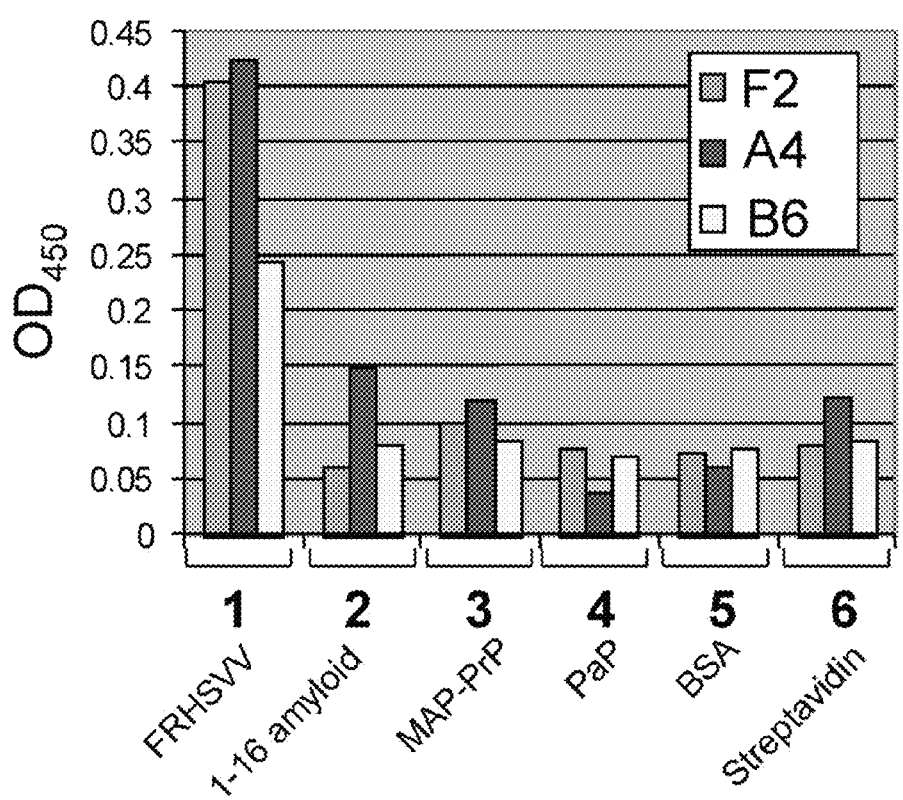

FIG. 9 is a bar graph depicting the binding specificity of scFvs. ELISA was performed using the F2, A4 and B6 scFvs from the isolated scFv collection depicted in FIGS. 1a-b. The binding antigens were Bovine Serum Albumin (BSA; lane 5), Streptavidin (lane 6) and the following peptides: FRHSVV (SEQ ID NO:1; the common epitope of mutant p53; lane 1), amino acids 1-16 of the β amyloid peptide DAEFRHDSGYEVHHQK (SEQ ID NO:2; lane 2), amino acids 144-153 of the multiple antigen peptide presenting the human prion protein (MAP-PrP DYEDRYYRE; SEQ ID NO:3; lane 3) and a peptide corresponding to a prostate cancer antigen (PaP ILLWQPIPV; SEQ ID NO:4; lane 4). Note the high binding specificity of the F2 and A4 antibodies towards the peptide representing the common epitope of mutant p53 (SEQ ID NO:1).

Figure 10A:
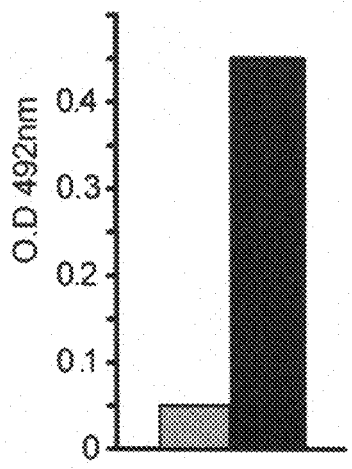
Figure 10C:
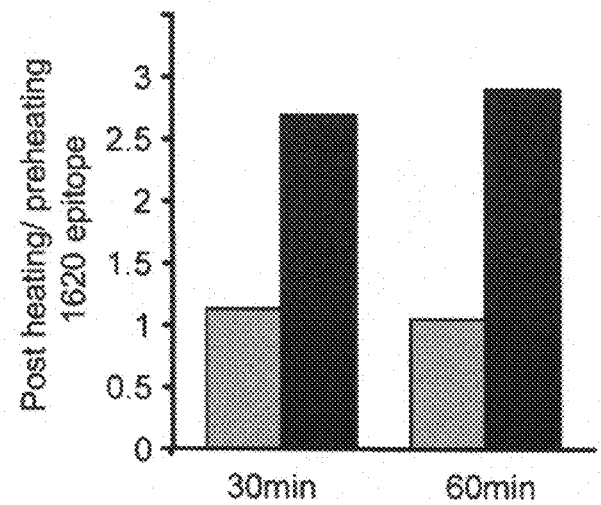
Figure 10B:
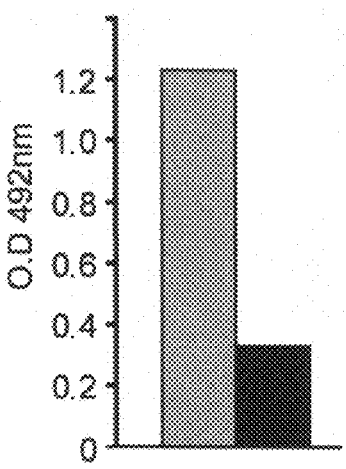
Figure 10D:
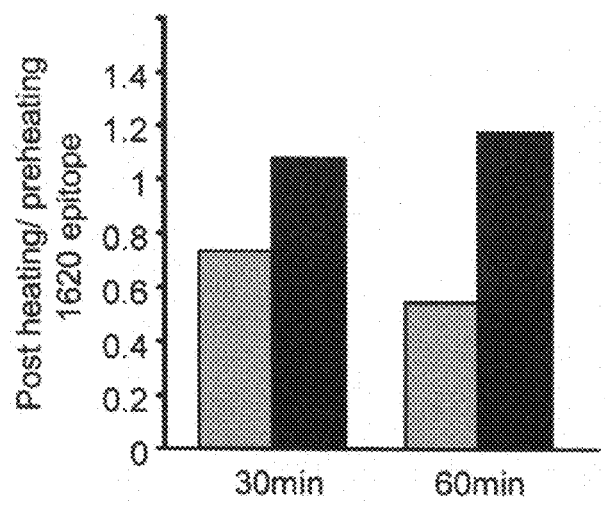

FIGS. 10a-d are bar graphs depicting ELISA assays performed on recombinant p53 wild type or mutant core domains using the TAR1 antibody (FIG. 10a) or the mAB 1620 specific for wild-type p53 (FIGS. 10b-d). FIG. 10a—Binding of TAR1 to mutant p53 R175H core domain (black) and wild-type p53 core domain (gray). Note the high specificity of the TAR1 antibody to the p53 mutant R175H core domain (~0.5 O.D.) as compared to the p53 wild type core domain (~0.05 O.D.). FIG. 10b—Binding of mAb 1620 to mutant p53 R175H core domain (black) and wild-type p53 core domain (gray). Note the high specificity of the mAb 1620 to the p53 wild type core domain (~1.2 O.D.) as compared to the mutant p53 R175H core domain (~0.3 O.D.). FIGS. 10c and d—The p53 mutant (R175H) (FIG. 10c) or wild type (FIG. 10d) core domains were heated for 30 or 60 minutes at 37° C. in the absence (grey columns) or presence (black columns) of 0.4 µM TAR1 and the binding of the mAb 1620 was tested Note that following heating and in the presence of TAR1, the binding of the mutant p53 to the wild type specific antibody (mAb 1620) is 3 times higher than in the absence of TAR1 (FIG. 10c). Also note that binding of mAb 1620 to wild type p53 core domain was higher in the presence of TAR1 (FIG. 10d). These results demonstrate that TAR1 induces a conformational change in mutant p53 and stabilizes wild-type p53 conformation.

Figure 11A:
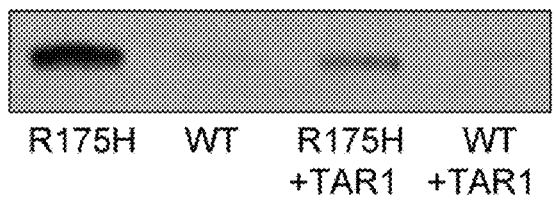
Figure 11B:
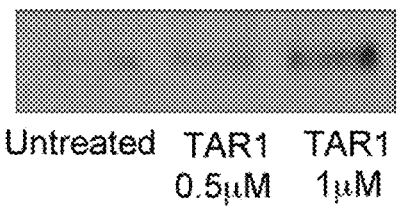

FIGS. 11a-b are immunoprecipitation assays depicting the binding of the mAb DO-12 mAb, a p53-mutant specific antibody, to wild type or R175H mutant p53. FIG. 11a—The p53 mutant (R175H; lanes 1 and 3) or wild-type (WT; lanes 2 and 4) core domains were subjected to immunoprecipitation using the DO-12 mAb prior to (lanes 1 and 2) or following (lanes 3 and 4) incubation for overnight with 80 nM TAR1. Note the high binding specificity of the mAb DO-12 to the R175H core domain (lane 1) as compared to the low binding specificity to the wild type p53 core domain (lane 2). Also note that following overnight incubation with 80 nM TAR1, the binding of the mAb DO-12 to the mutant R175H p53 core domain is significantly decreased (lane 3), while the binding of the mAb DO-12 to the wild type p53 core domain is not affected (lane 4). FIG. 11b—H1299 cells expressing mutant p53 R175H were treated over night with 1 μM TAR1 and extracts were immunoprecipitated with the mAb 1620 (a p53 wild type-specific antibody). Note the significant increase, in a TAR1 dose-dependent manner, in the binding of mAb 1620 to protein extracts of cells expressing the mutant p53, demonstrating that TAR1 is capable of restoring the wild type p53 conformation in a p53 R175H mutant in vivo.

Figure 12:
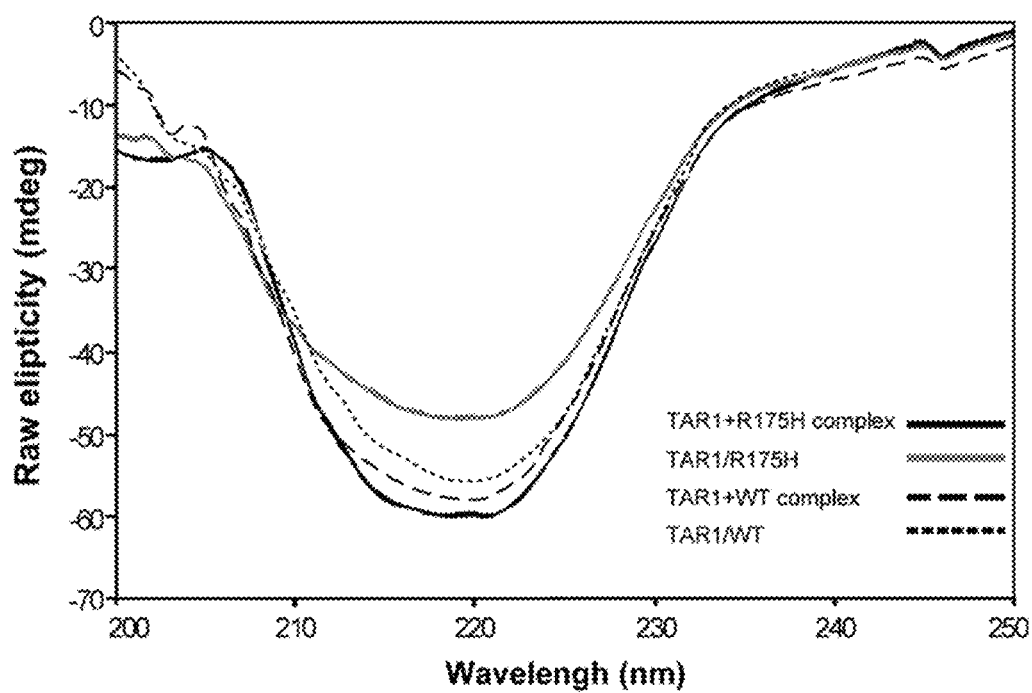

FIG. 12 is a Circular dichroism analysis depicting the spectra of wild type or R175H mutant p53 core domains in the presence of TAR1 antibody. Circular dichroism measurements were taken simultaneously for either wild-type p53 or mutant p53 R175H core domains and TAR1 separately (TAR1/WT; TAR1/R175H) or as an immunocomplex (TAR1+WT complex; TAR1+R175H complex). Note that binding of TAR1 caused a shift in the spectrum of mutant p53 while almost no difference was observed in the spectrum of the wild-type core domain indicating a conformational change in the complex of TAR1 and mutant p53. Also note that the spectra of both TAR1 complexes, with wild-type p53 and with mutant p53, are very similar indicating conformational similarity.

FIGS. 13a-h are Western blot analyses of H1299 cells expressing R175H mutant p53 extracts probed with anti p21 (FIG. 13a), MDM2 (FIG. 13b), Egr1 (FIG. 13c), Bax (FIG. 13d) and tubulin (FIGS. 13e-h) antibodies demonstrating the effect of TAR1 treatment on the transcriptional transactivation of mutant p53 (R175H). H1299 cells stably expressing mutant p53 were treated for 24 hours with TAR1 at a final concentration of 0.5 μM (lane 2) or 1 μM (lane 3), or were remained untreated (lane 1), following which protein samples were prepared and subjected to Western blot analyses using the following antibodies: anti p21 (Santa Cruz Biotechnology, Inc., dilution 1:1000, MDM2 (was a gift from M. Oren, hybridoma supernatant diluted 1:40), Egr1 (Santa Cruz Biotechnology, Inc., dilution 1:500), Bax (Abcam Laboratories, Ltd, UK, dilution 1:1000), tubulin (Sigma, dilution 1:2500). The expression level of tubulin served as loading control. Note the concentration-dependent increase in the expression level of p21, MDM2 and Bax following TAR1 treatment, demonstrating that TAR1 is capable of restoring the transcriptional transactivation function to mutant p53. In contrast, note that TAR1 treatment resulted in a decrease in the expression level of Egr1, demonstrating that TAR1 abrogates the gain of function activity of the p53 mutant protein.

Figures 13A, 13B, 13C, 13D:
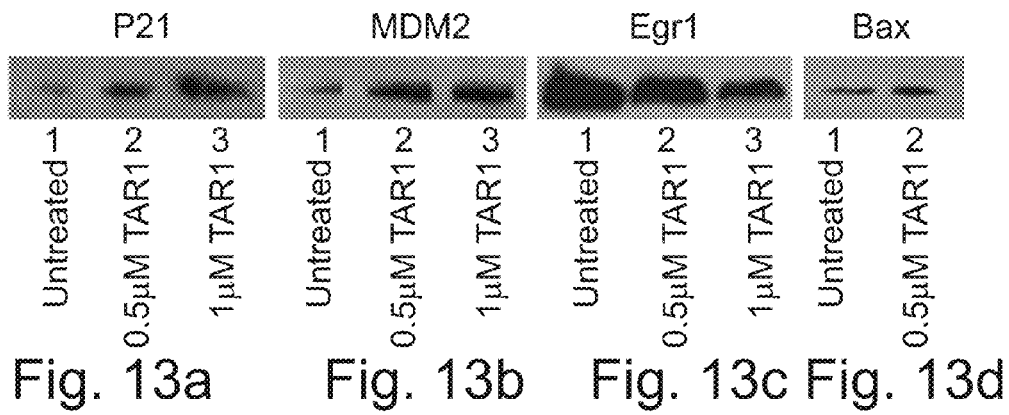
Figures 13E, 13F, 13G, 13H:
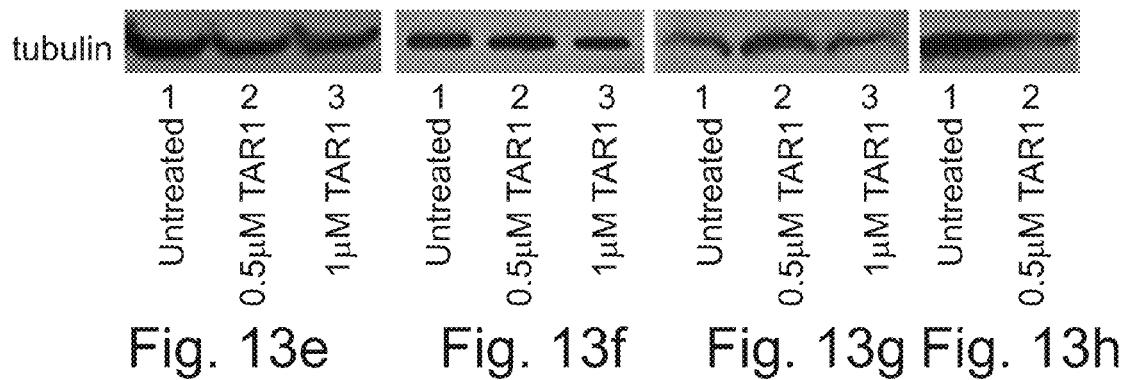
Figure 14:
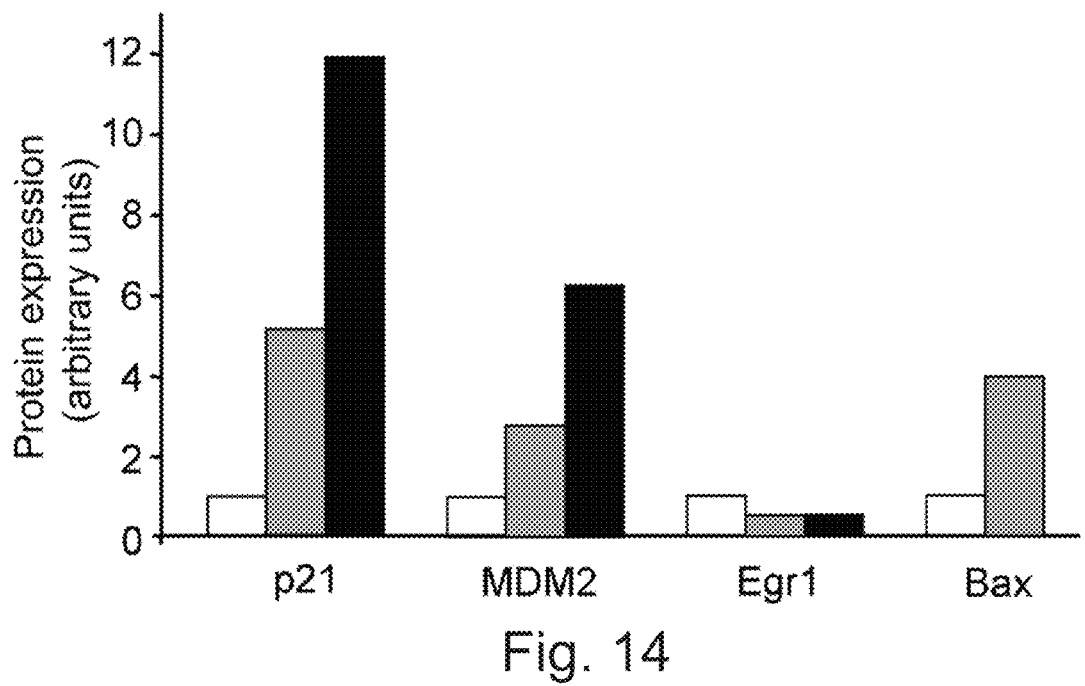

FIG. 14 is a bar graph depicting the quantification of the Western blot analyses shown in FIGS. 13a-h. The expression level of each protein in the treated or untreated cells was normalized by the expression level of tubulin. White bars—untreated cells; grey bars—cells treated for 24 hours with 0.5 μM TAR1; black bars—cells treated for 24 hours with 1 μM TAR1.

FIGS. 15a-h are fluorescence activated cell sorting (FACS) analyses depicting the effect of TAR1 (scFv-F2) on apoptosis in p53 null H1299 human lung carcinoma cells (FIGS. 15c-d), H1299-R175H cells expressing mutant p53 (FIGS. 15a-b) or HCT116 colon cancer cells expressing wild type p53 (FIGS. 15g-h) or mutant R175H p53 (FIGS. 15e-f) Cells were incubated for 24 hours with 1 μM TAR1 (FIGS. 15b, d, f and h) or were remained untreated (FIGS. 15a, c, e and g), following which the cells were fixed with ethanol, stained with Propidium Iodide and their cell cycle profile was determined. Note the significant increase in apoptosis (Ap fraction) in the presence of the TAR1 antibody in cells expressing the R175H p53 mutation (FIGS. 15b and f) as compared to cancer cells with null p53 or cells expressing the wild-type p53 protein (FIGS. 15d and h).

FIGS. 16a-d are TdT-mediated dUTP nick-end labeling (TUNEL) of H1299 cells null for p53 (FIGS. 16c-d) or H1299 cells expressing mutant p53 R175H (FIGS. 16a-b) in the absence (FIGS. 16a and c) or presence (FIGS. 16b and d) of 1 μM TAR1. H1299 cells stably transfected to express mutant p53 (R175H; FIGS. 16a-b) or untransfected (FIGS. 16c-d) were treated for 24 hours with TAR1 (at a final concentration of 1 μM) (FIGS. 16b and d) or remained untreated (FIGS. 16a and c) and the effect of treatment was determined using the TUNEL assay (R&D Systems, Inc).

Figures 17A, 17B:
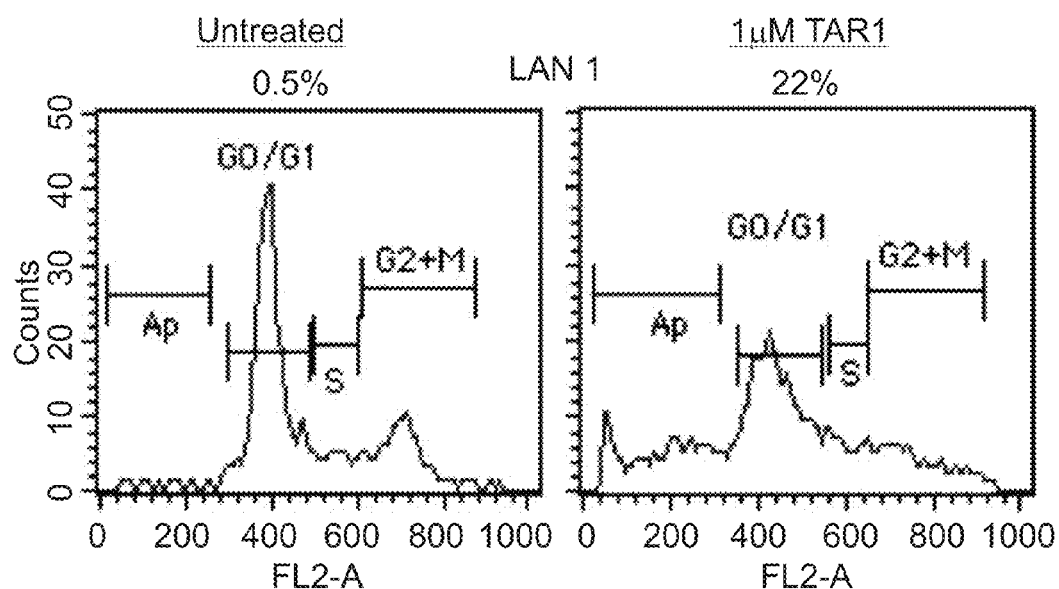
Figures 17C, 17D:
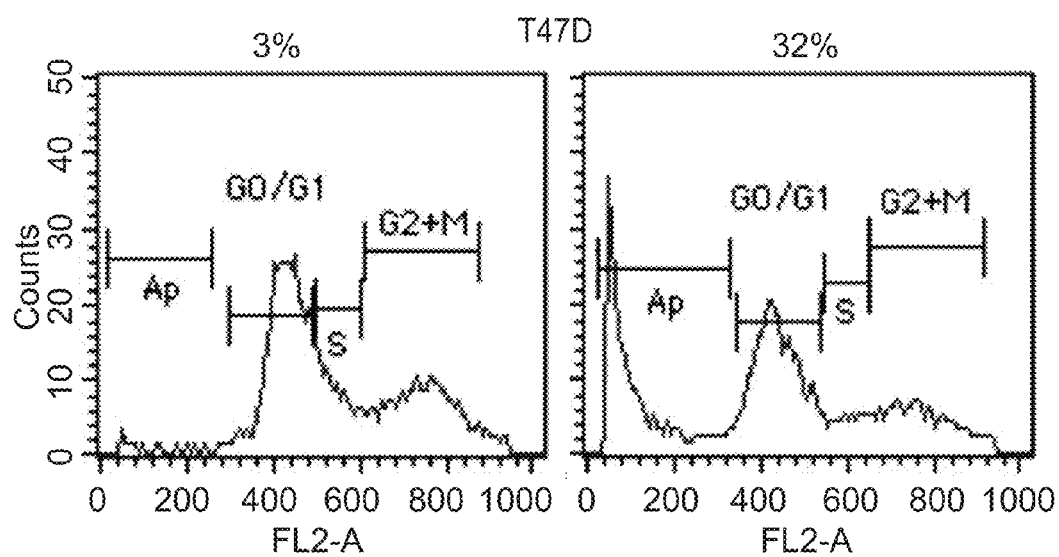
Figures 17E, 17F:
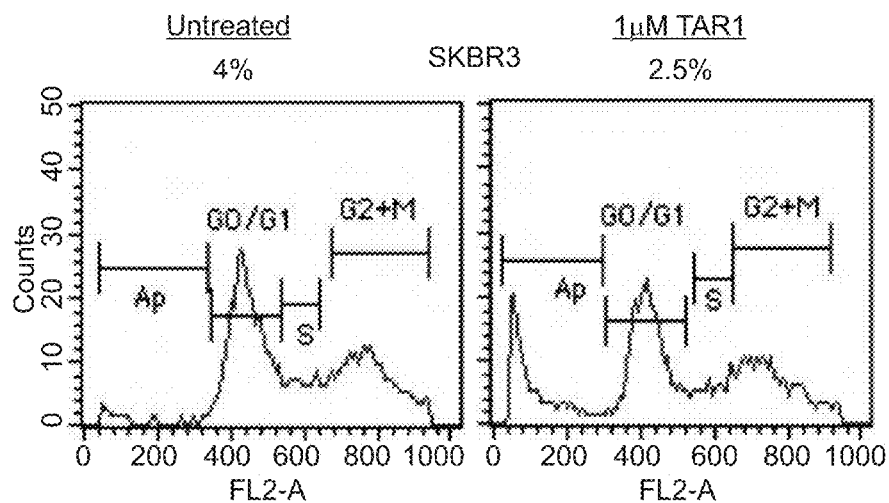
Figures 17G, 17H:
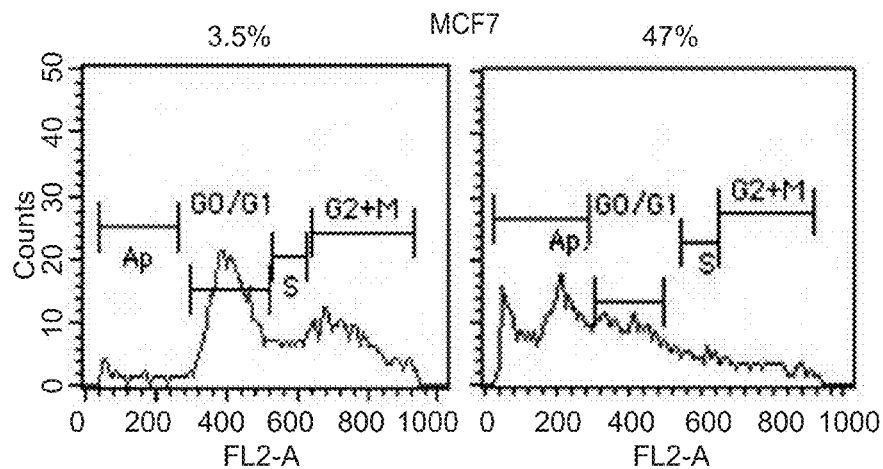
Figures 17I, 17J:
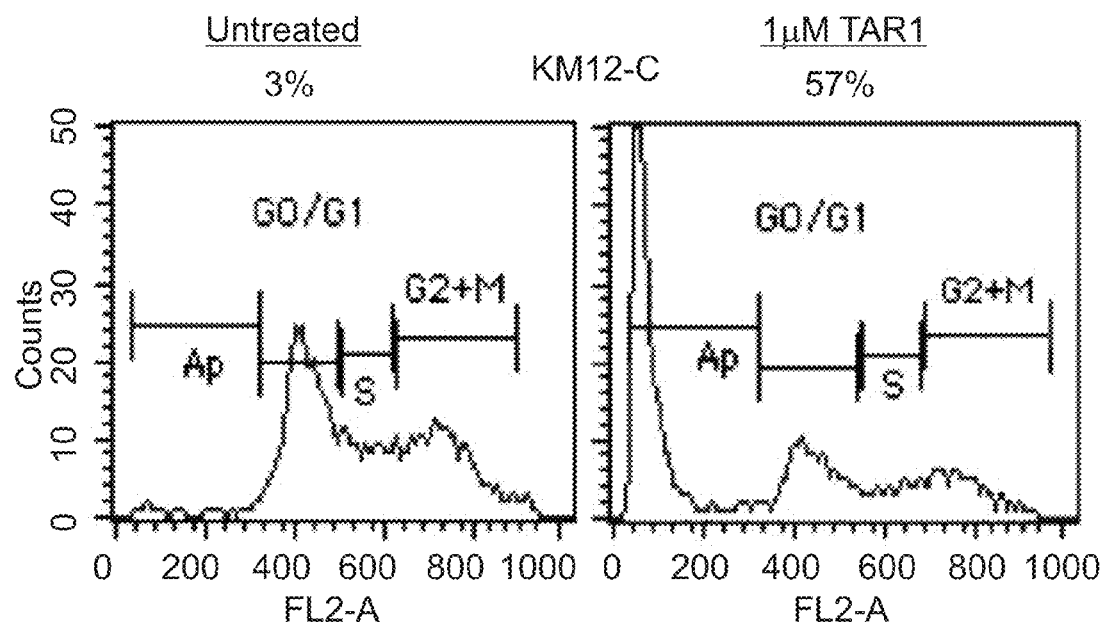
Figures 17K, 17L:
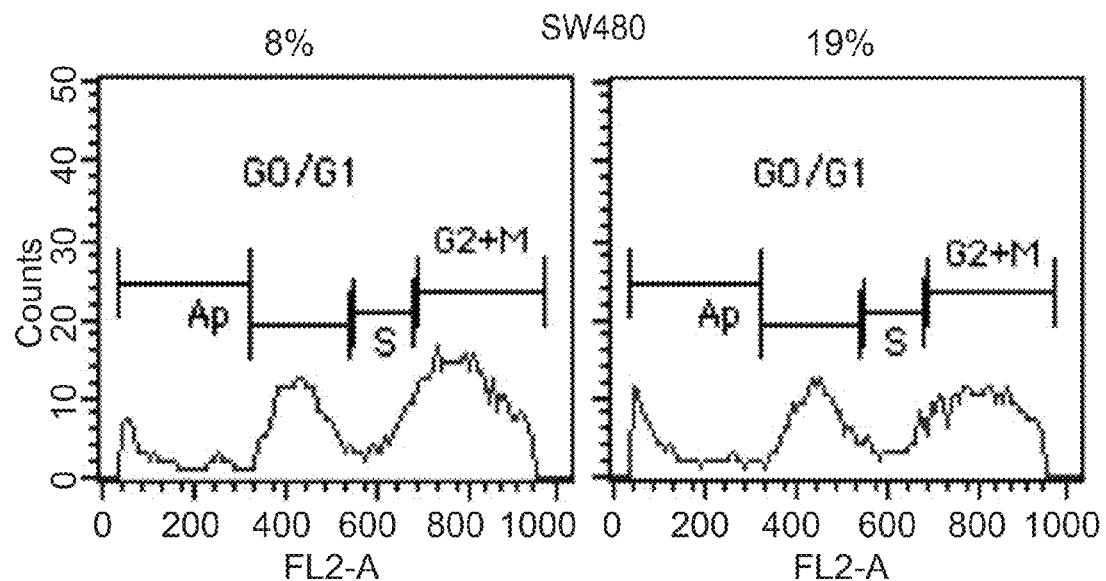
Figures 17M, 17N:
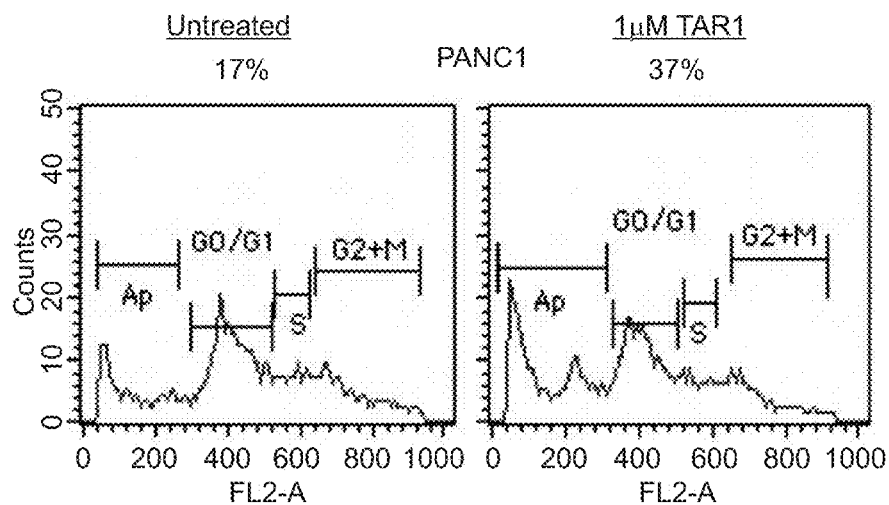
Figures 17O, 17P:
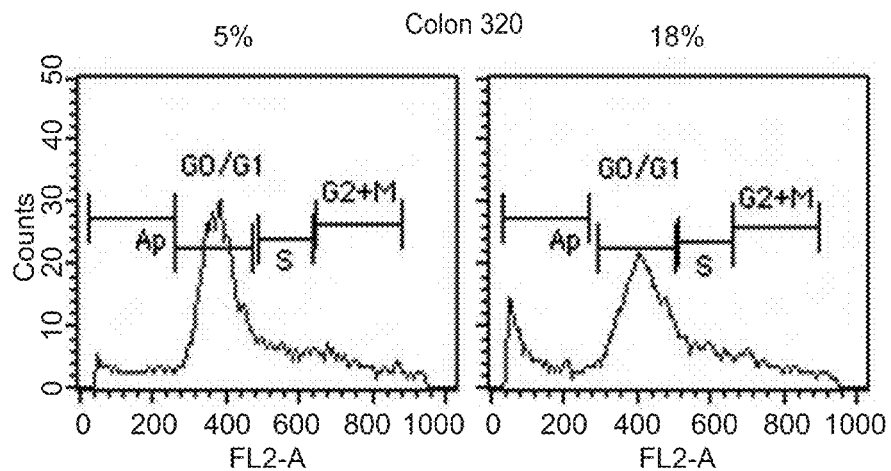
Figures 17Q, 17R:
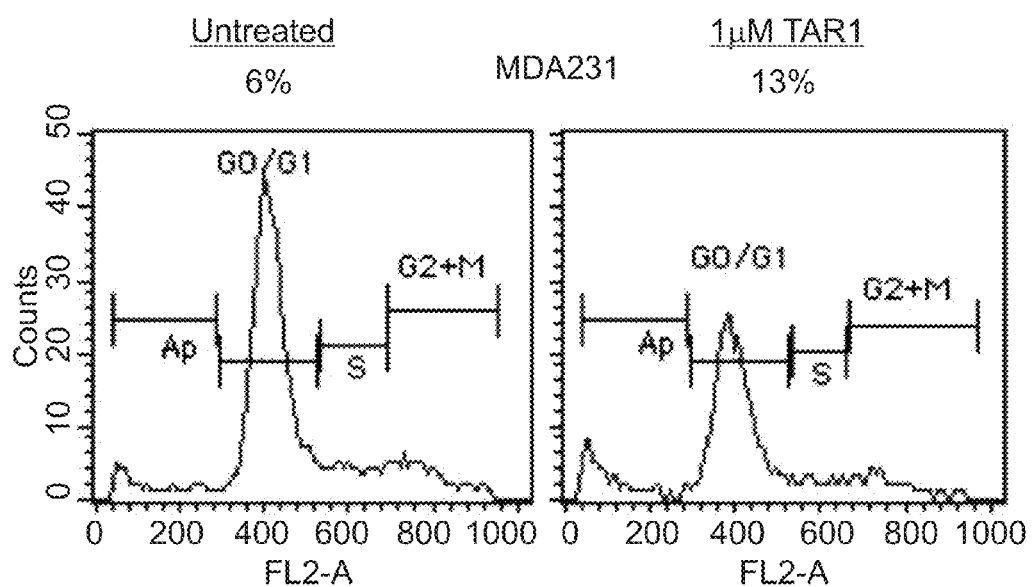

FIGS. 17a-r are FACS analyses depicting the effect of TAR1 (scFv-F2) on apoptosis in nine cell lines endogenously expressing different p53 mutations. LAN1 (FIGS. 17a-b), T47D (FIGS. 17c-d), SKBR3 (FIGS. 17e-f), MCF7 (FIGS. 17g-h), KM12-C (FIGS. 17i-j), SW480 (FIGS. 17k-l), PANC1 (FIGS. 17m-n), Colon 320 (FIGS. 17o-p) and MDA231 (FIGS. 17q-r) cancerous cell lines were treated for 24 hours with 1 μM TAR1 (FIGS. 17b, d, f, h, j, l, n, p and r) or remained untreated (FIGS. 17a, c, e, g, i, l, m, o and q), following which the cells were subjected to Propidium Iodide FACS analysis as described in FIGS. 15a-h. The percentages of cells in the sub-G1 fraction are indicated. Note the significant increase in apoptosis following treatment with the TAR1 antibody.

FIGS. 18a-b are schematic illustrations despicting the construction of a phage including the PEP internalization peptide. FIG. 18a—Schematic presentation of phage PEP cloning into the fd-Tet f88-4 vector (Modified from Chen, L., et al., 2004, Chem. & Biol. 11, 1081-1091). Also shown is the sequence of the PEP peptide (EFGACRGDCLGA; SEQ ID NO:136); FIG. 18b—The fd-Tet phage f88-4 vector displaying PEP peptide fused to ~150 copies of the pVIII by cloning into HindIII and PstI sites of the recombinant copy of pVIII gene under the regulation of tac promoter. Note that in order to direct the phage to deliver the anti-p53 antibody of the present invention (e.g., TAR1) into the nucleus, a nuclear localization signal (NLS) peptide (SEQ ID NO:134) can be fused to the antibody and this fusion protein can be cloned upstream of the phage protein III (FIG. 18b) to produce a phage that displays TAR1-NLS on its protein III.

Figures 19A, 19B, 19C:
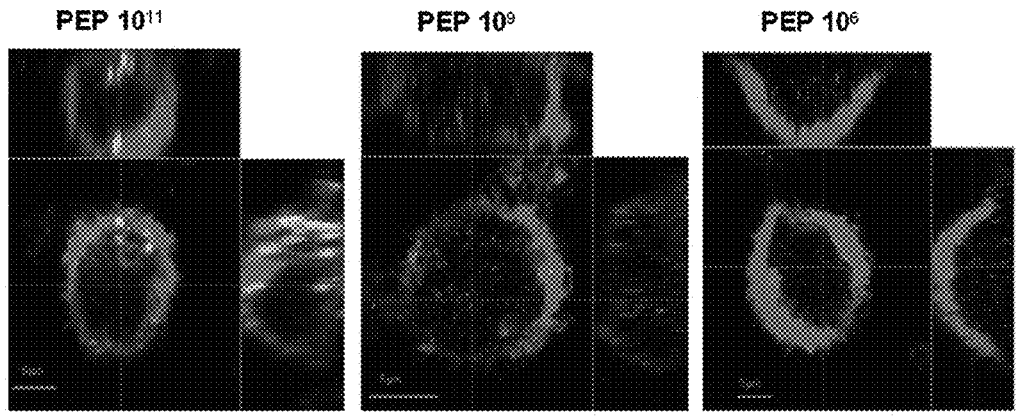

FIGS. 19a-c are confocal microscope images depicting immunofluorescence analyses of phage PEP in CHO cells and demonstrating that internalization of phage is dependent on phage concentration. CHO cells were incubated for 48 hours with membrane red molecular dye (CM-DiI molecular probe) in the presence of the indicated concentrations of phage PEP ($10^{11}$—FIG. 19a; $10^9$—FIG. 19b; $10^6$—FIG. 19c; phage per well). Internalized phage particles (in green) were detected with mouse anti M13 antibody followed by goat anti mouse cy2 conjugated antibody. Cells were visualized using confocal microscopy. Note that the internalization of the phage PEP is concentration dependent; the number of phages detected inside the cells is in direct correlation to the concentration of phages in the medium, as judged by higher intensity of green labeling inside the cell.

FIGS. 20a-w are confocal microscope images depicting immunofluorescence analyses of phage PEP in CHO cells and demonstrating the penetration of the phage into the mammalian CHO cells. Shown are a confocal series of in depth cellular slices of CHO cells which were incubated for 48 hours with membrane molecular dye and phage PEP at a final concentration of $10^{11}$ phage per well. Internalized phage particles were detected with mouse anti M13 antibody followed by goat anti mouse cy2 conjugated antibody (in green). Membrane was visualyzed with CM-DiI molecular probe (in red).

Figure 21:
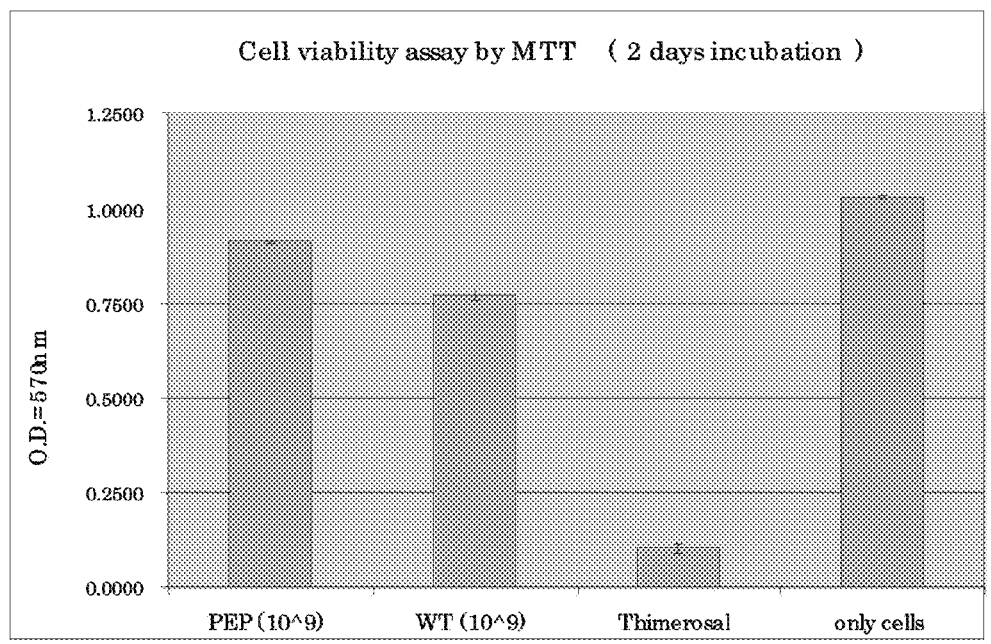

FIG. 21 is a bar graph depicting MTT analysis of CHO cells following incubation with phage PEP. CHO cells were incubated for 48 hours with $10^9$ pfu of phage PEP, wild type (W.T.) phage, Timirosal (a control for cell killing) and PBS (cells only) and the cell viability was measured by the MTT analysis. Error bars represent standard deviation values calculated from three independent experiments, with four repeats in each. Note that the phage PEP is non toxic to CHO cells.

DESCRIPTION OF THE PREFERRED EMBODIMENTS

The present invention is of isolated polypeptides, isolated polynucleotides or expression vectors encoding same which can specifically bind an exposed epitope shared by mutant, but not wild type, p53 protein. Specifically, the present invention can be used to induce apoptosis and treat a p53-related cancer. In addition, the present invention can be used to diagnose a p53-related cancer in a subject.

The principles and operation of the isolated polypeptide capable of binding the exposed epitope shared by mutant p53 proteins according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The tumor suppressor gene p53 inhibits tumor growth primarily via induction of apoptosis. The involvement of p53 mutants in cancer progression was suggested to be associated with either trans-dominant suppression of wild-type p53 or wild-type p53-independent oncogenic "gain of function". Given the active role of p53 mutants in promoting tumorigenicity, efforts have been made to inactivate their function or to revert them into a wild-type phenotype. These include the introduction of second site suppressor mutations, synthetic peptides derived from the C-terminus of the p53 protein, or the CDB3 derived compound and low molecular weight compounds that were shown to restore wild type conformation, transcriptional trans-activation and to induce apoptosis in cells and in human tumor xenografts carrying mutant p53. However, such peptides and compounds lack the ability to distinguish between the wild-type and mutant form of p53, a property crucial for targeted treatment.

Previous studies were aimed at developing novel anti cancer treatment/diagnostic modalities which specifically target/recognize a broad range of p53 mutants and not the wild-type p53 protein. For example, Gannon J V, and co-workers generated a mouse monoclonal antibody [PAb-240, EMBO J. 1990 9(5):1595-602] directed against the common epitope of p53 mutant proteins. However, attempts to produce a single chain antibody from this hybridoma clone failed thus limiting the therapeutic application of such antibody. Indeed use of this antibody was suggested only for diagnostic applications. Recently, a single-chain Fv (scFv) mouse antibody (ME1) was isolated and was found capable of binding exclusively mutant p53 proteins and not the wild type p53 protein with an affinity of $10^{-7}$ M (Govorko D, Cohen G and Solomon B., 2001, J. Immunol. Methods. 258: 169-81). However, although this antibody presents a useful tool for clarifying the role of mutant p53 in tumor transformation, due to its mouse origin and its moderate affinity towards the mutated p53, its therapeutic application is limited.

While reducing the present invention to practice, the present inventors have isolated scFvs from a human synthetic combinatorial library [Azriel-Rosenfeld R, et al., 2004, J. Mol. Biol. 335(1): 177-92] which are capable of specifically binding an epitope shared by mutant p53 proteins, but not wild type p53, with a binding affinity of less than 25 nanomolar (nM).

As is shown in FIGS. 2a-b, 3 and 9 and is described in Examples 1 and 2 of the Examples section which follows, the F2 (TAR1) and E6 scFvs exhibited an affinity of $1.1 \times 10^{-8}$ and $4.6 \times 10^{-14}$ M, respectively towards the common epitope (SEQ ID NO:1) shared by mutant, but not wild type, p53 protein. In addition, BIAcore analysis of the A6 scFv revealed a binding constant of $2.3 \times 10^{-8}$ M towards the common epitope (SEQ ID NO:1) (data not shown). Similarly, the F2 scFv (TAR1) exhibited high affinity towards whole p53 proteins expressing severe (R175H) or intermediate (R248W) conformational mutations but not towards the wild type p53 protein. In addition, the TAR1 antibody was shown capable of restoring wild type conformation to mutant p53 core domains (FIGS. 10a-d, 11a-b and 12, Example 5 of the Examples section which follows) and the transcriptional transactivation function of wild type p53 (e.g., activation of wild-type specific target genes such as p21, MDM2 and Bax) while preventing the transcriptional activation of mutant P53 (e.g., downregulation of Egr1) (FIGS. 13a-h, 14 and Example 6 of the Examples section which follows). Such antibodies administered as a polypeptide, displayed on phage or expressed as intrabodies can thus be used for the effective treatment of p53-related cancer.

Thus, according to one aspect of the present invention there is provided an isolated polypeptide comprising an amino acid sequence capable of specifically binding an exposed epitope shared by p53 mutant proteins and not by wild type p53 protein, wherein an affinity of the specific binding is less than 25 nM.

As used herein the phrase "p53 protein" refers to the TP53 tumor protein p53, a nuclear protein which plays an essential role in the regulation of cell cycle, specifically in the transition from G0 to G1. p53 is a DNA-binding protein containing DNA-binding, oligomerization and transcription activation domains. p53 has been cloned from a variety of sources including, but not limited to, human [GenBank Accession No. NP_000537 (protein) and NM_000546 (mRNA)], mouse [GenBank Accession No. NP_035770 (protein) and NM_011640 (mRNA)], rat [GenBank Accession No. NP_112251 (protein) and NM_030989 (mRNA)] and Zebrafish [GenBank Accession No. NP 571402 (protein) and NM_131327 (mRNA)] and the coding sequences of p53 proteins are available via, for example, the NCBI web site.

The phrase "exposed epitope" refers to any antigenic determinant which in the wild type p53 protein is hidden within a hydrophobic core, but in p53 mutants which undergo intermediate or severe conformational changes is exposed to the outer surface of the protein. For example, such an exposed epitope can be the FRHSVV (SEQ ID NO:1) which is exposed in p53 proteins carrying the R248W and R175H, intermediate and severe mutations, but is hidden in the wild type p53 protein.

The phrase "affinity of the specific binding" refers to the binding affinity of the isolated polypeptide of the present invention to the exposed epitope shared by p53 mutant proteins. Such affinity can be measured using methods known in the arts [e.g., the BIAcore system (Biacore AB, Uppsala, Sweden), scatchard plot analysis] in which the dissociation ($K_d$) or binding $K_a$) constants can be calculated. According to this aspect of the present invention the affinity of the polypeptide of the present invention is characterized with a dissociation constant of less than 25 nM, preferably, less than 12 nM, preferably less than 1 nM, preferably less than 0.1 nM and even more preferably less than 0.01 nM.

Antibodies of this aspect of the present invention are capable of neutralizing activity of mutant p53 such as preventing its transcriptional activation activity (as demonstrated in FIGS. 13-14 and Example 6 of the Examples section which follows).

The isolated polypeptide of the present invention can be any synthetic, natural occurring or recombinantly expressed polypeptide which is capable of binding the exposed epitope shared by p53 mutant proteins but not the wild type p53 protein. Such a polypeptide is preferably an antibody or an antibody fragment.

The term "antibody" as used in this invention includes intact molecules as well as functional fragments thereof, such as Fab, F(ab')2, Fv or single domain molecules such as VH and VL to an epitope of an antigen at least partially generated by recombinant DNA technology. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule (scFv); and (6) Single domain antibodies are composed of a single VH or VL domains which exhibit sufficient affinity to the antigen.

The term "antibody" as used herein is not only inclusive of antibodies generated by immunization and recombinant phage display techniques, but also includes any polypeptide which is generated to include at least one complementary-determining region (CDR) which is capable of specifically binding the exposed epitope shared by mutant p53 but not wild type p53 protein. Thus, the antibody of the present invention can be expressed (as is further described hereinbelow) from a polynucleotide sequence including a coding sequence of at least one CDR of an antibody.

To increase avidity of the antibody towards the exposed epitope shared by mutant but not wild type p53, antibodies of the present invention are preferably at least bivalent. Such antibodies can be cloned into an IgG subtype (which is bivalent), an IgM (which is penta-valent) or selected of such subtypes using methods known in the arts. Alternatively, the affinity of single chain variable fragments (scFvs) can be increased by tetramerization on streptavidin following site-specific biotinylation by the enzyme BirA, essentially as described in Cloutier S M, et al., 2000, Mol. Immunol. 37(17): 1067-77.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods of producing scFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementary-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions (FR) are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332: 323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991). The construction of large human synthetic single-chain Fv antibody libraries where in vivo formed CDRs are shuffled combinatorially onto germline-derived human variable-region frameworks are also available [Azriel-Rosenfeld R, et al., 2004. A human synthetic combinatorial library of arrayable single-chain antibodies based on shuffling in vivo formed CDRs into general framework regions. J. Mol. Biol. 335(1): 177-92]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. To direct the expression of an antibody to the cell nuclei, a nuclear localization signal coding sequence (e.g., DPKKKRKV; SEQ ID NO:134) is preferably ligated to a nucleic acid construct encoding the antibody, preferably, downstream of the coding sequence of the antibody. A non-limiting example of such a configuration is provided under the Materials and Experimental Methods of the Examples section which follows. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., (Gly$_4$Ser)$_3$ and expressed as a single chain molecule. To inhibit marker activity in a cell, the expression vector encoding the intracellular antibody is introduced into the cell by standard transfection methods, as discussed hereinbefore.

According to preferred embodiments of this aspect of the present invention the polypeptide of the present invention is a recombinant polypeptide comprising at least one CDR sequence as set forth by SEQ ID NOs:8-112. Examples include, but are not limited to the F2 scFv (SEQ ID NO:113), the E6 scFv (SEQ ID NO:114) and the A6 scFv (SEQ ID NO:115 and/or any IgG clone including at least one CDR or scFv sequence. Preferably, the polypeptide of the present invention comprises at least one CDR as set forth by SEQ ID NOs:39-41, 45-47 and 60-62.

According to preferred embodiments of this aspect of the present invention the polypeptide of the present invention can be a Fab fragment, an Fv fragment, a single chain antibody and a single domain antibody. Non-limiting examples of the single chain antibody which can be used along with the present invention include the F2 scFv (SEQ ID NO:113) and E6 scFv (SEQ ID NO:114) and A6 scFv (SEQ ID NO:115), all of which exhibit high affinity (with a dissociation constant being less than 25 nM) towards to exposed epitope shared by p53 mutants by not the wild type p53.

As is shown in Tables 3-5 of the Examples section which follows, the present inventors have isolated twenty different scFvs that specifically bind the mutant p53 common epitope (SEQ ID NO:1). These scFvs share an identical heavy variable region (Table 3) and differ in their light variable region (Table 4). Table 5 presents the unique CDRs of the variable light chains which can specifically bind a p53 epitope shared by various mutants of the p53 protein but not by the wild type p53 protein.

Thus, according to another aspect of the present invention there is provided an isolated polypeptide comprising at least one CDR selected from the group consisting of CDR SEQ ID NOs:8-112.

As is further described in the Examples section which follows and in the description hereinbelow, the isolated polypeptide of the present invention can be used in various in vitro, ex vivo and in vivo applications. To increase the stability, bioavailability, affinity and avidity to the target epitope (i.e., to the exposed epitope shared by mutants but not wild type p53 protein), the present invention can also employ peptides, peptide analogues or mimetics thereof derived from the CDRs of the present invention (e.g., SEQ ID NOs:8-112).

Such peptides, peptide analogues or mimetics thereof are preferably short amino acid sequences of at least 4-5 amino acids, preferably at least 6, more preferably, at least 7, more preferably, in the range of 8-20, more preferably in the range of 8-15, even more preferably, in the range of 11-15 amino acids which are derived from at least one CDRs of the CDRs set forth by SEQ ID NOs:8-112.

The term "peptide" as used herein encompasses native peptides (either degradation products, synthetically synthesized peptides or recombinant peptides) and as mentioned hereinabove, peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH$_2$—NH, CH$_2$—S, CH$_2$—S=O, O=C—NH, CH$_2$—O, CH$_2$—CH$_2$, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclicization does not severely interfere with peptide characteristics, cyclic forms of the peptide can also be utilized.

The isolated polypeptide of the present invention (e.g., peptide including at least one of the CDRs set forth by SEQ ID NOs:8-112) can be biochemically synthesized using standard solid phase techniques. These methods include exclusive solid phase synthesis, partial solid phase synthesis methods, fragment condensation and classical solution synthesis. These methods are preferably used when the peptide is relatively short (i.e., 10 kDa) and/or when it cannot be produced by recombinant techniques (i.e., not encoded by a nucleic acid sequence) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680; Brogli et al., (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

As used herein the term "mimetics" refers to molecular structures, which serve as substitutes for the peptide of the present invention in specifically binding the exposed epitope of p53 shared by mutants, but not wild type p53 protein (Morgan et al. (1989) Ann. Reports Med. Chem. 24:243-252 for a review of peptide mimetics).

Peptide mimetics, as used herein, include synthetic structures (known and yet unknown), which may or may not contain amino acids and/or peptide bonds, but retain the structural and functional features of specifically binding the exposed epitope of p53 shared by mutants, but not the wild type p53 protein. Types of amino acids which can be utilized to generate mimetics are further described hereinbelow. The term, "peptide mimetics" also includes peptoids and oligopeptoids, which are peptides or oligomers of N-substituted amino acids [Simon et al. (1972) Proc. Natl. Acad. Sci. USA 89:9367-9371]. Further included as peptide mimetics are peptide libraries, which are collections of peptides designed to be of a given amino acid length and representing all conceivable sequences of amino acids corresponding thereto.

Generation of peptide mimetics, as described hereinabove, is effected using various approaches, including, for example, display techniques, using a plurality of display vehicles (such as phages, viruses or bacteria) each displaying a short peptide sequence as described hereinabove. Methods of constructing and screening peptide display libraries are well known in the art. Such methods are described in, for example, Young A C, et al., "The three-dimensional structures of a polysaccharide binding antibody to Cryptococcus neoformans and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47): 15430-5; Davies E L et al., "Selection of specific phage-display antibodies using libraries derived from chicken immunoglobulin genes" J Immunol Methods 1995 Oct. 12; 186(1):125-35; Jones C RT al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13): 9533-8, which are incorporated herein by reference.

Peptide mimetics can also be uncovered using computational biology. For example, various compounds can be computationally analyzed for the ability to specifically bind the exposed epitope of p53 shared by mutants, but not wild type p53 protein using a variety of three-dimensional computational tools. Software programs useful for displaying three-dimensional structural models, such as RIBBONS (Carson, M., 1997. Methods in Enzymology 277, 25), O (Jones, T A. et al., 1991. Acta Crystallogr. A47, 110), DINO (DINO: Visualizing Structural Biology (2001); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model interactions between the exposed epitope of p53 (e.g., SEQ ID NO:1) and prospective peptide mimetics to thereby identify peptides which display the highest probability of specifically binding the exposed epitope shared by mutants, but not wild type, p53 protein. Computational modeling of protein-peptide interactions has been successfully used in rational drug design, for further detail, see Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109, and Mauro M J. et al., 2002. J Clin Oncol. 20, 325-34.

Regardless of the methods employed, peptide mimetics generated using the above-teachings can be qualified using the assays described in the Examples section which follows (e.g., binding affinity assay).

As is mentioned before, the isolated polypeptide of the present invention can be also recombinantly expressed in cells (e.g., mammalian cells, bacterial cells, plant cells, yeast cells) as part of a nucleic acid construct containing a polynucleotide encoding for example, the Fab fragment, the scFV, the complete IgG antibody or any of the CDRs of the isolated polypeptide of the present invention.

To express the recombinant isolated polypeptide of the present invention in mammalian cells, a polynucleotide sequence encoding at least one CDR sequence as set forth by SEQ ID NOs:8-112 is preferably ligated into a nucleic acid construct suitable for mammalian cell expression. Such a polynucleotide can be, for example, the polynucleotide set forth by SEQ ID NO:113 (for the F2 scFv), SEQ ID NO:114 (for the E6 scFv), SEQ ID NO:115 (for the A6 scFv). The nucleic acid construct includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of recombinant isolated antibody mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of the isolated polypeptide of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Other than containing the necessary elements for the transcription and translation of the inserted coding sequence, the expression construct of the present invention can also include sequences engineered to enhance stability, production, purification, secretion, yield or toxicity of the expressed peptide.

For secretion of the isolated polypeptide of the present invention the nucleic acid construct of the present invention typically includes a signal sequence for secretion of the peptide from a host cell in which it is placed. In addition, the expression of a fusion protein or a cleavable fusion protein comprising Met variant of the present invention and a heterologous protein can be engineered. Such a fusion protein can be designed so that the fusion protein can be readily isolated by affinity chromatography; e.g., by immobilization on a column specific for the heterologous protein. Where a cleavage site is engineered between the Met moiety and the heterologous protein, the Met moiety can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

It will be appreciated that a variety of prokaryotic or eukaryotic cells can be used as host-expression systems to express the isolated polypeptide of the present invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of the present invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

Other expression systems such as insects, plants and mammalian host cell systems are well known in the art and can also be used by the present invention.

Recovery of the recombinant polypeptide of the present invention is effected following an appropriate time in culture. The phrase "recovering the recombinant polypeptide" refers to collecting the whole growth (e.g., fermentation) medium containing the polypeptide and need not imply additional steps of separation or purification. Not withstanding the above, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

It will be appreciated that the isolated polypeptide of the present invention (which acts as an anti p53 antibody) can be also expressed in the target cells which express mutant p53 protein (e.g., cancer cells harboring a severe p53 mutation such as R175H) to thereby form an intracellular antibody as described hereinabove. This is of particular importance especially in the case of p53 which is a nuclear protein and thus is relatively more "resistance" to conventional antibody therapy. As is shown in FIGS. 4a-j, 15a-h and 16a-d and is described in Example 3 of the Examples section which follows, the F2 scFv antibody (TAR1) was capable of inducing apoptosis in human lung carcinoma or human colon cancer cells specifically expressing the mutant R175H p53 protein (with the exposed epitope set forth by SEQ ID NO:1). In addition, treatment of cancerous cell lines expressing various endogenous p53 mutant proteins with TAR1 resulted in a significant increase in apoptosis (FIGS. 17a-r, Example 3). Moreover, cells harboring the mutant p53 protein (R175H) which were stably transfected to express the F2 scFv (TAR1) antibody of the present invention exhibited reduced colony formation capability manifested in reduced number of formed colonies as well as reduced size of the formed colonies (FIGS. 5, 6a-d, Examples 3 and 4 of the Examples section which follows).

Thus, according to yet an additional aspect of the present invention, there is provided a method of inducing apoptosis and/or growth arrest of cancer cells. The method is effected by contacting with or expressing in the cancer cells the isolated polypeptide of the present invention (which is extensively described hereinabove), thereby inducing apoptosis and/or growth arrest of the cancer cells.

As used herein the term "apoptosis" refers to programmed cell death whereby the cell executes a "cell suicide" program. Apoptosis plays an important role in a number of physiological events including embryogenesis, regulation of the immune system, and homeostasis. Thus, apoptosis can be in response to diverse signals such as limb and neural development, neurodegenerative diseases, radiotherapy and chemotherapy. Apoptotic processes are usually characterized by uncoupling of mitochondrial oxidation, drop in levels of nicotinamide adenine dinucleotide phosphate [NAD(P)H], release of cytochrome c, activation of caspases, DNA fragmentation and externalization of phosphatidylserine (a membrane phospholipid normally restricted to the inner leaflet of the lipid bilayer) to the outer leaflet of the plasma membrane.

As used herein the phrase "growth arrest" refers to inhibition of cell growth in vitro, ex vivo (i.e., when cells are derived from an individual and are cultured in a tissue culture) and/or in vivo (in a tumor of an individual). In case in vitro or ex vivo conditions are used, the growth arrest can be detected by following colony formation (by counting the number of colonies), cell area, number of cells in a colony and the like using various methods known in the art. In case in vivo conditions are utilized, the growth arrest can be also monitored by following the size and shape of tumor and/or the presence of tumor metastases using various histological and immunological staining methods known to any one skilled in the art of pathology.

According to the method of this aspect of the present invention, the cancer cells in which apoptosis is induced according to the method of this aspect of the present invention specifically express the exposed epitope shared by mutant, but not wild type p53 protein (e.g., SEQ ID NO:1). Such cancer cells can harbor a severe or intermediate p53 mutation as described hereinabove. Such cancer cells can be derived from any kind of tumor, including solid tumors (e.g., breast cancer, colon cancer, lung cancer, hepatocellular carcinomas, osteogenic sarcomas, colorectal cancer, glioblastomas, esophageal carcinoma, bladder cancer, squamous cell carcinomas) and non-solid tumors (e.g., leukemia and lymphoma). In addition, such cells can be derived by mutagenesis or transfection of normal cells with an oncogene using methods known in the art.

According to the method of this aspect of the present invention, the isolated polypeptide of the present invention is contacted with or expressed in the cancer cells of the present invention. It will be appreciated that since p53 is expressed in the cell nuclei, the isolated polypeptide of the present invention is preferably a small polypeptide [e.g., a CDR-containing polypeptide or an scFv such as the F2 scFv (SEQ ID NO:113)] rather than a large molecule (such as an IgG molecule) which can therefore more easily penetrate the cell and nuclear membranes.

To facilitate the penetration of the isolated polypeptide to the cell nuclei, the isolated polypeptide can be covalently attached to a hydrophobic moiety or be expressed as a fusion gene with the hydrophobic moiety (such as in the case of the TAT-scFv F2/His expression plasmids described in the "General Materials and Experimental Methods" of the Examples section which follows). The hydrophobic moiety can be any substance which is nonpolar and generally immiscible with water such as a hydrophobic residue (portion) of a hydrophobic substance. Non-limiting examples of hydrophobic substances include, but are not limited to, substituted and unsubstituted, saturated and unsaturated hydrocarbons, where the hydrocarbon can be an aliphatic, an alicyclic or an aromatic. Preferably, the hydrocarbon bears a functional group which enables attachment thereof to an amino acid residue. Representative examples of such functional groups include, without limitation, a free carboxylic acid (C(=O)OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl), a free N-carbamic group (OC(=O)—NR'—, where R' is as defined above), a thionyl group (S(=O)$_2$A, where A is halide as defined above) and the like. For example, such a hydrophobic moiety can be a fatty acid such as myristic acid, lauric acid, palmitic acid, stearic acid (C18), oleic acid, linolenic acid and arachidonic acid.

The isolated polypeptide of the present invention can be administered to the cells using methods known in the art such as, the addition of the isolated polypeptide to the cell environment such as blood, plasma, buffers, tissue culture medium and the like.

Alternatively, the isolated polypeptide of the present invention can be expressed using a nucleic acid construct in cells to form intrabodies as described hereinabove.

Additionally or alternatively, the anti-p53 antibody of the present invention (e.g., the TAR1 antibody) can be presented on a viral display vehicle such as a filamentous phage and be used in a therapeutically effective amount to induce apoptosis and/or growth arrest of cancer cells. The present inventors have previously demonstrated that such viral display vehicles (i.e., phages) are inert vehicles and suitable for carrying active antibody fragments to the CNS (U.S. Pat. Appl. No. 20040013647 to Solomon, Beka et al.).

It will be appreciated that the viral display vehicle of the present invention can be designed to enable presentation of the p53 antibody of the present invention (e.g., TAR1) within a cell. As is shown in FIGS. 18-21 and is described in Example 7 of the Examples section which follows, a viral display vehicle containing a PTD (protein transduction domain) [e.g., the PEP peptide (SEQ ID NO:136) which enables internalization into a mammalian cell; shown in FIGS. 18*a-b*] was capable of penetrating into mammalian CHO cells. For penetration into the nucleus, the viral vector can further include the NLS peptide (SEQ ID NO:134) conjugated to the displayed antibody. The constructed phage will present a PTD on its coat protein VIII and the antibody fused to the NLS peptide on its protein III (See FIGS. 18*a-b*).

Thus, viral display vehicles which present the anti-p53 antibody of the present invention can be administered to an individual in need thereof and be targeted to the nuclei of the cells of interest. For example, for brain tumors, the viral display vehicle can be administered to the individual by intranasal application and thereby reach various brain regions such as the cortex and the hippocampus.

The apoptosis induced by the isolated polypeptide, the nucleic acid construct and/or the viral display vehicle of the present invention can be detected using various methods known in the art.

Ethidium homodimer-1 staining—Apoptosis can be detected by dyes specifically binding to cells with compromised membranes, i.e., dead cells. Briefly, unfixed cells such as cells in suspension, tissue culture, tissue sections and the like are stained with the fluorescent dye Ethidium homodimer-1 (excitation, 495 nm; emission, 635 nm). In this assay, live cells have a green fluorescent cytoplasm but no EthD-1 signal, whereas dead cells lack the green fluorescence and are stained with EthD-1.

Tunnel assay (Roche, Basel, Switzerland)—labels DNA breaks which are characteristics of cells undergoing apoptosis with fluorescein (excitation 450-500 nm, emission 515-565 nm).

Live/dead viability/cytotoxicity two-color fluorescence assay (Molecular Probes, Inc., L-3224, Eugene, Oreg., USA)—This assay measures intracellular esterase activity with a cell-permeable substrate (Calcein-AM) which is converted by live cells to a fluorescent derivative (polyanion calcein, excitation, 495 nm; emission, 515 nm) which is thereafter retained by the intact plasma membrane of live cells.

FACS analysis—using molecules capable of specifically binding cells undergoing apoptosis, such as propidium iodide and Annexin V. Annexins V is a human protein characterized by calcium-mediated, high affinity binding to phosphatidylserine which undergoes externalization to the outer side of the plasma membrane during early apoptosis.

DNA fragmentation by gel electrophoresis—Briefly, DNA is extracted from unfixed cells and is subjected to gel electrophoresis (e.g., 1.5-2% agarose gel) and the degree of DNA fragmentation is evaluated using any DNA stain such as Ethidium bromide, Syber Green and the like.

As is further shown in FIGS. 8*a-f* and is described in Example 4 of the Examples section which follows, the F2 scFv (TAR1) antibody was capable of inhibiting tumor growth in vivo. These results strongly suggest the use of the isolated polypeptide, the polynucleotide and/or expression vector encoding same of the present invention in treating a p53-related cancer.

Thus, according to yet an additional aspect of the present invention there is provided a method of treating a subject suffering from or being predisposed to a p53-related cancer. The method is effected by administering to or expressing in cells of the subject a therapeutically effective amount of the isolated polypeptide of the present invention thereby treating the p53-related cancer in the subject.

The term "treating" refers to inhibiting or arresting the development of a disease, disorder or condition (e.g., a p53-related cancer) and/or causing the reduction, remission, or regression of a disease, disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" (or "individual" which is interchangeably used herein) refer to a mammal, preferably a human being at any age which suffers from a p53-related cancer. Preferably, this term encompasses individuals who are at risk to develop the p53-related cancer, i.e., individuals who are predisposed to a p53-related cancer. Such individuals can be carriers of a germ-line mutation in the p53 gene (GenBank Accession No. NM_000546) such as in the case of Li-Fraumeni syndrome.

As used herein "p53-related cancer" refers to any cancer in which p53 is related to the onset or progression thereof. Such a cancer can be caused by a mutation in the p53 gene [GenBank Accession Nos. NC_000017: 7512464-7531642 (genomic region); NM_000546 (mRNA); NP_000537 (protein)] leading to an abnormal structure and/or function of the p53 protein. Such a mutation can be a missense, nonsense, splice mutation, promoter mutation, deletion, insertion, duplication and the like. As is mentioned hereinabove, various mutations in the p53 protein result in intermediate or severe conformational changes leading to abnormal function of the p53 protein. Non-limiting examples of p53-related cancer include those caused by germline mutations in the p53 gene (e.g., in the case of Li-Fraumeni syndrome 1, OMIM #151623) as well as those caused by somatic mutations in the p53 gene, such as hepatocellular carcinomas, osteogenic sarcomas, colorectal cancer, lung cancer, glioblastomas, esophageal carcinoma, bladder cancer, squamous cell carcinomas, leukemia and lymphoma.

As used herein the phrase "cells of a subject" includes any cells which are derived from the subject and are taken out of the subject (i.e., ex vivo gene therapy) or cells which are part of the subject (i.e., in vivo gene therapy as described hereinabove).

As used herein the phrase "therapeutically effective amount" refers to an amount of the isolated polypeptide of the present invention, the polynucleotide or expression vector encoding the same and/or the viral display vehicle which displays the anti-p53 antibody of the present invention, which is sufficient to exert the biological activity, i.e., binding the exposed epitope of p53 (as described hereinabove), inducing apoptosis and treating or preventing the p53-related cancer.

As is shown in FIG. 5 and is described in Example 3 of the Examples section which follows, the A4 scFv was capable of increasing the susceptibility of cancer cells to chemotherapy drugs. These results suggest the use of the isolated polypeptide, isolated polynucleotide, the expression vector encoding same and/or a pharmaceutical composition including same (as is further described hereinunder) together with conventional cancer treatment protocols utilizing e.g., chemotherapy drugs (i.e., combination therapy).

It will be appreciated that such a drug (e.g., a chemotherapy agent such as Mechlorethamine, Fluorouracil, Dacarbazine, Docetaxel, Carmustine, Vindesine) can be also conjugated to the isolated polypeptide of the present invention or form a part of the expression vector encoding same.

In addition, to increase the specific biological activity exerted by the isolated polypeptide of the present invention such a polypeptide can further include a cytotoxic agent (i.e., a drug) such as *Pseudomonas* exotoxins PE35, PE38, PE40, *Pseudomonas aeroginosa* exotoxin A (ETA'), and diphtheria toxin (DT390), to thereby form a specific immunotoxin. Such a cytotoxic agent can be attached to the isolated polypeptide or be part of polynucleotide expressed by the expression vector of the present invention.

Thus, according to one preferred embodiment of present invention, the isolated polypeptide of the present invention is fused or conjugated to a drug.

According to another preferred embodiment of the present invention the isolated polynucleotide and/or expression vector of the present invention further comprises an additional nucleic acid sequence encoding a drug.

It will be appreciated that such immunotoxins and/or chemotherapy agents can be generated using recombinant DNA techniques (e.g., by ligating the coding sequence of the agent molecule to the coding sequence of the isolated polypeptide of the present invention, usually downstream of the coding sequence of the isolated polypeptide) or by covalently conjugating the toxin or chemotherapy agents to the isolated polypeptide sequence (e.g., to the polypeptide set forth by SEQ ID NO:113, 114, or 115) by methods known in the art. For example by using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bisazido compounds (such as bis-(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The isolated polypeptide of the present invention, the polynucleotide and/or the nucleic acid construct encoding same can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the recombinant isolated polypeptide of the present invention, the polynucleotide and/or the viral diaply vehicle accountable for the biological effect (i.e., specific binding to the exposed epitope shared by mutant, but not wild type p53 protein, inducing apoptosis and/or treating a p53-related cancer).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition; stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the isolated polypeptide of the present invention or the polynucleotide or expression vector encoding same) effective to prevent, alleviate or ameliorate symptoms of a disorder (the p53-related cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the cancer cells expressing a mutant p53 protein [which results in exposure of the common epitope described hereinabove (e.g., SEQ ID NO:1)] with levels of the active ingredient which are sufficient to exert the biological activity (e.g., binding the exposed epitope of mutant p53 described hereinabove, inducing apoptosis and/or treat a p-53-related cancer) (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that introduction of nucleic acids of the present invention to the subject can be effected using any gene therapy methodology used in the art. Such as for example, by viral infection which offers several advantages over other methods such as lipofection, since higher transfection efficiency can be obtained due to the infectious nature of viruses.

Currently preferred in vivo nucleic acid transfer techniques (in vivo gene therapy) include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

It will be appreciated that since the isolated polypeptide of the present invention is capable of specifically binding the exposed epitope shared by mutant, but not wild type, p53 protein, such a polypeptide can be used in the diagnosis of a p53-related cancer in which such an epitope is exposed.

Thus, according to still an additional aspect of the present invention there is provided a method of diagnosing a p53-related cancer in a subject. The method is effected by: (a) contacting a biological sample of the subject with the isolated polypeptide of the present invention under conditions suitable for immunocomplex formation between the isolated polypeptide and the exposed epitope shared by p53 mutant proteins and not by wild type p53 protein; and (b) detecting formation of the immunocomplex, thereby diagnosing the cancer in the subject.

As used herein the phrase "diagnosing" refers to classifying a disease (a p53-related cancer) or a symptom, determining a severity of the disease, monitoring disease progression, forecasting an outcome of a disease and/or prospects of recovery.

As used herein "biological sample" refers to a sample of tissue or fluid isolated from a subject, including but not limited to, for example, blood cells, bone marrow cells and specifically macrophages, lymph fluid, various tumors, neuronal cells, dendritic cells, organs, and also samples of in vivo cell culture constituents. It should be noted that a "biological sample of the subject" may also optionally comprise a sample that has not been physically removed from the subject. Preferably, the biological sample used by the method of this aspect of the present invention is blood, lymph node biopsy, bone marrow aspirate and a tissue sample.

The cancer which is diagnosed using the method according to this aspect of the present invention can be any of the p53-related cancers described hereinabove. Preferably, the biological sample obtained from the subject is a blood sample, bone marrow aspirate, or a tissue specimen.

Diagnosis of cancer according to the present invention is effected by contacting the biological sample of the subject with the isolated polypeptide of the present invention under conditions suitable for immunocomplex formation.

As used herein the term "immunocomplex" refers to a complex formed between an antibody (e.g., the isolated polypeptide of the present invention) and its specific antigen (a p53 mutant protein in which the common epitope shared by p53 mutant proteins and not by wild type p53 protein is exposed).

The immunocomplex of the present invention can be formed at a variety of temperatures, salt concentration and pH values which may vary depending on the isolated polypeptide used and the cancer cells and those of skills in the art are capable of adjusting the conditions suitable for the formation of each immunocomplex.

According to the method of this aspect of the present invention, detection of immunocomplex formation is indicative of a diagnosis of the p53-related cancer. Various methods can be used to detect the immunocomplex of the present invention and those of skills in the art are capable of determining which method is suitable for each immunocomplex and/or the type of cells used for diagnosis.

For example, the immunocomplex can be detected by conventional immunohistochemistry or immunofluorescence, FACS, ELISA, Western blot and RIA analyses, or by a molecular weight-based approach.

Immunohistochemistry or immunofluorescence analyses—This method involves detection of an antigen (e.g., p53 mutant proteins harboring severe or intermediate mutations in which the common epitope shared by mutant, but not wild type p53 is exposed) in situ in fixed cells by antigen specific antibody (i.e., the isolated polypeptide of the present invention). The antigen specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

Fluorescence activated cell sorting (FACS)—This method involves detection of an antigen in situ in cells by antigen specific antibodies. The antigen specific antibodies are linked to fluorophores. Detection is by means of a cell sorting machine which reads the wavelength of light emitted from each cell as it passes through a light beam. This method may employ two or more antibodies simultaneously.

Enzyme linked immunosorbent assay (ELISA)—This method involves fixation of a sample (e.g., fixed cells or a proteinaceous solution) containing an antigen (e.g., p53 mutant proteins as described hereinabove) to a surface such as a well of a microtiter plate. An antigen specific antibody (i.e., the isolated polypeptide of the present invention) coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot—This method involves separation of a substrate (e.g., p53 mutant proteins as described hereinabove) from other protein by means of an acrylamide gel followed by transfer of the substrate to a membrane (e.g., nylon or PVDF). Presence of the substrate is then detected by an antibody specific to the substrate (i.e., the isolated polypeptide of the present invention), which are in turn detected by antibody binding reagents. Antibody binding reagents may be, for example, protein A, or other antibodies such as those in the ECL kit (Amersham Biosciences Inc, Piscataway, N.J., USA). Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis. It will be appreciated that in the case of the MHC-peptide complex, a non-denaturing gel electrophoresis is preferably employed.

Radio-immunoassay (RIA): In one version, this method involves precipitation of the desired antigen (e.g., p53 mutant proteins as described hereinabove) with a specific antibody (i.e., the isolated polypeptide of the present invention) and radiolabeled antibody binding protein (e.g., protein A labeled with $I^{125}$) immobilized on a precipitable carrier such as agarose beads. The number of counts in the precipitated pellet is proportional to the amount of antigen.

In an alternate version of the RIA, a labeled antigen and an unlabelled antibody binding protein are employed. A sample containing an unknown amount of antigen is added in varying amounts. The decrease in precipitated counts from the labeled antigen is proportional to the amount of antigen in the added sample.

Molecular weight-based approach—It will be appreciated that the immunocomplex formed between a p53 mutant protein as described hereinabove and the isolated polypeptide of the present invention exhibits a higher molecular weight than its components, i.e., the isolated polypeptide of the present invention or the a p53 mutant protein. Thus, methods capable of detecting such a change in the molecular weight can be also employed. For example, the immunocomplex can be detected by a gel retardation assay. Briefly, a non-denaturing acrylamide gel is loaded with samples containing the isolated polypeptide of the present invention and the p53 mutant protein before and after immunocomplex formation. A shift in the size (molecular weight) of the protein product as compared with its components is indicative of the presence of an immunocomplex. Such a shift to a higher molecular weight can be viewed using a non-specific protein staining such as silver stain or Commassie blue stain. Alternatively, the p53 mutant protein or isolated polypeptide of the present invention can be labeled (e.g., with a radioactive label) prior to gel electrophoresis. Additionally or alternatively, cells expressing the p53 mutant protein can be radioactively labeled prior to protein extraction.

In order to facilitate detection of immunocomplex formation, the polypeptide sequence of the isolated polypeptide of the present invention further comprises an amino acid sequence of a detectable label (i.e., an epitope tag). Such an amino acid sequence can be encoded by a nucleic acid sequence which is included in the expression vector of the present invention.

According to additional preferred embodiments of this aspect of the present invention, the isolated polypeptide of the present invention is attached to a detectable label such as biotin, digoxigenin and the like. Such a detectable label can be covalently attached to the isolated polypeptide of the present invention using methods well known in the arts.

The agents described hereinabove for detection of immunocomplex formation may be included in a diagnostic kit/article of manufacture preferably along with appropriate instructions for use and labels indicating FDA approval for use in diagnosing and/or assessing a severity of a p53-related cancer.

Such a kit can include, for example, at least one container including at least one of the above described diagnostic agents (e.g., the F2, E6 or A4 scFv antibodies) and an imaging reagent packed in another container (e.g., enzymes, secondary antibodies, buffers, chromogenic substrates, fluorogenic material). The kit may also include appropriate buffers and preservatives for improving the shelf-life of the kit.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley &

Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cells, Plasmids and Reagents—H1299 cells were obtained from American Type Culture Collection (Manassas, Va.) and were maintained in RPMI (Sigma, St. Louis, Mo.) supplemented with 10% fetal calf serum (Sigma). H1299-R175H cells stably expressing the hot spot mutation R175H were obtained from V. Rotter (Weizmann Institute of Science). Plasmids pCMV/myc and pCMV/myc/nuc were provided by I. Benhar (Tel Aviv University). pCMV-scFv F2 and pCMV/nuc-scFv F2 were constructed by removing the scFv F2 sequence from the corresponding pCC16 clone isolated from the human synthetic library (Azriel-Rosenfeld et al 2004 JMB 335, 177) and sub-cloning into the NcoI and NotI sites in pCMV and pCMV/nuc. The TAT-scFv F2/His expression plasmids were constructed by cloning the TAT peptide (RKKRRQRRRG; SEQ ID NO:133) into the NcoI site upstream the scFv in the vector pCANTAB6-Fv (expressing a non-relevant scFv) or into the NdeI site upstream the MBP in the vector pMalC-TNN-EGFP. Both vectors were provided by I. Benhar (Tel Aviv University). The Fv and the EGFP were replaced by scFv F2 cloned into the NcoI and NotI sites of both plasmids. The TAT-scFv F2-NLS/His expression plasmids were constructed by cloning the NLS peptide (DP-KKKRKV; SEQ ID NO:134) into the NotI site downstream the scFv.

Library screening—To identify scFvs that specifically bind the mutant p53 common epitope, a human synthetic combinatorial library of arrayable single-chain antibodies was screened. The construction and properties of the library is described in Azriel-Rosenfeld et al 2004 JMB 335, 177-192. The biopanning of the library was performed using biotinylated FRHSVV (SEQ ID NO:1) and Dynabeads M280 streptav id in (Dynal).

Rescue of the library—An aliquot of the bacterial library glycerol stock (about $1 \times 10^{10}$ clones) was inoculated into 2×YT containing 100 µg/ml ampicillin and 1% glucose (YTAG), and Grown at 37° C. until the $OD_{600}$ nm was 0.5. The cells were infected with M13K07 helper phage at a ratio of 1:20, incubated for 30 minutes at 37° C. without shaking and then transferred to a shaking incubator 37° C. for additional 30 minutes. The infected cells were pelleted at 3,300 g for 10 minutes, resuspended in 2×YT containing 100 µg/ml ampicillin and 50 mg/ml kanamycin (YTAK) and incubated overnight at 30° C. The cells were centrifuged at 4° C. for 10 minutes at 8000 g. PEG/NaCl was added to the supernatant (in a 1:5 ratio of PEG/NaCl to supernatant) and was incubated for 1 hour on ice. The phages were collected by a 30-minute centrifugation at 4° C. at 10,800 g and resuspended in PBS.

Biopanning—The streptavidin-dynabeads were equilibrated for 1 hour with MPBS (PBS containing 2% skim milk powder) on a rotator at room temperature. The beads were collected with a magnet and resuspended in MPBS containing 0.1% Tween-20. Phages were pre-incubated for 1 hour at room temperature with streptavidin-dynabeads alone. These two steps deplete and avoid anti-streptavidin binders. The phages were transferred to a fresh tube and 5 nmol of biotinylated FRHSVV (SEQ ID NO:1) peptide was added and incubated for 1 hour at room temperature on rotator. The equilibrated dynabeads were added to the phage-antigen mixture and incubates for 15 minutes at room temperature on rotator. The tube was left in the magnetic rack for 1 minute and then carefully aspirated. The beads were washed 6 times with 1 ml MPBS containing 0.1% Tween-20. The phages were then eluted from the beads using 1 ml 100 mM TEA (Triethylamine). The phages solution was immediately neutralized by transferring to a tube containing 0.5 ml 1.0 M Tris (HCl) pH 7. The panning output was determined by plating serial dilutions of TG-1 infected cells.

Monoclonal phage preparation—Individual colonies from the output plates were picked and inoculated into 100 µl YTAG in sterile 96-well plates. The phages grew overnight at 30° C. with shaking at 150 rpm. A 10 µl inoculum was transferred to a second 96-well plate containing 200 µl of YTAG per well and grown with shaking for 1 hour at 37° C. To each well 25 µl YTAG containing $10^9$ plaque forming units (PFU) of helper phage were added, incubated for 30 minutes at 37° C. without shaking, and for an additional 1 hour with shaking (150 rpm) at 37° C. The plates were span for 10 minutes at 1,800 g, the medium was aspirated and the cells were resuspended in 200 µl YTAK and grown overnight at 30° C. while shaking (150 rpm). The plates were then span for 10 minutes at 1,800 g and 100 ml of the supernatant was used in phage ELISA.

ELISA—Plates were coated with 1 µg/well of BSA-Biotin and incubated overnight at 4° C. Following each antibody incubation, the plates were washed three times with PBST (PBS+0.05% Tween-20) followed by one wash with PBS. One pig/well of streptavidin was added, incubated for 1 hour at 37° C. and washed as described above. The plate was divided in two, to one half the FRHSVV-Biotin (1 pig/well) was added, and to the second half a BSA-Biotin (1 µg/well) was added (as a control). The plates were incubated for 1 hour at 37° C., washed, blocked overnight at 4° C. with 3% nonfat dry milk and scFv was added (the amount of scFvs varied between 100 ng to 500 ng for a 1 hour incubation at 37° C. Following incubation with scFv, the plates were washed and the monoclonal anti M13 (Amersham), monoclonal anti His-tag (Sigma) or monoclonal anti MBP (Sigma), depending on the source of the scFvs, were added (each a 1:1000 dilution, according to manufacturer's instruction) for a 1-hour incubation at 37° C., followed by washes. Anti mouse IgG conjugated to HRP was applied, incubated for 1 hour at 37° C., washed and developed using the substrate 3,3',5,5'-tetramethylbenzidine (Sigma) according to manufacturer's instructions. The plates were then scanned in the EasyReader 400 FW ELISA reader (SLT, Austria) at 450 nm.

Mutant and wild type core domain ELISA studies using the mAb 1620 or TAR1 antibodies—Plates were coated overnight at 4° C. with recombinant wild-type or mutant core domains or with PBS as control. The plates were washed and blocked for 2 hours at 37° C. with 3% nonfat dry milk. mAb 1620 or TAR1 antibodies were added and incubated for 1 hour at 37° C. followed by washes. Monoclonal anti MBP conjugated to HRP (dilution 1:1000) was applied, incubated for 1 hour at 37° C., washed and developed using the substrate 3,3',5,5'-tetramethylbenzidine (Sigma)

Expression and purification of scFvs—scFv expression vectors were prepared by fusing the TAT sequence (RKKRRQRRRG; SEQ ID NO:133) to the N-terminus of the scFv and three repeats of the NLS sequence (DPKKKRKV; SEQ ID NO:134) to the C-terminus of the scFv. E. coli cells, transformed with pMalC-NN-TAT-scFv, pMalC-NN-TAT-scFv-NLS, pCANTAB6-TAT-scFv or pCANTAB6-TAT-scFv-NLS (all of the constructs are Histidine-tagged) were grown in LB medium supplemented with 100 μg/ml ampicillin and 1% (w/v) glucose. When the culture reached $A_{600}$ of 0.6-0.9 it was induced with 0.5 mM IPTG at 30° C. for four hour. Cell extracts were prepared in 20 mM Phosphate buffer (pH 7.4), 0.5 M NaCl and 20 mM imidazole by freezing-thawing followed by brief sonication. The extracts were clarified by centrifugation at 20,000 g and scFv was purified on a HisTrap HP column (Amersham Biosciences) using an AKTA prime (Amersham pharmacia biotech) according to the manufacturer's instructions.

BIAcore Analysis—Real time analysis of the interaction between scFvs and FHRSVV-biotin were determined using BIAcore technology (Biacore AB, Uppsala, Sweden) according to manufacturer's instructions. The peptide FRHSVV-biotin was immobilized on a streptavidin coated sensor chip surface SA. The amount of immobilized peptide was 200 pg/mm², the binding was in HBS buffer (10 mM Hepes PH 7.4, 150 mM NaCl, 0.005% Tween-20, 3.4 mM EDTA). Several concentrations of purified scFv (62 nM, 125 nM, 250 nM, 1 μM and 2 μM) were injected at a flow rate of 20 μl/minute. Dissociation was observed for 180 seconds in running buffer (HBS). Regeneration of the sensor chip was performed using 10 μl of 10 mM HCl. The kinetics parameters of the binding reactions were determined by BIAevaluation 4.0 Software (Biacore AB) using the 1:1 Langmuir model. The dissociation rate (off-rate) constant Kd and the association rate constant (on-rate) Ka were determined simultaneously according to manufacturer's instructions.

FACS analysis—Each well was seeded with 3×10⁵ Cells. Twenty-four hours later purified TAT-scFV F2-NLS (250 nM, 0.5 μM, 1 μM or 2 μM) was added to the medium and incubated for additional 24 hour. Cells were harvested by combining the detached cells in the supernatant with the adherent cells from the same well that had been removed by trypsinization. The cells were pelleted, washed with PBS and then fixed by slowly adding 1 ml of cold 70% ethanol. The cells were kept overnight at 4° C., pelleted once again, resuspended in 1 ml PBS and stained by adding 50 μl of propidium iodide (1 mg/ml). The intensity of staining was determined using a FACScalibur Flow Cytometry System (Becton Dickinson).

Establishment of scFv expressing cells—H1299-R175H cells were transfected with pCMV/myc-scFv-F2 plasmid using Fugene (Roche) at a ratio of 2 μg DNA:4 μl Fugene, according to the manufacturer's instructions. Forty-eight hours post transfection the selectable drug G418 (Invitrogen) was added at a concentration of 0.4 mg/ml. The cells were grown in the presence of G418 for 3 weeks to achieve colonies of single cell clones. Each colony was expended and tested for scFv F2 expression by western blot analysis.

Western Blot Analysis—Cells were lysed in a passive lysis buffer (Promega). Protein concentration was determined using the BCA Protein Assay Kit (Pierce). Lysate aliquots were resolved by SDS-PAGE on 10% polyacrylamide gel, transferred to a nitrocellulose membrane and probed with anti MBP-HRP (Sigma) or anti His-HRP (Sigma). Membranes were then developed using the ECL kit (Amersham Biosciences, Uppsala, Sweden).

Immunoprecipitation—For immunoprecipitation studies of the mutant or wild type core domains, the proteins were incubated over night with 80 nM TAR1. Immunoprecipitation was performed with mAb DO-12 antibody (dilution 1:33) and protein G magnetic beads incubated over night at 4° C. Beads were washed with PBS, sample buffer was added and boiled for 5 minutes. The eluted proteins were subjected to Western blot analysis using anti His-HRP (dilution 1:3000) and developed using the ECL kit.

Colony formation—H1299-R175H stably expressing mutant p53 or H1299-R175H-scFv F2 stably expressing both mutant p53 and scFv F2 were seeded at low concentration (500-1000 cells/plate). The cells were grown for two weeks, the medium was aspirated and colonies were stained with Giemsa. The number and size of colonies was determined using the analyze particle tool of the scion (NIH Image Beta 4.0.2) analysis system.

Animal studies—For the assessment of the anti-tumor activity of scFv F2, nine CD1 nude mice (six weeks old) were inoculated with 5×10⁶ H1299-R175H cells subcutaneously and unilaterally into the right flanks. After 3 days mice were divided into two groups. One group of 5 mice received intra-tumor injections of scFv F2 at a dose of 200 μg/mouse, and the second group of 4 mice were injected with PBS and served as control. Injections were given every other day for two weeks. The tumor size was measured and the tumor volume was calculated using the formula $(a^2 \times b)/2$, where (a) is the short axis and (b) is the long axis. Relative volume for each group was determined by dividing the average tumor volume for each data point by the average starting tumor volume.

Circular dichroism measurements—A tandem cuvette (Hellma) was used allowing simultaneous measurement of both p53 core domains and TAR1 separately or in complex. All proteins were diluted to a concentration of 1 μM in 50 mM Tris, 150 mM NaCl. Circular dichroism absorbance measurements were taken in an AVIV instrument. The experiment parameters were as follows: Spectrum scan of 190 nm-250 nm; 1 nm step; 5 seconds measurement average in each step; 3 scans were taken for each sample. Measurements were taken at 4° C.

TUNEL assay—H1299 cells null for p53 or H1299 cells expressing R175H mutant p53 were grown on slides. Cells were incubated overnight in the absence or presence of 1 μM TAR1. Slides were washed with PBS and fixed for 10 minutes at room temperature with 3.7% formaldehyde followed by wash with PBS. Samples were permeabilized with Cytonin for 15 minutes at room temperature and than washed with water. Quenching of endogenous peroxidase was done with 3% H$_2$O$_2$ in methanol for 5 minutes at room temperature. Slides were washed with PBS and TdT labeled for 1 hour at 37° C. with biotinylated nucleotides followed by wash with PBS. Slides were incubated for 10 minutes with Streptavidin-HRP washed twice with PBS and developed with the substrate diaminobenzidine.

Example 1

SCFVs Bind the Common Epitope of Mutant p53 with High Affinity

To identify scFvs that specifically bind the mutant p53 common epitope, a human synthetic combinatorial library of arrayable single-chain antibodies (Azriel-Rosenfeld et al 2004 JMB 335, 177-192) was screened using the biotinylated FRHSVV (SEQ ID NO:1) peptide and the streptavidin Dynabeads (Dynal).

Twenty scFv clones were selected by biopanning using the common epitope of mutant p53—FIGS. 1a-b depict the amino acids sequences of the variable Heavy chain (V$_H$) and variable light chain (V$_L$) of the isolated scFvs selected by biopanning with the FRHSVV (SEQ ID NO:1) peptide of the common epitope of the mutant p53. Table 3, hereinbelow, depicts the amino acid sequences of the CDR1, CDR2 and CDR3 of the variable heavy chain of all scFv clones isolated and described in FIGS. 1a-b and Tables 4 and 5.

TABLE 3

| Variable heavy chain | | |
|---|---|---|
| CDR1 | CDR2 | CDR3 |
| FSGYWMHWV (SEQ ID NO: 5) | EISGSGDSTHYGDSVKG (SEQ ID NO: 6) | GRNGSLDYW (SEQ ID NO: 7) |

Table 3: The amino acid sequence of the CDR1, CDR2 and CDR3 of the variable heavy (VH) chain of all the isolated scFv clones of the present invention (for scFv clone IDs see Table 2, hereinbelow).

Tables 4 and 5, hereinbelow, present the CDRs of the variable light chain of the isolated scFvs (Table 4) and the unique CDRs of the variable light chains (Table 5) of the isolated scFvs selected against the FRHSVV (SEQ ID NO:1) peptide.

TABLE 4

| Variable light chain | | | |
|---|---|---|---|
| CDR1 | CDR2 | CDR3 | scFv Clone ID No. |
| TGSSSNIGADYDVHW (SEQ ID NO: 8) | IYDNHKRPSGV (SEQ ID NO: 9) | CQSWDNSAVVFGGGTQL (SEQ ID NO: 10) | G4 |
| TGSSSNIGAGYDVHW (SEQ ID NO: 11) | IYSNHHRPSGV (SEQ ID NO: 12) | CQVWDSSSDHVVFGGGTQL (SEQ ID NO: 13) | G11 |
| TGSSSNIGAGYDVHW (SEQ ID NO: 14) | IYDNSHRPSGV (SEQ ID NO: 15) | CQVWDSSSEHVEFGGGTQL (SEQ ID NO: 16) | H8 |
| TGTTSNIGAGYDVHW (SEQ ID NO: 17) | IYENDKRPSGV (SEQ ID NO: 18) | CASWDDSLNGHVVFGGGTQL (SEQ ID NO: 19) | B11 |
| TGSSSNIGADYDVHW (SEQ ID NO: 20) | IYGNYHRPSGV (SEQ ID NO: 21) | CSSWDDSQSGHVAFGGGTQV (SEQ ID NO: 22) | A2 |
| TGSSSNIGADYDVHW (SEQ ID NO: 111) | IYDNDKRPSGV (SEQ ID NO: 112) | CAAWDDSLSGPVFGGGTQV (SEQ ID NO: 23) | A3 |
| TGSSSNIGADYDVHW (SEQ ID NO: 24) | IYDNDKRPSGV (SEQ ID NO: 25) | CAVWDDSLNAVVFGGGTKV (SEQ ID NO: 26) | C6 |
| TGSSANIGAGYDVHW (SEQ ID NO: 27) | IYDNDKRPSGV (SEQ ID NO: 28) | CAAWDDRLSGVVFGGGTKV (SEQ ID NO: 29) | B6 |
| TGNSSNIGAGYDVHW (SEQ ID NO: 30) | IYSNNQRPSGV (SEQ ID NO: 31) | CAAWDDSLNGPVFGGGTQV (SEQ ID NO: 32) | A5 |
| TGSSSNIGAGYDVHW (SEQ ID NO: 33) | IYANNNRPSGV (SEQ ID NO: 34) | CAAWDDNLNGLVFGGGTQL (SEQ ID NO: 35) | D12 |
| TGNSSNIGAGYDVHW (SEQ ID NO: 36) | IYSNNQRPSGV (SEQ ID NO: 37) | CAAWDDSLSSVVFGGGTKL (SEQ ID NO: 38) | A4 |
| SGTSSNIGADYDVHW (SEQ ID NO: 39) | IYDNNKRPSGV (SEQ ID NO: 40) | CAAWDSSLSSVVFGGGTQL (SEQ ID NO: 41) | F2 |
| SGSSSNIGADYDVHW (SEQ ID NO: 42) | IYSNNQRPSGV (SEQ ID NO: 43) | CAAWDDSLNGYVFGTGTKL (SEQ ID NO: 44) | E4 |
| SGSSSNIGAGYDVHW (SEQ ID NO: 45) | IYGNTNRPSGV (SEQ ID NO: 46) | CQSFDSTLSGPVFGGGTKV (SEQ ID NO: 47) | E6 |
| SGSSSNIGAGYDVHW (SEQ ID NO: 48) | IYGNTNRPSGV (SEQ ID NO: 49) | CAAWDDSLNGLVFGGGTQV (SEQ ID NO: 50) | F6 |

TABLE 4-continued

Variable light chain

| CDR1 | CDR2 | CDR3 | scFv Clone ID No. |
|---|---|---|---|
| SGSNSNIGAGYDVQW (SEQ ID NO: 51) | IYANSNRPSGV (SEQ ID NO: 52) | CGVWDDSLNGPVFGGGTPV (SEQ ID NO: 53) | D10 |
| TGGSSNIGNHHVSW (SEQ ID NO: 54) | IYGNTNRPSGV (SEQ ID NO: 55) | CQVWDSSSDHVVFGGGTKV (SEQ ID NO: 56) | D4 |
| SGTSSNIGSHTVHW (SEQ ID NO: 57) | IYEVNKRPSGV (SEQ ID NO: 58) | CQSYDSSLSAVVFGGGTQV (SEQ ID NO: 59) | F7 |
| TGGRFNIGDYAVHW (SEQ ID NO: 60) | IYDNDRRPSGV (SEQ ID NO: 61) | CAAWDDSLDGLVFGGGTQL (SEQ ID NO: 62) | A6 |
| TGGRFNIGDYAVHW (SEQ ID NO: 63) | IYDNDRRPSGV (SEQ ID NO: 64) | CQSFDSTLSGPVFGGGTKV (SEQ ID NO: 65) | C5 |

Table 4: The amino acid sequence of the CDR1, CDR2 and CDR3 of the variable light chain of the various scFv clones are presented (SEQ ID NOs: 8-65 and 111-112).

TABLE 5

Light chain Unique CDRs

| CDR1 | CDR2 | CDR3 |
|---|---|---|
| TGSSSNIGADYDVHW (SEQ ID NO: 66) | IYDNHKRPSGV (SEQ ID NO: 67) | SWDNSAVVFGGGTQL (SEQ ID NO: 68) |
| TGSSSNIGAGYDVHW (SEQ ID NO: 69) | IYSNHHRPSGV (SEQ ID NO: 70) | QVWDSSSDHVVFGGGTQL (SEQ ID NO: 71) |
| TGTTSNIGAGYDVHW (SEQ ID NO: 72) | IYDNSHRPSGV (SEQ ID NO: 73) | QVWDSSSEHVEFGGGTQL (SEQ ID NO: 74) |
| TGSSANIGAGYDVHW (SEQ ID NO: 75) | YENDKRPSGV (SEQ ID NO: 76) | ASWDDSLNGHVVFGGGTQL (SEQ ID NO: 77) |
| TGNSSNIGAGYDVHW (SEQ ID NO: 78) | YGNYHRPSGV (SEQ ID NO: 79) | SSWDDSQSGHVAFGGGTQV (SEQ ID NO: 80) |
| SGTSSNIGADYDVHW (SEQ ID NO: 81) | YDNDKRPSGV (SEQ ID NO: 82) | AAWDDSLSGPVFGGGTQV (SEQ ID NO: 83) |
| SGSSSNIGADYDVHW (SEQ ID NO: 84) | YSNNQRPSGV (SEQ ID NO: 85) | AVWDDSLNAVVFGGGTKV (SEQ ID NO: 86) |
| SGSSSNIGAGYDVHW (SEQ ID NO: 87) | ANNNRPSGV (SEQ ID NO: 88) | AAWDDRLSGVVFGGGTKV (SEQ ID NO: 89) |
| SGSNSNIGAGYDVQW (SEQ ID NO: 90) | YDNNKRPSGV (SEQ ID NO: 91) | AAWDDSLNGPVFGGGTQV (SEQ ID NO: 92) |
| TGGSSNIGNHHVSW (SEQ ID NO: 93) | GNTNRPSGV (SEQ ID NO: 94) | AAWDDNLNGLVFGGGTQL (SEQ ID NO: 95) |
| SGTSSNIGSHTVHW (SEQ ID NO: 96) | ANSNRPSGV (SEQ ID NO: 97) | AWDDSLSSVVFGGGTKL (SEQ ID NO: 98) |
| TGGRFNIGDYAVHW (SEQ ID NO: 99) | EVNKRPSGV (SEQ ID NO: 100) | AAWDSSLSSVVFGGGTQL (SEQ ID NO: 101) |
| | IYDNDRRPSGV (SEQ ID NO: 102) | AAWDDSLNGYVFGTGTKL (SEQ ID NO: 103) |
| | | CQSFDSTLSGPVFGGGTKV (SEQ ID NO: 104) |
| | | CAAWDDSLNGLVFGGGTQV (SEQ ID NO: 105) |
| | | NGPVFGGGTPV (SEQ ID NO: 106) |
| | | CQVWDSSSDHVVFGGGTKV (SEQ ID NO: 107) |
| | | LSAVVFGGGTQV (SEQ ID NO: 108) |
| | | CAAWDDSLDGLVFGGGTQL (SEQ ID NO: 109) |
| | | CQSFDSTLSGPVFGGGTKV (SEQ ID NO: 110) |

Table 5: The unique amino acid sequences of the CDR1, CDR2 and CDR3 of the variable light chain of the various scFv clones are presented (SEQ ID NOs: 66-110).

ScFvs F2, A4 and B6 are specific to the common epitope of mutant p53—The F2, A4 and B6 scFvs were tested for their binding capacity to the Bovine Serum Albumin (BSA) and Streptavidin proteins and the FRHSVV (SEQ ID NO:1), β amyloid peptide DAEFRHDSGYEVHHQK SEQ ID NO:2), MAP-PrP (DYEDRYYRE; SEQ ID NO:3) and the PaP (ILL-WQPIPV; SEQ ID NO:4) peptides. As is shown in FIG. 9, the F2 scFv, A4 scFv and to a lesser extent, the B6 scFv exhibited high affinity towards the peptide derived from the common epitope of mutant p53. On the other hand, these antibodies exhibited low affinity towards the other peptides or proteins tested.

The scFv F2 and E6 antibodies display high affinity binding of the mutant epitope—To determine the affinity binding of the isolated scFvs towards the target peptide (SEQ ID NO:1), the BIAcore technology was employed. A biotin conjugate of the peptide (FRHSVV; SEQ ID NO:1) was immobilized on a streptavidin coated sensor chip surface and the binding specificity was determined using increasing concentrations of the purified F2 and E6 scFvs. As is shown in FIGS. 2a-b, both the F2 (FIG. 2a) and E6 (FIG. 2b) scFvs were capable of binding the common epitope of the mutant p53 with an affinity of $1.1 \times 10^{-8}$ and $4.6 \times 10^{-14}$ M, respectively. These results demonstrate, for the first time, the isolation of human antibodies directed against the common epitope of p53 with an affinity suitable for therapeutic applications.

The F2 and A4 antibodies are specific to the common epitope of mutant p53—As is shown in FIG. 9, ELISA performed using the F2, A4 and B6 scFvs revealed that the F2 and A4 antibodies are highly specific to the peptide derived from the common epitope of mutant p53 (SEQ ID NO:1).

Example 2

The Isolated SCFVs Bind Whole Mutant P53 Proteins with Severe Conformational Changes To demonstrate the binding capacity of the isolated scFvs to whole p53 molecules, ELISA plates were coated with recombinant wild-type p53 or mutant p53-R175H, p53-R248H and p53-R273W whole proteins which were produced in sf9 insect cells and 100-500 ng scFv F2 were added.

As is shown in FIG. 3, the F2 scFv (also designated herein as TAR1) purified antibody differentially bound to the various p53 proteins. While binding of the F2 scFv to the wild type p53 protein was relatively low ($OD_{492}$ nm ~0.1), binding to the p53 mutants exhibiting a severe conformational change (e.g., R175H) or an intermediate conformational change (e.g., R248W) was significantly high ($OD_{492}$ nm >0.25). Thus, the severe conformational change in p53 protein which results in a higher exposure of the common mutant epitope is more susceptible to the antibodies of the present invention.

These results suggest the use of the antibody of the present invention (e.g., F2 scFv) to specifically and differentially target mutant p53 proteins without affecting wild-type p53 proteins.

Example 3

The F2 SCFV Antibody (TAR1) Induces Apoptosis and Inhibit Colony Formation in Cells Expressing Mutant p53

The apoptotic activity of wild type p53 is a major contributor to its tumor suppressor function. However, this activity is lost when p53 is mutated. To determine whether F2 SCFV (TAR1) can restore the apoptotic function to mutant p53, cancer cell lines stably expressing the mutant R175H p53 protein were treated with TAR1 and the effect on apoptosis was determined using the FACS and TUNEL analyses, as follows.

F2 scFv (TAR1) is capable of inducing apoptosis—The purified isolated F2 scFv antibody (TAR1) was tested for its capacity to induce apoptosis in H1299 human lung carcinoma cells expressing the mutant R175H p53 protein. As is shown in FIGS. 4a-j and 15a-d, while in cells expressing the mutant R175H p53 protein treatment for 24 hours with the F2 scFv antibody (TAR1) caused apoptosis in a dose-dependent manner (e.g., ~13% and ~32% of apoptotic cells in the presence of 0.5 and 2 µM F2 scFv, respectively; FIGS. 4a-e and FIG. 15a-b), in lung carcinoma cells not expressing the R175H p53 protein, the F2 scFv antibody failed to induce apoptosis (FIGS. 4f-j and FIGS. 15c-d).

Similar results were obtained when HCT116 colon carcinoma cells stably expressing mutant p53 R175H, were treated for 24 hours with 1 µM TAR1. As is shown in FIGS. 15e-h, TAR1 caused a substantial increase in the fraction of cells with a sub-G1 DNA content, indicating DNA fragmentation and cell death (FIG. 15f). Induction of apoptosis was not apparent in HCT116 cells expressing wild-type p53 (FIG. 15h) indicating that induction of apoptosis by TAR1 is mutant p53 dependent.

These results were corroborated by the TUNEL assay shown in FIGS. 16a-d. Staining of apoptotic cells was evident only in H1299 cells expressing mutant p53 R175H that were treated with TAR1 (FIG. 16b) but not in untreated cells (FIG. 16a). No staining was observed in H1299 cells null for p53 regardless whether cells were treated with TAR1 (FIG. 16d) or not (FIG. 16c).

TAR1 is capable of inducing cell death by apoptosis in cancerous cell lines expressing endogenous mutant p53 proteins—The effect of TAR1 on cell death was further tested in a panel of nine human tumor cell lines endogenously expressing different point mutations in their p53 core domains, representing various tumor types including colon (KM12-C, SW480, Colon 320), breast (T47D, SKBR3, MCF7, MDA231), brain (e.g., neuroblastoma LAN1) and pancreas (PANC1). Cells were treated for 24 hours with 1 µM TAR1 (FIGS. 17b, d, f, h, j, l, n, p, r) or remained untreated (FIGS. 17a, c, e, g, i, k, m, o, q) and the effect on apoptosis was assessed using FACS analysis. As is shown in FIGS. 17a-r, TAR1 treatment resulted in a differential induction of apoptosis in all tested cell lines regardless of the nature of their point mutation or the tumor type, as manifested by the accumulation of cells in the sub-G1 fraction.

Cells expressing the F2 scFv exhibit reduced colony formation—To further substantiate the effect of the F2 scFv antibody on apoptosis and cell growth, cells harboring the mutant p53 protein (R175H) were stably transfected with an expression vector harboring the F2 scFv antibody and the effect on cell growth was determined in tissue cultures seeded with 500-1000 cells/plate. As is shown in FIGS. 6a-d, both the number of colonies and colony area were significantly reduced in cells expressing the F2 scFv antibody.

Altogether, these results demonstrate that the F2 scFv antibody of the present invention can induce apoptosis and inhibit colony formation. These results suggest the use of the scFv antibodies of the present invention in treating cancer in cells expressing mutant p53.

The F2 scFv increases susceptibility of cells expressing mutant p53 to chemotherapy drugs—To test the potential use of the scFv antibodies of the present invention in combination with common chemotherapy drugs, the effect of the etoposide and cisplatin drugs was tested on cells expressing mutant p53 in the presence or absence of the F2 scFv antibody. As is shown in FIG. 5, while cells expressing the F2 scFv antibody were highly susceptible to the chemotherapy drugs at concentrations as low as 0.5 µg/ml of cisplatin or 1 µM of etoposide, human lung carcinoma cells not expressing the scFv antibody were less susceptible towards such drugs.

These results further suggest the use of the scFv antibodies of the present invention in treating cancer in combination with other drugs.

Example 4

The F2 SCFV Antibody Suppresses Tumor Growth In Vivo

To test the ability of the F2 scFv antibody of the present invention to inhibit tumor cell growth in vivo, nude mice were subject to subcutaneous injection of human lung carcinoma cell (H1299-R175H). Three days later, the mice received an intra-tumor injection of scFv F2 (200 µg) or PBS (50 µl) which was repeated every other day for two weeks. As is shown in FIG. 7, while in the PBS-treated mice the tumor size drastically increased within 28-36 days post inoculation, in the F2 scFv-treated mice, the tumor size remained unchanged, even following 36 days. FIGS. 8a-f depict the suppression of tumors in F2 scFv-treated mice. Altogether, these results demonstrate the use of the purified F2 scFv antibody in suppressing tumor growth in vivo.

Example 5

Restoration of Wild-Type p53 Conformation to Mutant p53

The present inventors employed biochemical and biophysical methods to determine whether binding of TAR1 (i.e., the F2 scFV antibody) to mutant p53 can restore the wild-type protein folding, as follows.

Experimental Results

TAR1 increases the binding of mAb 1620, a wild type p53-specific antibody, to the p53 R175H mutant—Recombinant polypeptides of the P53 core domain (including amino acids 94-312 of the p53 protein set forth by SEQ ID NO:135; GenBank Accession No. NP_000537) of wild-type and R175H mutant P53 proteins were subjected to ELISA and immunoprecipitation assays using conformation specific monoclonal antibodies. The first step was to establish that the purified recombinant core domain proteins exhibit the specific conformation of wild-type and mutant p53 proteins. An ELISA assay using TAR1 antibody (which recognizes the same epitope as mAb 240), which is specific to the mutant conformation (FIG. 10a) and the mAb 1620 (Abcam Laboratories, Ltd, UK), which is specific to the wild-type conformation (FIG. 10b), confirmed that this indeed was the case. Binding of TAR1 to mutant p53 R175H and wild-type core domains upon heating for 30 or 60 minutes at 37° C. resulted in a three-fold increase in the mAb 1620 positive fraction of the mutant core domain and prevention of unfolding of the wild-type core domain and stabilization of wild-type p53 conformation (FIGS. 10c and d). To substantiate these results the mAb DO-12 (Novocastra Laboratories, Ltd, UK), which is specific for the mutant p53 conformation, yet binds to a different epitope than TAR1, was employed in an immunoprecipitation assay. Binding of TAR1 to mutant p53 core domain caused a dramatic decrease in the DO-12 positive fraction, but had no effect on wild-type core domain (FIG. 11a).

Binding with TAR1 causes a shift in the spectrum of mutant p53—Circular dichroism is a method for analyzing protein secondary structure in solution and can determine whether protein-protein interaction alter the conformation of the protein. Conformational changes in the proteins result in a spectrum that is different from the sum of the individual components. The circular dichroism method was employed using the TAR1 antibody and wild-type p53 or mutant R175H core domains. Binding of TAR1 caused a shift in the spectrum of mutant p53 while almost no difference was observed in the spectrum of the wild-type core domain indicating a conformational change in the complex of TAR1 and mutant p53. The spectra of both TAR1 complexes, with wild-type p53 and with mutant p53, are very similar indicating conformational similarity (FIG. 12).

TAR1 treatment of cells expressing mutant p53 increases the binding of mAb 1620 to extract of such cells—As is shown in FIG. 11b, a change in conformation of mutant p53 could be detected in H1299 cells stably expressing mutant p53 R175H. Upon treatment of these cells with TAR1 an increase in the fraction of cells adopting wild-type conformation was observed, as judged by immunoprecipation with the wild-type specific mAb 1620.

Altogether, these results demonstrate that TAR1 is capable of restoring wild type conformation to mutant p53 core domain.

Example 6

TAR1 Restores Transcriptional Transactivation to Mutant p53

Loss of the ability to transactivate transcription of wild-type p53 target genes is one of mutant p53 characteristic features. The present inventors have tested the ability of TAR1 to restore P53 transcriptional transactivation function in cells expressing mutant p53, as follows. H1299 cells stably expressing mutant p53 R175H protein were treated for 24 hours with TAR1 and the expression level of p21, MDM2 and Bax was examined by Western blot analyses. Treatment of cells with TAR1 resulted in an increase in the expression level of three endogenous wild-type p53 target genes p21 (FIG. 13a), MDM2 (FIG. 13b) and Bax (FIG. 13d) in a concentration dependent manner. The expression level of tubulin served as an internal control for protein levels used in each experiment (FIGS. 13e-h). Furthermore, some mutant p53 proteins have been shown to transactivate transcription of genes different from those activated by wild-type p53, one of them is EGR1. As is shown in FIG. 13c, treatment of the cells with TAR1 abrogated the gain of function activity of the mutant p53 protein as manifested by the lower expression of EGR1 in the treated cells.

Thus, these results demonstrate, that the TAR1 antibody of the present invention is capable of restoring the transcriptional transactivation function of wild-type specific target genes (e.g., p21, MDM2 and Bax) and preventing the transcriptional activation of mutant P53.

Example 7

Viral Display Vehicles are Useful Therapeutic Agents

The present inventors have designed a viral display vehicle capable of penetrating into mammalian cells (e.g., CHO cells) which can be used to deliver the anti-p53 antibody of the present invention (e.g., TAR1) into cell-of-interest, as follows.

A filamentus phage, fuse 88, expressing a PTD (e.g the peptide PEP as shown in FIGS. 18a-b) on the coat protein VIII. The PEP peptide (SEQ ID NO:136) enables the penetration of the phage into the cell. The filamentus phage also includes the scFv of the present invention (e.g., TAR1) fused to an NLS (SEQ ID NO:134) on protein III. The NLS peptide enables nuclear localization of the phage. The results presented in FIGS. 18-21 demonstrate that the phage PEP is capable of penetrating mammalian cells and has no toxic effect on these cells. Such a filamentus phage (i.e., the viral display vehicle) can be administered intranasally as a therapeutic agent for treatment of brain tumors.

Thus, these results demonstrate the use of the viral display vehicle which includes the anti-p53 antibody of the present invention for the treatment of p53 related diseases.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

1. Govorko D, Cohen G and Solomon B., 2001, J. Immunol. Methods. 258: 169-81.
2. Hupp T. R and Lane D. P., 1994, Curr. Biol. 4: 865-875.
3. Gannon J V, et al., 1990, EMBO J. 9(5): 1595-602.
4. Govorko D, Cohen G and Solomon B., 2001, J. Immunol. Methods. 258: 169-81.
5. Azriel-Rosenfeld R, et al., 2004, J. Mol. Biol. 335(1): 177-92.

What is claimed is:

1. An isolated polypeptide that specifically binds an exposed epitope shared by p53 mutant proteins and not by wild type p53 protein, wherein said polypeptide has affinity for said epitope of less than 25 nanomolar and wherein said polypeptide comprises a heavy chain variable domain comprising a complementarity determining region 1 (CDR1) comprising the amino acid sequence of SEQ ID NO: 5, a CDR2 comprising the amino acid sequence of SEQ ID NO: 6, a CDR3 comprising the amino acid sequence of SEQ ID NO: 7 and a light chain variable region comprising a CDR1 comprising the amino acid sequence of SEQ ID NO: 39, a CDR2 comprising the amino acid sequence of SEQ ID NO: 40 and a CDR3 comprising the amino acid sequence of SEQ ID NO: 41.

2. A composition comprising the isolated polypeptide of claim 1, and a pharmaceutically acceptable carrier.

3. A composition comprising a viral display vehicle comprising on the surface of the viral display vehicle the isolated polypeptide of claim 1.

* * * * *